(12) United States Patent
Helkowski et al.

(10) Patent No.: US 12,714,640 B2
(45) Date of Patent: Aug. 25, 2026

(54) DATA MANAGEMENT SYSTEM AND METHODS FOR CHEST COMPRESSION DEVICES

(71) Applicant: Zoll Circulation, Inc., San Jose, CA (US)

(72) Inventors: Richard A. Helkowski, Redwood City, CA (US); Byron J. Reynolds, Gilroy, CA (US); Dean Severns, San Jose, CA (US)

(73) Assignee: Zoll Circulation, Inc., San Jose, CA (US)

( * ) Notice: Subject to any disclaimer, the term of this patent is extended or adjusted under 35 U.S.C. 154(b) by 1368 days.

(21) Appl. No.: 17/217,156

(22) Filed: Mar. 30, 2021

(65) Prior Publication Data

US 2021/0322265 A1 Oct. 21, 2021

Related U.S. Application Data

(60) Provisional application No. 63/003,023, filed on Mar. 31, 2020.

(51) Int. Cl.
*A61H 31/00* (2006.01)
*A61N 1/39* (2006.01)

(52) U.S. Cl.
CPC ......... *A61H 31/005* (2013.01); *A61H 31/006* (2013.01); *A61H 2201/0153* (2013.01);
(Continued)

(58) Field of Classification Search
CPC ................ A61H 31/005; A61H 31/006; A61H 2201/0153; A61H 2201/0157;
(Continued)

(56) References Cited

U.S. PATENT DOCUMENTS 6,321,113 B1 * 11/2001 Parker .................... G16H 20/30 607/5
7,220,235 B2 5/2007 Geheb et al.
(Continued)

OTHER PUBLICATIONS

"Lucas 3 Chest Compression System Version 3.1 Instructions for Use," 2018, Jolife AB.
(Continued)

*Primary Examiner* — Valerie L Woodward
(74) *Attorney, Agent, or Firm* — Secant IP, P.L.L.C.

(57) ABSTRACT

A medical resuscitation system includes a platform for releasable coupling to a patient for delivery of mechanical chest compressions, the platform having sensor(s) for monitoring aspect(s) of compression delivery, and processing circuitry configured to control the delivery chest compressions during a patient therapy session; receive, during the session, signals from each sensor; and store, to a memory, operational data collected for use by an authorized user in troubleshooting a problem with the platform and/or gathering historic data regarding use of the platform, and clinical metrics regarding the delivery of the compressions during the session, where the clinical metrics are collected for use in a summary report accessible to a clinical user. The summary report may be transferred to a server or a portable computer readable medium. The operational data may be transferred to an accessory unit or data integrator configured to cooperate with the platform for providing the therapy.

21 Claims, 19 Drawing Sheets

(52) U.S. Cl.
CPC ................ *A61H 2201/0157* (2013.01); *A61H 2201/107* (2013.01); *A61H 2201/5012* (2013.01); *A61H 2201/5015* (2013.01); *A61H 2201/5043* (2013.01); *A61H 2201/5061* (2013.01); *A61H 2201/5097* (2013.01); *A61H 2230/04* (2013.01); *A61N 1/39044* (2017.08)

(58) Field of Classification Search
CPC ...... A61H 2201/107; A61H 2201/5012; A61H 2201/5015; A61H 2201/5043; A61H 2201/5061; A61H 2201/5097; A61H 2230/04; A61H 2201/1621; A61H 2201/5058; A61H 2203/0456; A61H 2230/425; A61N 1/39044; G16H 50/20; G06F 21/602; G06F 21/6245; G06F 21/64
See application file for complete search history.

(56) References Cited

U.S. PATENT DOCUMENTS 8,478,401 B2 7/2013 Freeman
9,119,971 B2 9/2015 Elghazzawi
9,220,912 B2 12/2015 Elghazzawi
10,195,343 B2 2/2019 Kamen et al.
2004/0082888 A1* 4/2004 Palazzolo .............. A61B 5/053 601/41
2004/0162510 A1* 8/2004 Jayne ................... A61H 31/005 601/44
2007/0033174 A1* 2/2007 Cornacchia, III .. G06F 16/3343
2010/0198118 A1* 8/2010 Itnati .................... A61H 31/006 601/41
2012/0274280 A1* 11/2012 Yip ..................... H02J 7/00302 320/112
2013/0296719 A1* 11/2013 Packer ................... G16H 80/00 600/484
2016/0294951 A1* 10/2016 Durrant ................... H04L 41/22
2018/0168923 A1* 6/2018 Quan ..................... A61B 5/318
2018/0185221 A1 7/2018 Hayes et al.
2018/0185240 A1 7/2018 von Schenck et al.
2018/0200142 A1* 7/2018 Freeman ................ A61B 5/349
2019/0175443 A1* 6/2019 Härdig ................. A61H 31/005
2019/0349435 A1 11/2019 Durrant et al.

OTHER PUBLICATIONS

"Lucas 3 Chest Compression System, v3.1, Connectivity Guide," 2018, Jolife AB.

* cited by examiner

DATA MANAGEMENT SYSTEM AND METHODS FOR CHEST COMPRESSION DEVICES

RELATED APPLICATIONS

This application claims priority to U.S. Provisional Patent Application Ser. No. 63/003,023, entitled "Data Management System and Methods for Chest Compression Devices," filed Mar. 31, 2020. All above identified applications are hereby incorporated by reference in their entireties.

BACKGROUND

Cardiopulmonary resuscitation (CPR) is a well-known and valuable method of first aid used to resuscitate people who have suffered from cardiac arrest. CPR requires repetitive chest compressions to squeeze the heart and the thoracic cavity to pump blood through the body.

Mechanical compression devices have been developed to address the need for consistent and sustained compressions. One example is the AUTOPULSE® mechanical compression device by ZOLL Medical Corporation. Mechanical compression devices may include processing circuitry such as a controller unit to control the operation of the device.

SUMMARY OF ILLUSTRATIVE EMBODIMENTS

This document describes various systems and methods for data management of chest compression platforms. In one aspect, the present disclosure relates to a medical resuscitation system, including a platform configured for releasable coupling to a patient for delivery of mechanical chest compressions, the platform including at least one sensor, each sensor for monitoring a respective aspect of at least one aspect of the delivery of the mechanical chest compressions, and a housing including a non-volatile memory, and processing circuitry configured to control the delivery of the mechanical chest compressions during a session of therapy delivery to the patient, receive, during the session, a number of signals from each sensor of the at least one sensor, store, to the memory, operational data including at least one of a) the number of signals or b) at least one device performance metric derived from the number of signals, where the operational data is collected for use in troubleshooting a problem with the platform and/or gathering historic data regarding use of the platform, and the operational data is formatted by the processing circuitry to be accessible by an authorized user, and a number of clinical metrics regarding the delivery of the mechanical chest compressions during the session, where the number of clinical metrics is derived from at least a portion of the number of signals, and the number of clinical metrics is collected for use in a summary report accessible to a clinical user, and transfer, to a server, receiver or a portable computer readable medium, the summary report including at least a portion of the number of clinical metrics.

In some implementations, the housing includes a communication port, and the summary report is transferred to a portable device after connection of the portable computer readable medium to the housing via the communication port.

In some implementations, the communication port is type of a Universal Serial Bus (USB) port.

In some implementations, upon detection of the connection to the portable computer readable medium via the communication port, the operational data is transferred to the portable computer readable medium in an encrypted format.

In some implementations, a portable computing device includes the portable computer readable medium.

In some implementations, the portable computer readable medium is a flash drive.

In some implementations, the housing includes a communication transmitter, and the processing circuitry is configured to transfer, via the communication transmitter, at least a portion of the operational data for receipt by accessory unit for storage on a second non-volatile memory of the accessory unit.

In some implementations, the accessory unit is releasably coupled to the platform or is a portable computing device.

In some implementations, the processing circuitry is configured to transfer the portion of the operational data to the accessory unit after the accessory unit is coupled to the platform.

In some implementations, the communication transmitter is a wireless communication transmitter.

In some implementations, the wireless communication transmitter is a short-range wireless communication transmitter.

In some implementations, the short-range wireless communication transmitter is one of a Bluetooth transmitter or a radio frequency transmitter.

In some implementations, the accessory unit is a power unit configured to provide power to the platform for the delivery of the mechanical chest compressions.

In some implementations, the system includes the accessory unit, the accessory unit including a housing including second processing circuitry, the second non-volatile memory, and a communication receiver. The second processing circuitry may be configured to store, to the second memory, a number of accessory unit metrics regarding functionality of the accessory unit, and receive, from the platform via the communication receiver, the portion of the operational data.

In some implementations, the second processing circuitry is configured to store, to the second memory, the portion of the operational data.

In some implementations, the number of accessory metrics includes at least one of a voltage, a temperature, a current, a state of charge, or an error status.

In some implementations, the accessory unit is a ventilator.

In some implementations, the number of accessory unit metrics includes a number of event markers corresponding to a number of physiological events.

In some implementations, the accessory unit is a defibrillator.

In some implementations, the number of accessory metrics includes at least one of a current delivered, a physiologic waveform, a blood pressure, a device status, and an operational mode.

In some implementations, the processing circuitry is further configured to transfer, via a wireless network, at least a portion of the number of clinical metrics for presentation to a remote medical professional, receive, from the remote medical professional, assistance data including at least one of audio data and text data, and present, to a clinical user, the assistance data.

In some implementations, the portion of the clinical metrics includes compression metrics of a treatment session of the platform.

In some implementations, the portion of the clinical metrics includes physiological metrics of the patient.

In some implementations, at least a portion of the physiological metrics are obtained from an accessory device of the medical device platform.

In some implementations, the processing circuitry is further configured to receive, from the clinical user, input data including at least one of audio input and text input, and transmit, to the remote medical professional, the input data.

In some implementations, the medical resuscitation system includes a data integrator configured for data communication with the accessory unit, the data integrator including a housing including third processing circuitry, a third non-volatile memory, a second communication receiver, where the communication receiver of the accessory unit is a transmitter/receiver, and a network communication port for establishing a network connection to communicate with a remote computing system. The third processing circuitry may be configured to receive, upon connection to the accessory unit via the second communication receiver, the portion of the operational data and the number of accessory unit metrics, and transfer, to the remote computing system via the network communication port, the portion of the operational data and the number of accessory unit metrics.

In some implementations, the transmitter/receiver of the accessory unit is one of a Bluetooth or an RF transmitter/receiver.

In some implementations, the third processing circuitry is configured to store, to the third memory, the portion of the operational data and the number of accessory unit metrics, where transferring the portion of the operational data and the number of accessory unit metrics includes transferring, to the remote computing system, upon establishing the network connection.

In some implementations, the network connection is a wired network connection.

In some implementations, the network communication port is an Ethernet port.

In some implementations, the network communication port is a Wi-Fi communication port.

In some implementations, the data integrator is a defibrillation unit.

In some implementations, the third processing circuitry is configured to store, to the third memory, a number of data integrator metrics regarding functionality of the data integrator, and transferring includes transferring the number of integrator metrics.

In some implementations, the accessory unit is configured to releasably couple to the data integrator.

In some implementations, the second processing circuitry is configured to transfer the portion of the operational data and the accessory unit data to the data integrator after the accessory unit is coupled to the data integrator.

In some implementations, the communication transmitter is a wireless communication transmitter.

In some implementations, the wireless communication transmitter is a short-range wireless communication transmitter.

In some implementations, the short-range wireless communication transmitter is one of a Bluetooth transmitter or a radio frequency transmitter.

In some implementations, the accessory unit is a power unit, and the data integrator includes a charger for a battery of the power unit.

In some implementations, the medical resuscitation system includes a data integrator configured for data communication with the platform, the data integrator including a housing including second processing circuitry, a second non-volatile memory, a communication receiver, and a network communication port for establishing a network connection to communicate with a remote computing system. The second processing circuitry may be configured to store, to the second memory, a number of data integrator metrics regarding functionality of the data integrator, receive, upon connection to the platform via the wireless communication receiver, the portion of the operational data, store, to the second memory, the portion of the operational data, and upon establishing the network connection via the network communication port, transfer, to the remote computing system, the portion of the operational data and the data integrator metrics.

In some implementations, the second processing circuitry is configured to merge the portion of the operational data with the data integrator metrics.

In some implementations, the data integrator is a defibrillation unit.

In some implementations, the network connection is a wired network connection.

In some implementations, the communication receiver is a wireless communication receiver.

In some implementations, the wireless communication receiver is a Wi-Fi receiver.

In some implementations, the wireless communication receiver is one of a Bluetooth receiver or an RF receiver.

In some implementations, the network communication port is a Wi-Fi communication port.

In some implementations, the second processing circuitry is further configured to transfer, via the network communication port, at least a portion of the number of clinical metrics for presentation to a remote medical professional, receive, from the remote medical professional, assistance data including at least one of audio data and text data, and cause presentation of the assistance data to a clinical user.

In some implementations, the portion of the clinical metrics includes compression metrics of a treatment session of the platform.

In some implementations, the second processing circuitry is further configured to transfer, via the network communication port, at least a portion of the data integrator metrics for presentation to the remote medical professional.

In some implementations, the data integrator is a defibrillation unit and the portion of the data integrator metrics includes blood pressure metrics and/or physiologic waveforms.

In some implementations, the processing circuitry is further configured to receive, from the clinical user, input data including at least one of audio input and text input, and transmit, to the remote medical professional, the input data.

In some implementations, the second processing circuitry is further configured to receive, upon connection to an accessory unit via the communication receiver, accessory data, and store, to the second memory, the accessory data.

In some implementations, the accessory unit is a portable computing device.

In some implementations, the second processing circuitry is further configured to match data records including at least a portion of the accessory data with at least a portion of the operational data by at least one of an event marker or a timestamp.

In some implementations, the second processing circuitry is further configured to, using the matched data records, calculate one or more integrated metrics.

In some implementations, the communication receiver is a transmitter/receiver, and the second processing circuitry is further configured to provide, upon connection to an accessory unit via the communication receiver, the portion of the operational data.

In some implementations, the data integrator is a defibrillation unit.

In some implementations, the accessory unit includes third processing circuitry configured to merge the portion of the operational data with accessory data collected by the accessory unit.

In some implementations, the non-volatile memory is inaccessible to a user of the platform.

In some implementations, the at least one sensor includes at least one of a voltage sensor, a temperature sensor, a current sensor, a position encoder, or an airflow sensor.

In some implementations, the number of signals includes at least one of a number of pressure sensor readings or a number of load sensor readings.

In some implementations, the at least one device performance metric includes at least one of a temperature, a voltage, an error code, or a platform tilt angle.

In some implementations, the number of clinical metrics includes at least one of a compression rate, compression depth, a number of treatment pauses, a compression duty cycle, or compression fraction.

In some implementations, the number of clinical metrics includes at least one physiologic measurement.

In some implementations, the at least one physiologic measurement includes an ECG measurement or a blood pressure measurement.

In some implementations, the number of clinical metrics includes a subset of the at least one device performance metric.

In some implementations, the platform is a belt style chest compression device and the at least one device performance metric includes at least one of an initial belt position or a belt travel distance.

In some implementations, the platform is a piston style chest compression device and the at least one device performance metric includes at least one of a piston travel distance or a force application position.

In some implementations, the summary report includes one or more of a session begin time, a session end time, a device identifier, and a session length.

In some implementations, the at least one sensor includes a GPS receiver, where the session begin time is derived from a current time obtained via the GPS receiver.

In some implementations, the summary report includes a location of treatment.

In one aspect, the present disclosure relates to a method for securely sharing data within a medical resuscitation system, the method including receiving, by a controller of an automated chest compression device, activation of a usage session, collecting, by the controller, data for the usage session, where collecting the data includes obtaining, from each sensor of at least one sensor of the automated chest compression device, a number of sensor signals, and logging, by the controller to a non-volatile computer readable memory, a number of clinical metrics and operational data, where the operational data includes i) at least a portion of the number of sensor signals and/or ii) a number of device performance metrics derived from the number of sensor signals, the operational data is formatted to be inaccessible to the user of the automated chest compression device, the operational data is collected for use in troubleshooting a problem with the platform and/or gathering historic data regarding use of the platform, the operational data is formatted by the controller to be accessible by an authorized user, the number of clinical metrics is derived from at least a portion of the number of signals, and the number of clinical metrics is collected for use in a summary report accessible to a clinical user. The method may include receiving, by the controller, termination of the usage session, generating, by the controller, a session report for the usage session, where the session report includes a summary of the number of clinical metrics for the usage session, where the session report is configured to be accessible to the clinical user, and transferring, by the controller to a server or a portable computer readable medium, the session report.

In some implementations, the method includes identifying, by the controller, insertion of a connector for establishing a data link to a portable media device into a physical data connection port of the automated chest compression device, where transferring the session report includes transferring the session report via the data link.

In some implementations, the method includes transferring, by the controller to the portable media device via the data link, the operational data in an encrypted format.

In some implementations, the portable media device is a flash memory device.

In some implementations, the data link is a serial data link.

In some implementations, the platform includes a communication transmitter, and the method includes transmitting, by the controller on a periodic basis, newly accumulated operational data via the communication transmitter.

In some implementations, transferring the session report includes transferring the session report to the server via a wireless connection with a portable computing device.

In some implementations, the method includes receiving, by the controller via a data connection, authentication information for the authorized user, authenticating, by the controller, the authorized user with the authentication information, and transferring, via the data connection based at least in part on the authenticating, the operational data for review by the authorized user.

In some implementations, the authentication information includes a password or passcode.

In some implementations, transferring the session report includes transferring the session report in PDF format.

In one aspect, the present disclosure relates to a medical resuscitation system, including an accessory unit for assisting in medical treatment provision by a platform for delivery of mechanical chest compressions, the accessory unit including a housing including a communication port, a communication transmitter/receiver, a non-volatile memory, and processing circuitry configured to store, to the memory, a number of accessory metrics regarding functionality of the accessory unit, receive, via the communication transmitter/receiver, clinical metrics related to a treatment session including a number of chest compressions delivered by the platform, store, to the memory, the clinical metrics, establish a data connection between the communication transmitter/receiver and a communication receiver of a data integrator, after establishing the data connection, transfer, via the data connection, the clinical metrics and the accessory metrics to the data integrator, and after transferring the clinical metrics, maintain, on the memory, a copy of the clinical metrics as long-term data storage.

In some implementations, the communication transmitter/receiver is a wireless communication transmitter/receiver.

In some implementations, the wireless communication transmitter/receiver is a short-range wireless communication transmitter/receiver.

In some implementations, the accessory unit is configured to releasably couple to the platform.

In some implementations, the accessory unit is configured to releasably couple to the data integrator.

In some implementations, the accessory unit is a power unit and the data integrator is a docking unit including a charger for a battery of the power unit.

In some implementations, the number of accessory metrics includes at least one of a voltage, a temperature, a current, a state of charge, or an error status.

In some implementations, the accessory unit is a defibrillation unit.

In some implementations, the number of accessory metrics includes at least one of a current delivered, a physiologic waveform, a blood pressure, a device status, and an operational mode.

In some implementations, the accessory unit is a ventilator.

In some implementations, the first processing circuitry is configured to synchronize a clock time with processing circuitry of the platform, where a timeframe of a number of time stamps of the clinical metrics correspond to a timeframe of a number of time stamps of the accessory metrics due to the synchronizing.

In one aspect, the present disclosure relates to a medical resuscitation system, including a platform configured for releasable coupling to a patient for delivery of mechanical chest compressions, the platform including at least one sensor, each sensor for monitoring a respective aspect of at least one aspect of the delivery of the mechanical chest compressions, and a housing including a first communication means, first processing circuitry for controlling the delivery of the mechanical chest compressions, and receiving a number of signals from each sensor of the at least one sensor, and a first non-volatile memory. The first processing circuitry may be configured to store, to the first memory, session data including at least one of a) the number of signals or b) at least one device performance metric derived from the number of signals. The medical resuscitation system may include an accessory unit configured for assisting in providing treatment to the patient with the platform, the accessory unit including a housing including second processing circuitry, a second non-volatile memory, and a second communication means for communicating with the first processing circuitry of the platform. The second processing circuitry may be configured to store, to the second memory, a number of accessory unit metrics regarding functionality of the accessory unit, receive the session data via the second communication means, and store, to the second memory, the session data. The medical resuscitation system may include a data integrator including a housing including a third communication means for communicating with the second processing circuitry of the accessory unit, third processing circuitry, and a third non-volatile memory. The third processing circuitry may be configured to receive, via the third communication means, the session data and the number of accessory unit metrics, and store, to the third memory, the session data and the number of accessory unit metrics.

In some implementations, the data integrator includes a network communication port for communicating with a remote computing system, and the third processing circuitry is configured to establish a network connection with the remote computing system via the network communication port, and after establishing the network connection, transfer, to the remote computing system, the session data and the number of accessory unit metrics.

In some implementations, the medical resuscitation system includes the remote computing system, where the remote computing system is an analytics platform including a non-volatile network storage region, and fourth processing circuitry configured to store, to the network storage region, the session data and the number of accessory unit metrics.

In some implementations, the fourth processing circuitry is configured to link, within the network storage region based at least in part on a device identifier associated with the session data, the session data to historic session data, and analyze the session data and the historic session data to determine a number of historic usage metrics.

In some implementations, the third processing circuitry is configured to store, to the third memory, a number of data integrator metrics regarding functionality of the data integrator.

In some implementations, the data integrator includes a battery charger, and the number of data integrator metrics includes at least one of a battery performance metric, an error code, and a temperature.

In some implementations, the first communication means includes a wireless transmitter, the second communication means includes a wireless transmitter/receiver, and the third communication means includes a wireless receiver.

In some implementations, the session data further includes user interaction data including user interactions with the platform.

In some implementations, the user interaction data includes at least one of a compression mode change, a session pause, or a platform audio mute activation.

In some implementations, the platform includes a data communication port, and the first processing circuitry of the platform is configured to establish a data connection with a mobile computing device via the data communication port, and provide, to an application executing on the mobile computing device, at least a portion of the session data for presentation on a display of the mobile computing device.

In some implementations, the application is a training application for training a user to operate the platform.

In some implementations, the application is a help application for assisting a user in troubleshooting a problem with the platform.

In some implementations, the data integrator is a defibrillator, and the third communication means is a Wi-Fi transmitter/receiver.

In some implementations, the accessory unit is a portable computing device.

In one aspect, the present disclosure relates to a medical resuscitation system, including a platform configured for releasable coupling to a patient for delivery of mechanical chest compressions, the platform including at least one sensor, each sensor for monitoring a respective aspect of at least one aspect of the delivery of the mechanical chest compressions, and a housing including a non-volatile memory, a wireless communication transmitter, and processing circuitry configured to control the delivery of the mechanical chest compressions during a session of therapy delivery to the patient, receive, during the session, a number of signals from each sensor of the at least one sensor, store, to the memory, operational data including at least one of a) the number of signals or b) at least one device performance metric derived from the number of signals, where the operational data is collected for use in troubleshooting a problem with the platform and/or gathering historic data regarding use of the platform, and the operational data is formatted by the processing circuitry to be accessible by an authorized user, and a number of clinical metrics regarding the delivery of the mechanical chest compressions during the session, where the number of clinical metrics is derived from at least a portion of the number of signals, and the number of clinical metrics is collected for use in a summary report accessible to a clinical user, and transfer, via the wireless transmitter to a portable computing device, the number of clinical metrics.

In some implementations, the wireless transmitter is a Bluetooth transmitter.

In some implementations, the wireless transmitter is a Wi-Fi transmitter.

In some implementations, the operational data includes device status information.

In some implementations, the platform includes a wireless transmit control, and the processing circuitry is configured to receive a control signal indicative of user activation of the wireless transmit control, and, responsive to receiving the control signal, transfer the operational data via the wireless transmitter to the portable computing device.

In some implementations, transferring the operational data includes transferring the operational data further responsive to identifying the session has ended.

In some implementations, the session begins at powering on the platform, and the session ends at powering off the platform.

In some implementations, the number of clinical metrics is organized into the summary report at the portable computing device.

In some implementations, the summary report includes one or more of a compression rate, a compression ratio, or a compression count.

In some implementations, the medical resuscitation system includes a data integrator, where the data integrator includes a housing including second processing circuitry, a second non-volatile memory, and a wireless communication receiver. The second processing circuitry may be configured to receive, from the portable computing device via the wireless communication receiver, the operational data, and store, to the second memory, the operational data, and after the session, transfer, via the wireless transmitter to a portable computing device, the operational data.

In some implementations, the data integrator is a defibrillator.

In some implementations, the medical resuscitation system includes an accessory unit, where the accessory unit includes a housing including second processing circuitry, a second non-volatile memory, and a wireless communication receiver. The second processing circuitry may be configured to store, to the second memory, a number of accessory unit metrics regarding functionality of the accessory unit, receive, from the portable computing device via the wireless communication receiver, the operational data, and store, to the second memory, the operational data, and after the session, transfer, via the wireless transmitter to a portable computing device, the operational data.

In some implementations, the accessory unit is a defibrillator.

In one aspect, the present disclosure relates to a medical resuscitation system, including a platform configured for releasable coupling to a patient for delivery of mechanical chest compressions, the platform including at least one sensor, each sensor for monitoring a respective aspect of at least one aspect of the delivery of the mechanical chest compressions, and a housing including a non-volatile memory, and processing circuitry configured to control the delivery of the mechanical chest compressions during a session of therapy delivery to the patient, receive, during the session, a number of signals from each sensor of the at least one sensor, store, to the memory, operational data including at least one of a) the number of signals or b) at least one device performance metric derived from the number of signals, where the operational data is collected for use in troubleshooting a problem with the platform and/or gathering historic data regarding use of the platform, and the operational data is formatted by the processing circuitry to be accessible by an authorized user, and a number of clinical metrics regarding the delivery of the mechanical chest compressions during the session, where the number of clinical metrics is derived from at least a portion of the number of signals, and the number of clinical metrics is collected for use in a summary report accessible to a clinical user, and transfer, to a remote server, the number of clinical metrics, where the remote server organizes the number of clinical metrics into the summary report.

In some implementations, transferring the number of clinical metrics includes transferring to the remote server via a wired connection.

In some implementations, the housing includes an Ethernet port for providing the wired connection.

In some implementations, the number of clinical metrics is transferred periodically during the session.

In some implementations, the processing circuitry is configured to transfer, to a second remote server, the operational data.

In some implementations, the second remote server is different than the remote server.

In some implementations, transferring the operational data includes transferring the operational data after the session has ended.

In some implementations, the session begins at powering on the platform, and the session ends at powering off the platform.

In some implementations, the housing further includes a wireless transmitter, and transferring the operational data includes transferring the operational data via the wireless transmitter.

In some implementations, the wireless transmitter is one of a cellular transmitter or a Wi-Fi transmitter.

In some implementations, the platform includes a data transmit control, and the processing circuitry is further configured to receive a control signal indicative of user activation of the data transmit control, and responsive to receiving the control signal, transfer the operational data to an accessory unit or a data integrator.

In some implementations, the accessory unit or data integrator is a portable computing device.

In one aspect, the present disclosure relates to a method for managing an inventory of automated chest compression platforms at a central monitoring device, the method including receiving, at a computing system, at least one network or wireless communication including device information and operational information for each platform of a number of automated chest compression platforms, where the device information includes a device identifier, and the operational information includes at least one of a battery status, a component functionality status, an alert, a warning, or a failure condition, where the operational data includes i) at least a portion of a number of sensor signals collected by the platform and/or ii) a number of device performance metrics derived from the number of sensor signals, and the operational data is formatted to be inaccessible to a user of the platform, analyzing, by the computing system, the operational information for each platform of the number of automated chest compression platforms to determine at least one status indicator for each platform of at least a portion of the number of platforms, and generating, for presentation on a display device built into or in wired or wireless communication with the computing system, visual representations of one or more status indicators corresponding to each platform of the number of automated chest compression platforms along with identification of each respective platform based at least in part on the device identifier.

In some implementations, the method includes determining, by the computing system, one or more platforms of the number of automated chest compression platforms lacks delivery of device information and operational information within a threshold amount of time, where the one or more status indicators for each platform the one or more platforms lacking delivery within the threshold amount of time is represented by a visual representation of a communication failure.

In some implementations, the device information includes a software installation version, the method further including pushing, to one or more platforms of the number of platforms, an updated software installation version.

In some implementations, receiving the at least one network or wireless communication includes receiving a wireless communication from a data integrator in communication with at least a portion of the number of automated chest compression platforms, where the wireless communication includes device information and operational information for at least two platforms of the number of automated chest compression platforms.

In some implementations, the method includes receiving, at the computing system, one or more network or wireless communications including device information and operational information for each accessory unit of a number of accessory units, analyzing, by the computing system, the operational information for each accessory unit of the number of accessory units to determine at least one status indicator for each accessory unit of the number of the accessory units, and generating, for presentation on the display device, visual representations of one or more status indicators corresponding to each accessory unit of the number of accessory units along with identification of each respective accessory unit based on the device identifier.

In some implementations, the one or more network or wireless communications includes the at least one wireless communication, containing device information and operational information for both one or more accessory units and one or more device platforms.

In some implementations, the method includes receiving, at the computing system, one or more network or wireless communications including device information and operational information for each data integrator of a number of data integrators, analyzing, by the computing system, the operational information for each data integrator of the number of data integrators to determine at least one status indicator for each data integrator of the number of the data integrators, and generating, for presentation on the display device, visual representations of one or more status indicators corresponding to each data integrator of the number of data integrators along with identification of each respective data integrator based on the device identifier.

In some implementations, the computing system is a centrally located computing device disposed in a facility housing the number of automated chest compression device platforms.

In some implementations, the wireless communication is a Wi-Fi communication.

In some implementations, the computing system is a network-based system accessible via the Internet.

In some implementations, the network communication is initiated by a data integrator via an Ethernet connection.

In some implementations, the method further includes automatically issuing, by the computing system, at least one command to trigger a self-test routine in at least a portion of the number of automated chest compression platforms.

In some implementations, issuing the at least one command includes issuing the at least one command to each platform of the number of automated chest compression platforms having operational information indicative of a potential problem.

In some implementations, the identification of each respective platform includes a location of the respective platform.

In some implementations, the location of the respective platform includes a most recent location as identified by positioning data provided by the platform from a GPS receiver of the platform.

In some implementations, the method includes identifying the status indicator of at least one platform corresponds to a high priority status, and responsive to the determining, issuing a communication to at least one administrator account.

In some implementations, issuing the communication includes sending a text message to a telephone number associated with each account of the at least one administrator account.

In some implementations, method includes identifying the status indicator of at least one platform corresponds to a need for device maintenance, and responsive to the determining, issuing a communication to a customer service account of a manufacturer of the at least one platform.

In some implementations, a portion of the operational data is collected for use in troubleshooting a problem with the platform, where the portion of the operational data is formatted by the controller to be accessible by an authorized user of the customer service account.

The forgoing general description of the illustrative implementations and the following detailed description thereof are merely exemplary aspects of the teachings of this disclosure, and are not restrictive.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. Where applicable, some or all features may not be illustrated to assist in the description of underlying features. In the drawings.

DETAILED DESCRIPTION OF ILLUSTRATIVE EMBODIMENTS

Figure 1A:
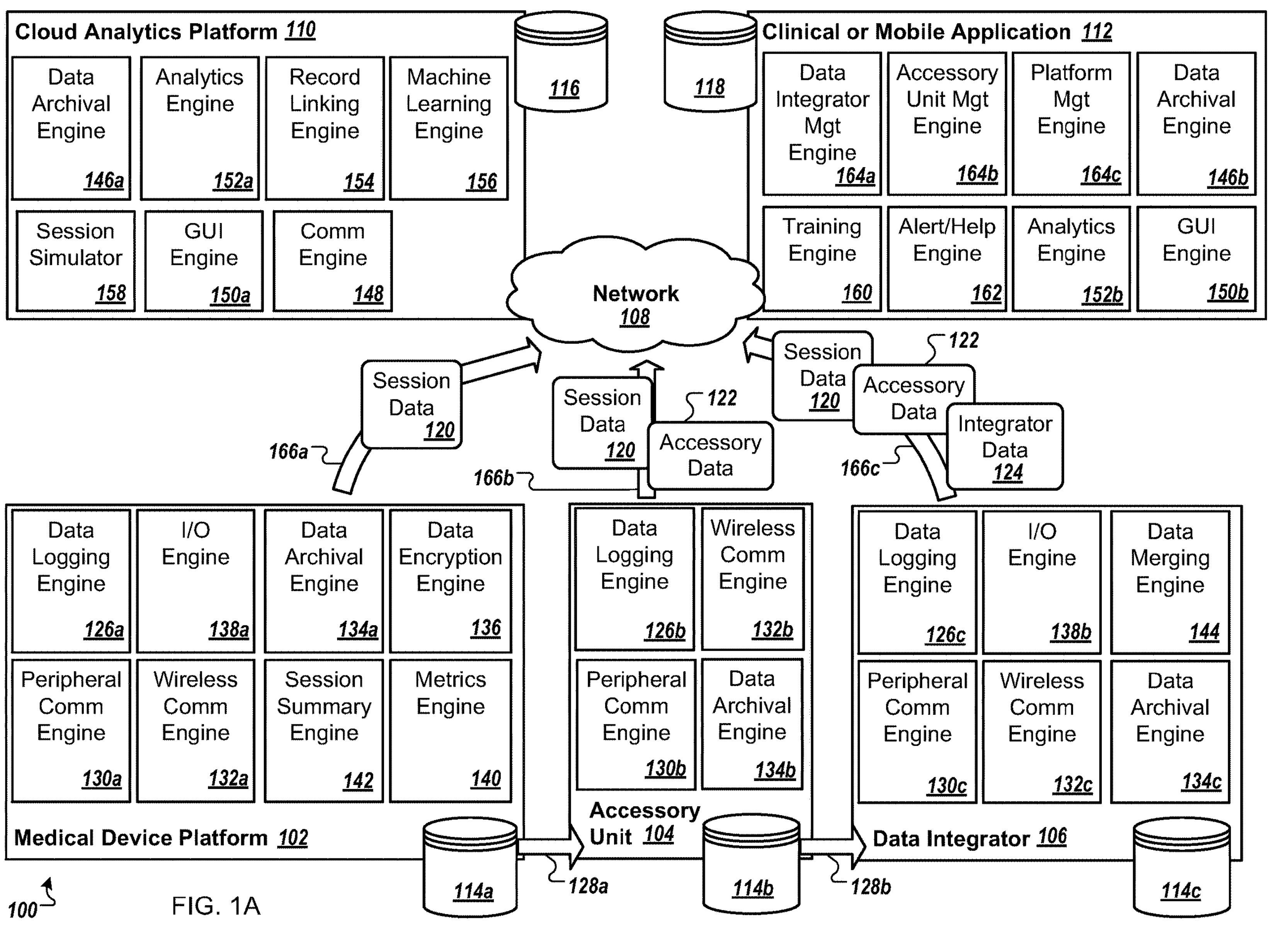
FIG. 1A illustrates an example environment for securely sharing data generated by a set of devices within a medical resuscitation system.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Further, it is intended that embodiments of the disclosed subject matter cover modifications and variations thereof.

It must be noted that, as used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "about," "proximate," "minor variation," and similar terms generally refer to ranges that include the identified value within a margin of 20%, 10% or preferably 5% in certain embodiments, and any values therebetween.

All of the functionalities described in connection with one embodiment are intended to be applicable to the additional embodiments described below except where expressly stated or where the feature or function is incompatible with the additional embodiments. For example, where a given feature or function is expressly described in connection with one embodiment but not expressly mentioned in connection with an alternative embodiment, it should be understood that the inventors intend that that feature or function may be deployed, utilized or implemented in connection with the alternative embodiment unless the feature or function is incompatible with the alternative embodiment.

Example Environment for Secure Data Sharing

Mechanical compression devices may include software commands that include different functional modes or delivery cycles based upon parameters collected by the device (e.g., via one or more sensors) and/or provided to the device (e.g., via a user interface). For example, the force, depth, rate, duty cycle, or other clinical performance parameters of the chest compressions may be adjusted, automatically or via user input, based on the size, stiffness or age of the patient being treated. Additionally, mechanical compression devices may monitor operational parameters and collect device operational data such as, in some examples, motor temperature, operational voltages, currents, run time, failure modes, and/or service or system maintenance related warnings or alerts of the chest compression device. Although the mechanical compression devices are at least temporarily collecting and applying this data during a treatment session, there is a need for mechanical compression devices to collect a comprehensive data set and distribute useful data and metrics from the mechanical compression device. In sharing the parameters or data, not all the data is relevant to all viewers of the shared information. Instead, it is desired to share differing sets of data appropriate to various types of audiences, such as a clinician audience and a technician audience. Without reducing the amount of data, for example, excess information may distract a clinician to the degree that an incorrect diagnosis may be made, or incorrect treatment given to the patient. Therefore, a clinician, such as an emergency responder, physician, or clinical supervisor would benefit from straightforward, easy to digest clinical metrics that assist in swiftly making patient treatment decisions during a therapy session or that allow for an efficient and clear post treatment session review to assist in improving future patient care and treatment delivery. Conversely, a technician, such as a customer support technician, may benefit from detailed device performance metrics and device operational data to diagnose problems with mechanical compression devices after delivery to customers.

Further, although mechanical compression devices may generate data, there is a need for integrating this data with data and metrics collected by other medical devices that contribute to, or operate in coordination with, the mechanical compression device. In a particular illustration, there is a need for integrating data and metrics collected and generated by a mechanical chest compression device with data and metrics collected and generated by a defibrillator device providing treatment in synchronization with the mechanical chest compression device. The integrated clinical data and metrics, for example, may provide clinicians with a comprehensive view of therapy delivered during a treatment session. Similarly, the integrated operational data and device performance metrics, in another example, may provide a technician such as a research and development engineer with a more holistic picture of the performance of the mechanical chest compression device within the treatment setting while interoperating with therapy provided by the defibrillator.

As the control of mechanical compression devices becomes more intelligent and specialized, there is a growing desire to collect and/or distribute data generated during usage of the device for later application as well. While in the field of other data-collecting devices, such as Internet of Things (TOT) devices, the collection of metrics and operating data is straightforward, in the emergency health treatment environment, factors such as patient data privacy, interactions between wireless transmissions and hospital equipment, and battery power preservation limit opportunities for transferring information for long term collection and later review. Thus, there is a need to secure stored data, manage the transmission data, and enable eventual off-site collection of the data. Collected data from a single mechanical compression device, for example, may be used to later evaluate or reproduce actions that occurred during a treatment session. Collected data from a group of mechanical compression devices, in another example, can provide research and development engineers with a better understanding of the usage scenarios and needs of customers, leading to insights in better developing both future software release versions and the next generation of mechanical compression devices.

The inventors have developed novel systems, methods, and a platform environment for secure data collection and sharing that meet several needs in the industry, including those described above. The present disclosure relates to systems, methods, and environments for data collection and secure data sharing during and/or subsequent to delivery of automated chest compressions to a patient by an automated chest compression device within a medical resuscitation system. Turning to FIG. 1A, in some implementations, an example environment 100 for secure data sharing includes a medical resuscitation system with a set of devices for use in providing resuscitation treatment to a patient. The system may include at least two devices designed to coordinate in providing the treatment to the patient. The devices, in the illustrated example, may include a medical device platform 102, such as an automated chest compression platform, an accessory unit 104, and a data integrator 106. The devices 102, 104, and 106 of the medical resuscitation system may be co-located at a treatment delivery site, such as a hospital, medical clinic, or ambulance. In other implementations, one or more of the devices, such as the data integrator 106, may be added to the system at some point during delivery of resuscitation therapy or subsequent to delivery of therapy. Conversely, one or both of the devices 104 and 106 may be removed from co-location during or subsequent to delivery of therapy. The devices may be configured for data communication in a wired or wireless manner for transferring information between certain devices 102, 104, and/or 106 of the system during and/or subsequent to delivery of therapy.

In some implementations, one or more of the devices 102, 104, 106 are also configured to communicate with a cloud analytics platform 110 and/or a clinical or mobile application 112 via a network 108. The network 108, in some examples, may be a Wi-Fi network, other short-range wireless communication network or near field communication (NFC) network, local area network (LAN), wide area network (WAN), or the Internet. In some embodiments, different ones of the devices 102, 104, and 106 may be configured to communicate over a different type of network 108. In an illustrative example, the platform 102 may be configured to communicate via a short-range wireless network with the accessory unit and/or data integrator 106, while the data integrator 106 is configured to communicate via a Wi-Fi network or the Internet (e.g., via an Ethernet connection). Example configurations are described in greater detail below, for example in relation to FIGS. 6A through 6C. In some implementations, one or more of the devices 102, 104, 106 are configured to transmit data via a short-range wireless communication transmitter, e.g. a Bluetooth beacon, to a receiver.

The devices of the medical resuscitation system, in some implementations, include the automated chest compression platform 102, one or more accessory units 104 for coordinating in providing resuscitation treatment to the patient and/or for supporting the functionality of the platform 102, and one or more data integrator units 106 for gathering data from other devices in the medical resuscitation system and for combining the data (e.g., merging data records) and/or supplying the data to an external computing system for combining. The accessory unit 104, in some examples, may be a rechargeable battery unit, e.g., a portable battery or plug-in battery, a defibrillation unit, a ventilation unit, and/or a portable computing device (e.g., handheld computing device such as a cellular phone, smart phone, tablet computer, or other portable smart screen device) for supplying a graphical user interface to a user during operation of the automated chest compression platform 102. The accessory unit 104, in some embodiments, is designed for physical coupling to the medical device platform 102. In some embodiments, the accessory unit 104 is designed for wireless coordination with the medical device platform 102. The accessory unit, in other embodiments, is designed for tethered (e.g., wired) coordination with the medical device platform 102. The data integrator 106, in some examples, may be a defibrillation unit, a ventilation unit, a portable (e.g., tablet, etc.) computing device, a battery charger, and/or an accessory docking unit. In some embodiments, the data integrator 106 is designed for physical coupling to the medical device platform 102 and/or the accessory unit 104. In some embodiments, the data integrator 106 is designed for wireless coordination with the medical device platform 102 and/or the accessory unit 104. The data integrator 106, in other embodiments, is designed for tethered (e.g., wired) communication with the medical device platform 102 and/or the accessory unit 104.

Each of the devices 102, 104, and 106, in some implementations, is configured to collect data regarding its performance. For example, the medical device platform 102 includes a data logging engine 126*a* for logging session data 120 during a treatment session with a patient and a data archival engine 134*a* for collecting the session data 120 in a non-volatile memory 114*a*. The session data 120, in some embodiments, includes operational data, such as device performance metrics, regarding device operation during or outside the time of a treatment session, and/or clinical data, such as clinical metrics, regarding treatment provided via the medical device platform 102. The accessory unit 104, similarly, may include a data logging engine 126*b* for collecting accessory data 122 and a data archival engine 134*b* for storing the accessory data 122 in a non-volatile memory 114*b*. Further, the data integrator may include a data logging engine 126*c* for collecting integrator data 124 and a data archival engine 134*c* for storing the integrator 124 in a non-volatile memory 114*c*. Examples of session data 120, accessory data 122, and integrator data 124 are described below, for example in relation to FIGS. 5A through 5E. The data archival engines 134*a*, 134*b*, and/or 134*c* may store at least a portion of the data in a protected format, such as an encrypted format or a proprietary format, to protect the data from access and review by anyone not authorized to access such data. For example, turning to FIG. 5A, an initial belt position 524*d*, a belt travel distance 524*e*, linear or shaft encoder readings 522*a*, accelerometer readings 522*b*, pressure sensor readings 522*c*, and load sensor readings 522*d* may be protected as authorized operational data and device performance metrics.

In some implementations, each of the devices 102, 104, and 106 is configured to transfer data to another of the medical devices 102, 104, and 106 of the medical resuscitation system. For example, the medical device platform 102 may transfer session data 120 from the non-volatile memory 114*a* to the accessory unit 104 via a data communication connection 128*a* between the medical device platform 102 and the accessory unit 104. For example, a peripheral communication engine 130*a* may establish a direct (e.g., wired) communication link 128*a* with the accessory unit 104 and/or a wireless communication engine 132*a* may establish a wireless communication link 128*a* with the accessory unit 104 to transfer session data 120 to the accessory unit 104. Conversely, the accessory unit 104 may establish the communication link 128*a* with the medical device platform 102 (e.g., via a wireless communication engine 132*b* or peripheral communication engine 130*b*) to request the session data 120 from the medical device platform. Further, in some embodiments, the medical device platform 102 may send session operational data (not illustrated) to the accessory unit 104 or vice-versa. For example, the medical device platform 102 and the accessory unit 104 may share information, such as synchronizing timestamps, coordinating delivery of therapy, and/or coordinating operational modes. In illustration, the metrics engine 140 of the medical device platform 102 may estimate physiological data regarding the patient, such as chest circumference and supply the physiological data to a defibrillator type accessory unit 104 for use in calibrating defibrillation therapy.

In other embodiments (not illustrated), the medical device platform 102 may be further configured to transfer the session data 120 to the accessory unit 104 via a wired or wireless data communication connection. In turn, the accessory unit 104 may be configured to transfer the session data 120 and/or accessory data 122 via a data communication link 128*b* to the data integrator 106. For example, the peripheral communication engine 130*b* may establish a direct (e.g., wired) communication link 128*b* with the data integrator 106 and/or the wireless communication engine 132*b* may establish a wireless communication link 128*b* with the data integrator 106 to transfer session data 120 to the data integrator 106. To establish the data communication link 128*b*, for example, the peripheral communication engine 130*c* or wireless communication engine 132*c* may complete the communication link 128*b* with the accessory unit 104. Conversely, the data integrator 106 may establish the communication link 128*b* (via the peripheral communication engine 130*c* or wireless communication engine 132*c*) with the accessory unit 104 to request the session data 120 and/or accessory data 122 from the accessory unit 104.

Figure 1B:
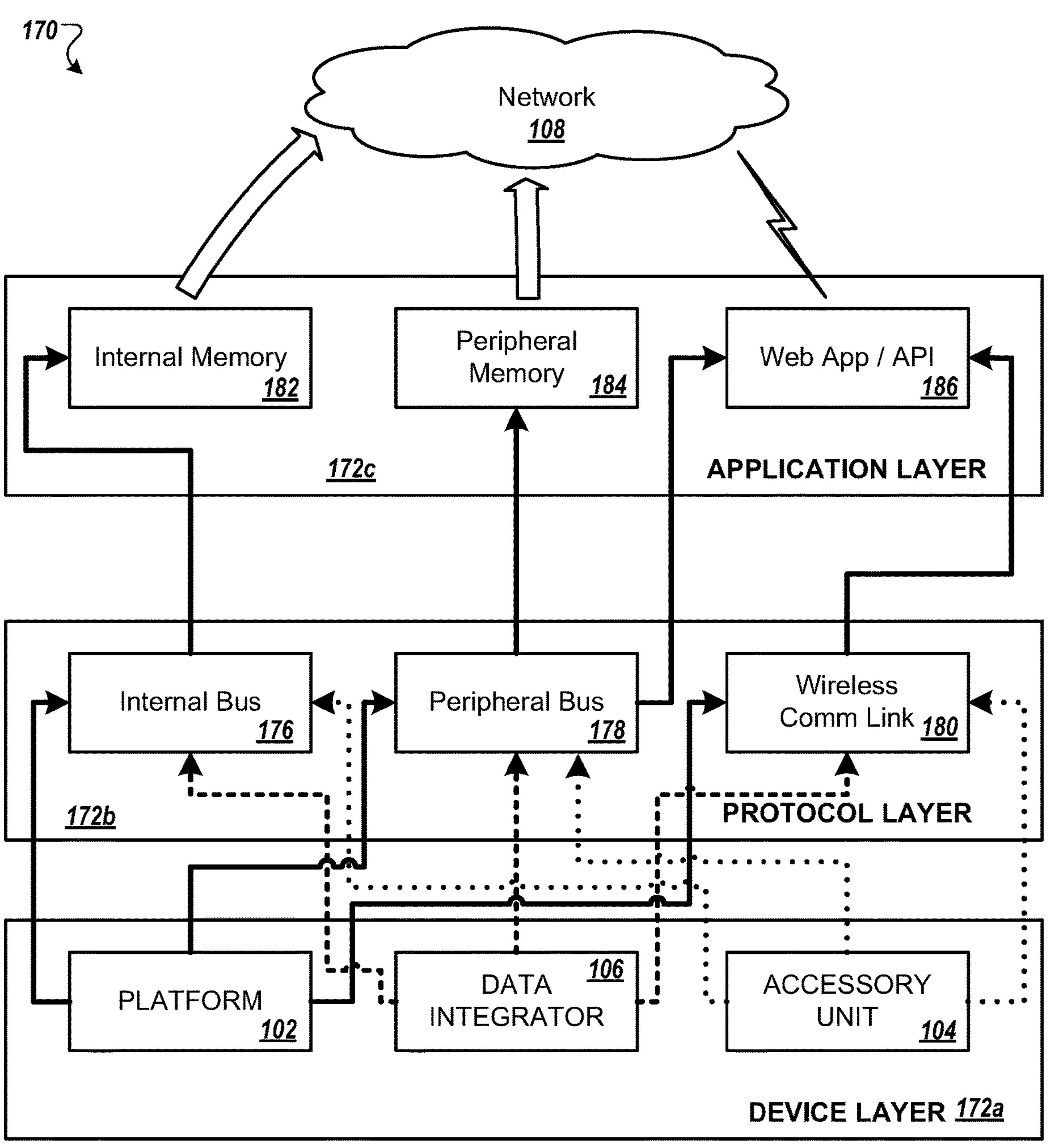
FIG. 1B illustrates an example network communication stack for enabling secure sharing of data generated by a set of devices within a medical resuscitation system.

In an illustrative example, turning to FIG. 1B, in some implementations, an example network communication stack 170 for enabling secure sharing of data generated by a set of devices 102, 104, 106 within a medical resuscitation system includes a device layer 172*a*, a protocol layer 172*b*, and an application layer 172*c*. The device layer 172*a* includes the medical device platform 102, the data integrator 106 and the accessory unit 104. Each of the devices 102, 104, and 106 include a number of possible communication paths through a protocol layer 172*b*, including a path via an internal bus 176, a peripheral bus 178, and/or a wireless communication link 180. These paths, in turn, connect to application layer 172*c* memory and/or application access, such as to an internal memory 182 (e.g., the non-volatile memory 114*a*, 114*b*, or 114*c* of FIG. 1A), a peripheral memory 184, and/or a web application and/or application programming interface (API) access 186.

As illustrated, the platform 102 may connect, via its internal bus 176, to its internal memory 182 (e.g., the non-volatile memory 114*a*). Further, in some embodiments, the medical device platform 102 connects, via the peripheral bus 178, to the peripheral memory 184. For example, the medical device platform 102 may communicate with the peripheral memory 184 of a USB-enabled device such as a portable Flash memory or a USB-tethered handheld computing device, via the peripheral bus 178. In another example, the medical device platform 102 may communicate with the peripheral memory 114*b* of the accessory unit 104 (e.g., via the communication link 128*a*, as illustrated in FIG. 1A) or the peripheral memory 114*c* of the data integrator 106. The peripheral bus 178, in an illustrative example, may be a serial bus connection established by physically coupling the medical device platform 102 to the accessory unit 104. In another example, the medical device platform 102 may be physically tethered via the peripheral bus 178 to a network-enabled computing device such as a local server, handheld computing device, or laptop device. Further to this example, the medical device platform 102 may be physically connected to the network 108 via an ethernet connection 166*a* to a local network hub, router, or server device. Additionally, in some embodiments, the medical device platform 102 communicates, via the wireless communication link 180 with a local device or remote device. For example, the medical device platform 102 may communicate with a server or computing device, such as the cloud analytics platform 110 or the clinical or mobile application 112 of FIG. 1A, via a wireless connection 166*a* to the network 108. The wireless connection, for example, may be a Wi-Fi connection or a cellular data connection. In another example, the medical device platform 108 may communicate with the accessory unit 104 via a wireless connection established through the communication link 128*a* and/or with the data integrator 106. The wireless connection, in this example, may be a short-range wireless connection such as a Wi-Fi, Bluetooth, Zigbee, optical, or other radio frequency (RF) connection including networks thereof. In another example, the medical device platform 108 may communicate with the accessory unit 104 via a dynamically reconfigurable and secure mesh networking protocol such as ZigBee. Zigbee is a specification for a suite of high-level communication protocols used to create personal area networks built from small, low-power digital radios, and is based on an IEEE802.15.4 standard.

Turning to the accessory unit 104, the device 104 may connect, via its internal bus 176, to its internal memory 182 (e.g., the non-volatile memory 114*b*). Further, in some embodiments, the accessory unit 104 connects, via the peripheral bus 178, to the peripheral memory 184. For example, the accessory unit 104 may communicate with the peripheral memory 114*a* of the medical device platform 102 (e.g., via the communication link 128*a*, as illustrated in FIG. 1A) or the peripheral memory 114*c* of the data integrator 106 (e.g., via the communication link 128*b*, as illustrated in FIG. 1A). The peripheral bus 178, in an illustrative example, may be a serial bus connection established by physically coupling the accessory unit 104 to the medical device platform 102 or to the data integrator 106. In another example, the accessory unit 104 may be physically tethered via the peripheral bus 178 to a network-enabled computing device such as a local server, handheld computing device, or laptop device. Further to this example, accessory unit 104 may be physically connected to the network 108 via an ethernet connection 166*b* to a local network hub, router, or server device, as illustrated in FIG. 1A. Additionally, in some embodiments, the accessory unit 104 communicates, via the wireless communication link 180 with a local device or remote device. For example, the accessory unit 104 may communicate with a server or computing device, such as the cloud analytics platform 110 or the clinical or mobile application 112 of FIG. 1A, via a wireless connection 166*b* to the network 108. The wireless connection, for example, may be a Wi-Fi connection or a cellular data connection. In another example, the accessory unit 104 may communicate with the medical device platform 102 via a wireless connection established through the communication link 128*a* and/or with the data integrator 106 via a wireless connection established through the communication link 128*b*. The wireless connection, in this example, may be a short-range wireless connection such as a Bluetooth connection, Zigbee connection, optical connection, or radio frequency (RF) connection. Alternatively, the accessory unit 104 may be configured to communicate with one or both of the medical device platform 102 and the data integrator 106 via a Wi-Fi connection.

Turning to the data integrator 106, the data integrator 106 may connect, via its internal bus 176, to its internal memory 182 (e.g., the non-volatile memory 114*c*). Further, in some embodiments, the data integrator 106 connects, via the peripheral bus 178, to the peripheral memory 184. For example, the data integrator 106 may communicate with the peripheral memory 184 of a USB-enabled device such as a portable Flash memory or a USB-tethered handheld computing device, via the peripheral bus 178. In another example, the data integrator 106 may communicate with the peripheral memory 114*b* of the accessory unit 104 (e.g., via the communication link 128*b*, as illustrated in FIG. 1A) or the peripheral memory 114*a* of the medical device platform 102. The peripheral bus 178, in an illustrative example, may be a serial bus connection established by physically coupling the data integrator 106 to the accessory unit 104. In another example, the data integrator 106 may be physically tethered via the peripheral bus 178 to a network-enabled computing device such as a local server, handheld computing device, or laptop device. Further to this example, the data integrator 106 may be physically connected to the network 108 via an ethernet connection 166*c* to a local network hub, router, or server device, as illustrated in FIG. 1A. Additionally, in some embodiments, the data integrator 106 communicates, via the wireless communication link 180 with a local device or remote device. For example, the data integrator 106 may communicate with a server or computing device, such as the cloud analytics platform 110 or the clinical or mobile application 112 of FIG. 1A, via a wireless connection 166*c* to the network 108. The wireless connection, for example, may be a Wi-Fi connection or a cellular data connection. In another example, the data integrator 106 may communicate with the accessory unit 104 via a wireless connection established through the communication link 128*b* and/or with the medical device platform 102. The wireless connection, in this example, may be a short-range wireless connection such as a Bluetooth connection, Zigbee connection, infrared (IR) connection, or radio frequency (RF) connection. Alternatively, the data integrator 106 may be configured to communicate with one or both of the accessory unit 104 and the medical device platform 102 via a Wi-Fi connection (e.g., via a Wi-Fi network 108, using the network connections 166, as illustrated in FIG. 1A).

The data may be transferred, in some implementations, in an encrypted or proprietary format to protect the data from access and review from anyone not authorized or credentialed to inspect such data. For example, the medical device platform 102 includes a data encryption engine 136 for encrypting at least a portion of the session data 120. The encrypted data, in one example, may include patient confidential information such as patient identifying information and/or patient demographic information. In another example, the encrypted data may include data collected on behalf of a manufacturer of the medical device platform 102 for troubleshooting problems or error conditions in the medical device platform 102 and/or for monitoring usage of medical device platforms and various deployments. Such usage scenarios are described in greater detail below, for example, in relation to FIGS. 2A-2D, 3A, and 3B.

In some implementations, the session data 120 transferred to the data integrator 106 is merged with the accessory data 122 and/or the integrator data 124 by a data merging engine 144 of the data integrator 106. The data merging engine 144, for example, may merge records included in the session data 120 with records of the accessory data 122 and/or the integrator data 124 based upon time stamps associated with each of the records. In another example, the records of the data 120, 122, and/or 124 may be merged based upon event markers within the data 120, 122, and/or 124. Event markers may include one or more events during therapy delivery such as, in some examples, a time of session pause, a time of session resumption, a stop, pause or start in compressions event, power on or off, battery removal/replacement, actuation of a latching or locking mechanism holding the battery in position, belt end or belt tab insertion/removal (e.g., left or right), replacement, or misalignment (e.g., in relation to the medical device platform 102), and/or a belt guard attachment/detachment, replacement, or misalignment (e.g., in relation to the medical device platform 102). In the circumstance of a defibrillator-type data integrator 106, the events may include delivery of shock therapy, start of a defibrillation cycle, a length of time of charging prior to delivery of shock therapy, a length of time of EKG assessment, and/or an EKG change event or heart rate change event captured by sensors of the defibrillator-type data integrator 106. In further examples, the events may include errors and/or alerts such as over-temperature, over-current, or low battery in the platform 102, accessory unit 104, or data integrator 106 and/or, more generally, any error or alert leading to a stop or pause in treatment. The events may include a ventilation delivery event by a ventilator type accessory unit 104. Further, regarding the medical device platform 102 or defibrillator type data integrator 106, events may include a patient not found event. The event markers, in an illustrative example, may include a ventilator event marker in the accessory data 122 corresponding to breathing biometric data collected by one or more sensors of a defibrillator-type data integrator 106 and/or a pause event in delivery of compressions by the medical device platform 102. In another illustration, a defibrillator event marker in the accessory data 122 may correspond to heart rate biometric data and/or EKG biometric data collected by one or more sensors of the defibrillator-type data integrator 106.

In some implementations, the medical device platform is configured to collect raw data and perform analysis on the data to derive metrics and/or summaries of information for inclusion in the session data 120. For example, an input/output (I/O) engine 138*a* may gather information from a number of sensors built into the medical device platform 102 and/or in communication with the medical device platform 102. The raw sensor data may be combined by a metrics engine 140, in some examples, to generate clinical metrics regarding aspects of the treatment session (e.g., for use by clinical personnel) and/or device performance metrics regarding performance of the medical device platform 102 (e.g., for use by a device manufacturer). Further, the medical device platform 102 may include a session summary engine 142 to generate summary data regarding the treatment session. The session summary engine 142, for example, may prepare a summary report for review by a clinical user such as, in some examples, a medical professional, treatment supervisor, medical facility administrator, student or staff instructor, or emergency medical responder.

In some implementations, the medical device platform 102 is configured to transfer at least a portion of the session data 120, such as the clinical metrics, device performance metrics, and/or summary report, to the clinical user via a peripheral communication link (not illustrated). For example, the summary report may be provided to a user via a wired connection such as a universal serial bus (USB) connection to a portable data collection device. In an illustrative example, the peripheral communication engine 130*a* may establish a USB data transfer connection to a flash drive, tablet computer, or other handheld device upon connection of the device to the medical device platform 102 via a USB port of the medical device platform 102. Such data transfers are described in further detail in relation to FIGS. 2A and 3A.

In some implementations, the medical device platform 102, the accessory unit 104, and or the data integrator 106 is configured to provide the session data 120 (and, optionally, the accessory data 122 and/or the integrator data 124) to the cloud analytics platform 110 and/or the clinical mobile application 112 via the network 108. The session data 120 may be transferred to the network 108 during treatment and/or after a treatment session has ended. The session data 120, in an illustrative example, may be transferred via a wired connection during a treatment session, but via a wireless connection only after the session has ended to avoid communication conflicts or signal disruption with other medical devices within the treatment setting. The communications, for example, may be enabled through data communication paths as described above in relation to FIG. 1B.

The GUI engines 150*a*, 150*b* of the cloud analytics platform 110 and/or the clinical or mobile application 112, in some implementations, are configured to display only some of the session data 120 depending on an identification of the end user of the information. For example, a user logged with a clinical user account, such as a physician, would be provided viewing privileges for clinical data and/or clinical metrics, while a user logged in with an authorized user account, such as a service technician, would be denied viewing privileges for at least a portion of the clinical data and/or clinical metrics (e.g., including any HIPAA-protected patient identifying information). Instead, the authorized user may be provided privileges to access operational data and/or device performance metrics which lacks any patient identifying information.

In some implementations, the cloud analytics platform 110 includes a data archival engine 146*a* for archiving session data 120, accessory data 122, and/or integrator data 124 in a data store 116. The cloud analytics platform 110, for example, may be maintained by a manufacturer of the medical device platform 102 to gather information regarding the functionality of the medical device platform 102 and/or to troubleshoot problems occurring with the medical device platform 102. The cloud analytics platform 110, for example, may be accessible by authorized users that have been granted access to device operational data and metrics by the device manufacturer. The operational data, for example, may include data collected on behalf of a manufacturer of the medical device platform 102 for troubleshooting problems or error conditions in the medical device platform 102 and/or for monitoring usage of medical device platforms and various deployments. A communications engine 148 of the cloud analytics platform 110, for example, may manage access to the cloud analytics platform 110. Users may be granted access to the information stored in the data store 116, for example, via password access, biometric access, or other security access to the cloud analytics platform 110. Access may be granted, for example, via user interaction with the cloud analytics platform 110 via a graphical user interface (GUI) engine 150*a*.

The cloud analytics platform 110, in some implementations, includes an analytics engine 152*a* for analyzing the session data 120, accessory data 122, and/or integrator data 124. The analytics engine 152*a*, for example, may generate higher level metrics out of raw data, such as the metrics generated by the metrics engine 140 of the medical device platform 102. The analytics engine 152*a*, for example, may generate metrics based upon raw data supplied in the accessory data 122 and/or the integrator data 124. In a further example, the analytics engine 152*a* may generate merged metrics using merged records provided by the data integrator 106 (e.g., merged using the data merging engine 144).

In some implementations, if the cloud analytics platform 110 has not obtained merged records, the cloud analytics platform 110 merges records using a record linking engine 154. Further, the record linking engine 154, in some embodiments, is configured to link session data 120, accessory data 122, and/or integrator data 124 obtained from the same device (e.g., the same platform 102, accessory unit 104, and/or data integrator 106) to archive (e.g., by the data archival engine 146*a*) collected data over time in the data store 116. The record linking engine 154, for example, may link records based upon device identifiers supplied to the cloud analytics platform 110 in the session data 120, the accessory data 122, and/or the integrator data 124.

In some implementations, the cloud analytics platform 110 includes a machine learning engine 156 to analyze the archived records collected over time and/or from various devices deployed at various locations. The machine learning engine 156 may include a number of machine learning features, each feature designed to discover a different type of information from the same or similar sets of records. The machine learning engine 156, further, may include machine learning features for various types of devices, such as, in some examples, automated chest compression platforms, defibrillators, rechargeable battery units, ventilators, and/or charging units.

The archived records, in some embodiments, are analyzed to identify upcoming service requirements or symptoms of a potential problem in a particular medical device. For example, the machine learning engine 156 may analyze archived records to identify devices exhibiting behavior associated with a clogged filter, devices having batteries that are nearing a failure stage, and/or devices that are exhibiting unusual power consumption behaviors. For example, service personnel and/or device owners/operators may be alerted to the anticipated service issue to ensure minimal downtime in returning the medical device to an operational state.

In some embodiments, the archived records are analyzed to identify a number of typical workflows regarding the operation of the medical device platform in the field. For example, a frequency of use of each device, a set up time between powering on the device and delivering chest compressions to a patient, and/or a movement of device in service (tilt, roll, inclination, pitch, acceleration, etc.) can inform the manufacturer of real life usage circumstances in treatment facilities, ambulances, and hospitals.

The cloud analytics platform, in some implementations, includes a session simulator 158 to reproduce or simulate a series of events that occurred during a treatment session. The session simulator 158, for example, may analyze operational data to trace user inputs to the medical device platform over time, compression delivery of the device over time, and operational mode changes of the device over time, etc., to reproduce a usage behavior that lead to an error condition or warning. The session simulator 158 may further automatically program a test medical device platform to perform the particular series of operations in an effort to duplicate the error or warning condition.

Turning to the clinical or mobile application 112, in some implementations, session data 120, accessory data 122, and/or integrator data 124 are received by the clinical or mobile application 112 via the network 108 and stored in a data store 118 by a data archival engine 146*b* (e.g., similar to the data archival engine 146*a* of the cloud analytics platform 110). The clinical or mobile application 112 may be executing on a computing device such as a laptop computer, tablet computer, or server. A graphical user interface (GUI) engine 150*b* of the clinical or mobile application 112 may provide a user interface to an end user, in some examples, via a browser, device-executed application, or network portal. In other embodiments (not illustrated), aspects of the clinical or mobile application 112 may be executing as part of a display interface of one of the medical device platform 102, the accessory unit 104, or the data integrator 106.

The archived data, in some implementations, is analyzed by an analytics engine 152*b* to derive clinical metrics related to an ongoing or ended treatment session. In the circumstance of an ongoing treatment session, in some embodiments, the clinical or mobile application 122 may present analytics data to an end user via a display of a device executing the clinical or mobile application 112, as presented by the GUI engine 150*b*. Additionally or alternatively, the analytics data presented to the end user may include metrics generated by the metrics engine 140 of the medical device platform 102. The end user display, in some embodiments, provides real time or near real time clinical metrics for review by a clinical user during the treatment session.

Further, in some implementations, the real time or near real time information provided in the end user display may include alerts, error conditions, and/or user support in dealing with problems occurring during use of the medical device platform 102 and/or the medical resuscitation system. For example, an alert and/or help engine 162 may supply information related to alert and/or error conditions provided in the session data 120, accessory data 122, and/or integrator data 124. The alert and/or help engine 162, for example, may receive an alert or error code and translate the alert or error code into a brief explanation for review by a clinical user during use of the medical device platform 102 or resuscitation system. The alert and/or help engine 162 may further provide suggestions to the user via the GUI engine 150*b* for how to respond to the alert or error to swiftly troubleshoot or overcome the problem.

In some implementations, the real time or near real time information includes live and/or remote medical assistance. In the circumstance of help regarding the setup and operation of the medical device platform 102, for example, operational data may be uploaded from the platform 102, accessory unit 104, and/or data integrator 106 to a network accessible location to provide the alerts and/or error conditions to a live technician (or, alternatively or additionally, an artificial intelligence help support bot) for supporting the clinician user in using the medical device platform 102. In an illustrative example, at least a portion of the information presented to the clinical user via the GUI engine 150*b* of the clinical or mobile application 112 may be further presented to remotely located technical assistance personnel for providing service beyond a simple help menu support provided by the alert/help engine 162 as described above. The clinical user may be provided with voice communications with the technical assistance personnel, for example via the accessory unit 104 or data integrator 106, to talk through an issue using a microphone I/O interface. For example, the clinical user may ask "how do I ensure the piston stays in proper position?" or "how do I set up the device to interoperate with the defibrillator?" The technical assistance personnel, conversely, may be provided with voice communications via a speaker I/O interface to respond to the clinical user with suggestions or requests for further information.

In some embodiments, the technical assistance personnel representative is supplied with additional operational data and/or device performance metrics for isolating a problem occurring with the device. The operational data and/or device performance metrics, in some examples, may include one or more temperatures, voltages, currents, sensor readings, and/or metrics derived from the same. For example, based on a current tilt angle of the device accessed from a gyroscope sensor or accelerometer sensor and uploaded via the network 108 as session data 120, the technical personnel representative may suggest (e.g., verbally through a speaker interface of the accessory unit 104 or data integrator 106, visually via a command line interface of a tablet computer style accessory unit 104 or data integrator 106, etc.) that the clinical user adjust the patient to a more horizontal position to achieve appropriately aligned compressions using a piston style chest compression device.

The technical personnel representative, in some embodiments, is enabled to issue, via the network 108, commands or control signals to the medical device platform 102. For example, the technical personnel representative may request release of operational data and/or device performance metrics from the medical device platform 102 via the network 108 based upon credentials supplied by the technical personnel via the clinical or mobile application 112. In another example, the technical personnel representative may adjust an operating parameter on the medical device platform 102 to be more appropriate to the conditions represented in the operational data and/or described by the clinical user such as, in some examples, patient biometrics (e.g., size and/or age of patient), transport conditions (e.g., ambulance, helicopter, ship, etc.), or alert conditions (e.g., mechanical faults, error codes, etc.). In illustration, the technical personnel representative may issue one or more control signals to the medical device platform 102 to adjust compression rate and/or compression depth based on patient biometrics. Conversely, the technical personnel representative may walk the clinical user through making such adjustments, then obtain subsequent operational data to ensure compliance with the instructions.

In some implementations, rather than or in addition to technical personnel assistance, the alert/help engine 162 of the clinical or mobile application 112 supports live clinical assistance for a user of the medical device platform 102. The alert/help engine 162, for example, may enable medical staff, such as physicians or surgeons, to review the clinical metrics related to an en route patient while communicating with a clinical user (e.g., emergency medical technician) regarding the patient's status. For example, clinical data and/or metrics may be uploaded from the platform 102, accessory unit 104, and/or data integrator 106 to a network accessible location to provide a real time or near real time update to a live medical professional for supporting the clinician user in providing care for the patient prior to the patient's arrival at the medical facility or, conversely, prior to the medical professional's arrival at the care location or facility. In an illustrative example, at least a portion of the information presented to the clinical user via the GUI engine 150*b* of the clinical or mobile application 112 may be further presented to one or more remotely located medical professionals for providing support in medical triage. The clinical user may be provided with voice communications with the medical professional, for example via the accessory unit 104 or data integrator 106, to talk through triage care using a microphone I/O interface. The medical professional, conversely, may be provided with voice communications via a speaker I/O interface to respond to the clinical user with suggestions or requests for further information.

In some embodiments, the medical professional is supplied with additional clinical data and/or clinical metrics for a more fulsome analysis of the patient's status. For example, while an ambulance EMT may be supplied with a very simple heads-up display interface providing key details such as compression rate and blood pressure, the medical professional may be provided with metrics, graphs, and/or tables demonstrating patient physiological data (e.g., blood pressure, EKG, etc.) and clinical operational data (e.g., compression rate, compressions over time, defibrillator therapy delivery, etc.) over time (e.g., since start of the therapy session). Further, while the clinical user may be provided clinical data and/or metrics regarding a single device (e.g., the mechanical chest compression platform 102), the medical professional may be presented with integrated data and/or metrics. For example, the session data 120 along with accessory data 122 and/or integrator data 124 may be uploaded via the network 108 for review by the medical professional in an integrated user interface. In this manner, in illustration, the medical professional may review clinical metrics regarding both the mechanical chest compression platform 102 and the defibrillator type data integrator 106 to understand the extent of therapy supplied to the patient during the integrated therapy session.

The real time or near real time clinical metrics provided in the end user display, in some implementations, are presented as part of a training application for training clinical users on using the medical device platform and/or the medical resuscitation system. The interface and feedback provided by the training application, for example, may be generated by a training engine 160 of the clinical or mobile application 112.

In some implementations, the clinical or mobile application 112 includes one or more management engines to manage various devices deployed at a location, such as a hospital, fire station, military installation, or emergency medical facility. As illustrated, the clinical or mobile application 112 includes a data integrator management engine 164*a*, an accessory unit management engine 164*b*, and a platform management engine 164*c*. The management engines 164 may combine as an inventory management system to manage inventory at a centrally located system, such as a front desk monitor or dedicated tablet computer. The inventory management system, for example, may receive wireless signals from various medical device platforms 102, accessory units 104, and/or data integrators 106 housed at the facility. The wireless signals may carry device information and operational information for each of the platforms 102, accessory units 104, and/or data integrators 106. The inventory management system 164 may analyze the signals received from the platforms 102, accessory units 104, and/or data integrators 106 and present status indicators for each of the platforms 102, accessory units 104, and/or data integrators 106. The status indicators, in some examples, may include low power warnings, error conditions, device faults, device locations, and/or in-use indications. The clinical or mobile application 112, for example, may be executing on a wall powered device mounted in a known location to provide the facility with information on the installations of the various platforms 102, accessory units 104, and/or data integrators 106. In the event that the facility is large and/or signal propagation is limited (e.g., due to brick walls, etc.), in some embodiments, in addition to the clinical or mobile application 112, the facility may have one or more beacons (e.g., repeaters) and/or cellular units deployed at one or more locations in the facility to boost the signals transmitted by the platforms 102, accessory units 104, and/or data integrators 106. In other embodiments, the platforms 102, accessory units 104, and/or data integrators 106 may forward messages from other platforms 102, accessory units 104, and/or data integrators 106 in a mesh network architecture to deliver signals from remotely located platforms 102, accessory units 104, and/or data integrators 106 to the centrally located device executing the inventory engine 164 through the clinical or mobile application 112.

In some implementations, the inventory management system receives information regarding the platforms 102, accessory units 104, and/or data integrators 106 via the network 108. For example, the data integrator management engine 164*a*, accessory management engine 164*b*, and platform management engine 164*c* may be part of a network-connected application (e.g., a tablet computer app) or browser-accessible management portal to manage devices at one or more locations, such as at a large medical campus, teaching campus, military installation, and/or city emergency services offices. The inventory management system, for example, may automatically receive information from the various devices on a periodic basis. In some embodiments, each of the medical device platforms 102, accessory units 104, and data integrators 106 issues separate session data 120, accessory data 122, and integrator data 124 to the network 108. In other embodiments, the data integrator 106 forwards information regarding one or more medical device platforms 102 and/or accessory units 104, as provided by the devices 102/104 via the communication links 128*a,b*. The information, in some examples, may be received at least by the data integrator 106 on a periodic basis and forwarded to the clinical or mobile application 112 via the network 108 on network availability. The periodic basis, in one illustration, may be based on a self-test frequency. For example, each of the medical device platforms 102, accessory units 104, and/or data integrators 106 may include a self-test routine for determining any alerts, failure conditions, or warnings regarding sensed operational parameters. The operational parameters, in some examples, may include temperature (e.g., overheating), essential component functionality (e.g., malfunction of the motor, presence or proper attachment of a belt of the medical device platform 102), or battery status (e.g., power maintenance alert). In another illustration, each of the medical device platforms 102, accessory units 104, and/or data integrators 106 may supply software operational parameters such as, in some examples, a software installation version, a firmware version, a battery expiration date, a time since last network connectivity event, or a cumulative time in use.

The inventory management system, in some implementations, includes a variety of management views, each providing the administrator with different information regarding the status of the various devices (e.g., medical device platforms 102, accessory units 104, and/or data integrators 106). In a first example, the views may include a location view, identifying locations of various devices. The locations, further to the example, may be provided within a map of the facility or in a table identifying each device and its present location (e.g., floor, room, department, ambulance identifier such as license plate number, etc.). The locations may be automatically derived or entered by an administrator (e.g., device N has been allocated to department M, device O has been allocated to ambulance P, etc.). For example, for medical device platforms including a GPS locator, the GPS location may be used to identify a present location (or most recently identified location) of the medical device platform. In a second example, the views may include a device-type specific view such as a medical device platform view representing status of each medical device platform, an accessory unit view representing status of each accessory unit, and/or a data integrator view representing status of each data integrator. Further, in a third example, the views may include a view representing each device corresponding to high priority status indicator, where indicators are separated into levels of status (e.g., low priority status, medium priority status, and high priority status). A high priority status indicator, in some examples, may correspond to a power maintenance alert, an overheating alert, or an essential component malfunction alert. In a fourth example, a maintenance view may provide the user with upcoming maintenance tasks such as, in some examples, a battery expiration date within X window of time (e.g., one month) or availability of a software and/or firmware update. Each view may include one or more tables, graphs, icons, and other graphical user interface elements. Some GUI elements may be user selectable for more information. For example, upon selection of a particular device from the high priority status view, information from the location view may be made available to identify a location of the device requiring timely maintenance or service.

An administrator, in some implementations, reviews the status indicators, such as one or more low power warnings, error conditions, device faults, device locations, and/or in-use indications on a graphical user interface such as a monitor. Further, in some embodiments, an administrator receives alerts regarding certain status indicators to address the status in a timely fashion. For example, the inventory management system may be configured to provide alerts, via one or more communications means, to one or more registered administrators regarding potential problems with one or more devices (e.g., high priority status alerts). The communication channels for alert delivery, in some examples, can include email, text message, or smart device application notification. For example, a smart device application may be designed to provide the administrator with a graphical user interface similar to a main inventory management system display (e.g., reconfigured for smaller screen and/or simplified to only provide critical information, etc.). The communications means and/or status indicators meriting the issuance of alerts via these communication channels, may be user-configurable. In a further example, in some embodiments, a maintenance department or maintenance system may be automatically alerted regarding certain status indicators. For example, the inventory management system may provide information regarding certain status indicators to a manufacturer email account, application, or portal to obtain timely manufacturer assistance or replacement equipment in the event of a serious problem with one of the devices.

In some embodiments, the inventory management system, via the data integrator management engine 164*a*, accessory management engine 164*b*, and platform management engine 164*c*, may be configured to issue commands to one or more of the devices 102, 104, and 106. For example, the inventory management system may push software updates to a group of devices 102, 104, or 106 via the network 108. In another example, the inventory management system may issue a command for self-testing of all medical device platforms 102, accessory units 104, and/or data integrators 106 accessible directly or indirectly via the network 108.

Similar to the inventory management system described above, in some implementations, the accessory unit management engine 164*b*, the platform management engine 164*c*, and the data integrator management engine 164*a* of the clinical or mobile application 112 may provide a centrally located (e.g., wall mounted) status application for use in a mobile paramedic unit, such as an ambulance or helicopter. The management application in the mobile paramedic unit, for example, may display status information regarding each device allocated to the mobile paramedic unit, such as a status of an automated chest compression platform, a status of each rechargeable battery unit, and a status of a mobile defibrillator. Further, the management application may provide simple diagnostics and help messages in the event of a warning of fault condition of one of the medical devices.

Operations performed by the example environment 100 for secure data sharing, as described above, may be performed by various engines. At least some of the engines, in some embodiments, are embodied as software programs or algorithms, stored as instructions to a non-volatile (e.g., non-transitory) computer-readable medium such as a memory device, on-chip integrated memory unit, or other non-volatile computer-readable storage. At least a portion of the engines, in some embodiments, are embodied in hardware logic. The hardware logic may be coded on a reprogrammable computing chip such as a field programmable gate array (FPGA) or other reconfigurable logic device. In a further example, the hardware logic may be coded on a custom microchip, such as an application-specific integrated circuit (ASIC). The operations of various engines of the cloud analytics platform 110 and/or the clinical or mobile application 112 may be performed by software operations distributed in a server farm or cloud computing environment. In some embodiments, customized logic devices, such as programmable logic devices, may be allocated to perform a portion of the operations.

Medical Device System Use-Case Examples

In some implementations, the medical device platform 102 for delivering automated chest compressions to a patient is connected to a patient suffering cardiac arrest while in a medical facility environment, such as a hospital or clinic. The medical device platform 102 may collect and/or calculate the session data 120 during delivery of the chest compressions and periodically share the session data 120 with the accessory unit 104 while the accessory unit 104 is nearby or releasably coupled to the platform 102. For example, the medical device platform 102 may establish a short-range wireless communication connection, such as a Bluetooth, Radio Frequency (RF), Zigbee, or optical connection, with the accessory unit 104 at the beginning of the treatment session with the patient. In another example, the medical device platform 102 may establish a direct (wired) communication connection, such as an Ethernet connection, universal serial bus (USB) connection, or other serial data interface connection. The accessory unit 104, in some examples, may be a rechargeable battery unit, a defibrillator, e.g., an automated external defibrillator (AED), a ventilator, or a portable (e.g., tablet, etc.) computing device. In some implementations, the medical device platform 102 is configured to transmit data via a short-range wireless communication transmitter, e.g. a Bluetooth beacon, to a receiver.

The accessory unit 104, in some embodiments, collects and/or calculates the accessory data 122 while the accessory unit 104 is releasably coupled to the platform 102. For example, during coordinated usage with the medical device platform 102, the accessory unit 104 may log metrics to the memory device 116 regarding performance of the accessory unit 104. During coupling, the accessory unit 104 and the medical device platform 102 may synchronize clocks so that timestamps of the session data 120 may be later matched with timestamps of the accessory data 122.

A summary report may include clinical metrics regarding treatment supplied by the chest compression platform only or both a chest compression platform and a defibrillator. In some implementations, the accessory unit 104 and/or data integrator 106 shares clinical data and/or metrics with the platform 102, or vice versa, for incorporation into the session summary report. The presentation of the metrics, in some implementations, is divided by event markers identifying discrete events during treatment. The events may include, in some examples, a stop, start, or pause in compressions event, power on or off, battery removal/replacement, actuation of a latching or locking mechanism holding the battery in position, belt end or belt tab insertion/removal (e.g., left or right), replacement, or misalignment (e.g., in relation to the medical device platform 102), and/or a belt guard attachment/detachment, replacement, or misalignment (e.g., in relation to the medical device platform 102). In the circumstance of a defibrillator-type data integrator 106, the events may include delivery of shock therapy, start of a defibrillation cycle, a length of time of charging prior to delivery of shock therapy, a length of time of EKG assessment, and/or an EKG change event or heart rate change event captured by sensors of the defibrillator-type data integrator 106. In further examples, the events may include errors and/or alerts such as over-temperature, over-current, or low battery in the platform 102, accessory unit 104, or data integrator 106 and/or, more generally, any error or alert leading to a stop or pause in treatment. The events may include a ventilation delivery event by a ventilator type accessory unit 104. Further, regarding the medical device platform 102 or defibrillator type data integrator 106, events may include a patient not found event.

In some embodiments, the accessory unit 104 is coupled to the medical device platform 102 during multiple treatment sessions. In this circumstance, the session data 120 may include a session identifier and/or session delimiter identifying differences between the sessions. For example, each session may begin at a start time and terminate at an end time logged in the session data 120.

The accessory unit 104, in some embodiments, is swapped with a different replacement accessory unit during a single treatment session. In this circumstance, in some implementations, session data 120 previously transferred to the accessory unit 104 may be obtained from the memory device 114 of the medical device platform 102 and transferred to the replacement accessory unit in an effort to transfer all data for the same treatment session to a single accessory unit.

After the accessory unit 104 has been decoupled from the medical device platform, in some embodiments, the accessory unit 104 is coupled to the data integrator 106. The accessory unit 104 may transfer the session data 120 and the accessory data 122 to the data integrator 106 during coupling. For example, the accessory unit 104 may establish a short-range wireless communication connection, such as a Bluetooth, Radio Frequency (RF), Zigbee, or optical connection, with the docking unit 106. The data integrator 106 may be a network connection unit and/or a charging unit for recharging a battery of the accessory unit 104. In other examples, the data integrator 106 may be a defibrillation unit or portable (e.g., tablet, etc.) computing device. In some embodiments, the accessory unit 104 may be communicatively coupled to both the medical device platform 102 and the data integrator 106 simultaneously. For example, the accessory unit 104 may behave as a data pass-through device between the medical device platform 102 and the data integrator 106. In some implementations, the accessory unit 104 is configured to transmit data via a short-range wireless communication transmitter, e.g., a Bluetooth beacon, to a receiver.

The data integrator 106, in some embodiments, is a network connection unit for transferring the session data 120 and the accessory data 122 to a remote network 108. For example, the data integrator 106 may have a wired, secure network connection (e.g., Ethernet connection) for sharing the session data 120 and the accessory data 122 with the cloud analytics platform 110. The data integrator 106, further, may collect data integrator data 124 regarding the functionality of the data integrator 106 for transfer to the network 108.

In some implementations, the medical device platform 102 for delivering automated chest compressions to a patient is connected to a patient suffering cardiac arrest by emergency medical response personnel, for example prior to loading into an ambulance for transfer to a medical facility. As described above, the medical device platform 102 may collect and/or calculate the session data 120 during delivery of the chest compressions and periodically share the session data 120 with the accessory unit 104 while the accessory unit 104 is releasably coupled to the platform 102.

In some embodiments, the medical device platform 102 includes a global positioning system (GPS) receiver for identifying a location of the platform 102. For example, upon activating power to the medical device platform 102 or beginning compressions on the medical device platform 102, the GPS receiver may determine a beginning location of medical treatment. Further, in some embodiments, the GPS receiver may periodically update a location. In illustration, during particular events (e.g., activating compressions to begin the treatment session, pausing the treatment session, changing a compression mode of the platform 102 during the treatment session, or replacing the accessory unit 104 with another accessory unit 104) the GPS receiver may attempt to determine a position. The GPS data may be included in the session data 120.

The medical device platform 102, in some embodiments, includes an accelerometer sensor for identifying movements or orientation of the medical device platform 102 during transfer of the patient to the medical facility. The accelerometer sensor, for example, may collect tilt metrics regarding an angle of offset of the platform from a recommended neutral (e.g., horizontal) position. In another example, the accelerometer sensor may collect metrics regarding bouncing, jarring, or dropping of the medical device platform 102 while the medical device platform 102 is powered on (e.g., before, during, and/or after the platform 102 is coupled to a patient). The GPS positioning data may be included in the session data 120.

Upon delivery of the patient to the medical facility, in some embodiments, the patient is removed from the platform 102 and the platform 102 is returned to the ambulance. A clinical user may connect a portable storage device, such as a universal serial bus (USB) flash drive, to a physical port of the medical device platform 102 to retrieve a session summary report of the session data 120. The session summary report, for example, may include a portion of the session data 120 regarding at least the most recent treatment session. Further, in some embodiments, the medical device platform 102 may transfer additional session data, such as sensor readings and other device performance metrics, to the portable storage device in an encrypted format for review by an authorized user (e.g., a representative of the manufacturer of the medical device platform 102).

In some implementations, the medical device platform 102 for delivering automated chest compressions to a patient includes a peripheral communication port and/or wireless (e.g., Wi-Fi) communication port for communicating with the mobile application 112 executing on a portable computing device for support in troubleshooting problems with the medical device platform 102. The mobile application 112, in some embodiments, translates error codes and/or alerts into more detailed explanations for an end user. Further, the mobile application 112, in some embodiments, assists the user in connecting with support personnel of the platform manufacturer for assistance with troubleshooting a problem the user has encountered with the medical device platform 102.

In some implementations, the medical device platform 102 for delivering automated chest compressions to a patient is connected to a CPR manikin while in a training facility environment, such as a medical school, fire station, or medical facility. As described above, the medical device platform 102 may collect and/or calculate the session data 120 during delivery of the chest compressions and periodically share the session data 120 with the accessory unit 104 while the accessory unit 104 is releasably coupled to the medical device platform 102. Further, upon wireless or wired connection with a portable computing device executing the mobile application 112, students may be presented with training information for learning to use the various features of the medical device platform 102. In another example, the mobile application 112 may log interactions of the student with the medical device platform 102 to evaluate the student's ability to operate the medical device platform 102.

In some implementations, a medical device system managing mobile application is installed on a computing device at a facility such as a fire station, hospital, or campus (e.g., college, large corporate facility, military base, assisted living facility, etc.) that houses at least one medical device platform 102, multiple accessory units 104, and at least one data integrator 106. The computing device, for example, may be a centrally mounted or otherwise centrally located interactive display (e.g., tablet computer) for review by a dispatcher or emergency medical response coordinator of the facility. The computing device may perform as the data integrator. The mobile application may receive portions of the session data 120, the accessory data 122, and/or the data integrator data 124 via wireless transmissions from the medical device platform 102, the accessory unit 104, and/or the data integrator 106. For example, the medical device platform 102 may supply a location, any error condition(s), and/or a current status (e.g., in use, idle, powered off). The accessory unit 104 may supply a battery charge level, any error condition(s), and/or a current status (e.g., charging, in use, in storage). The data integrator 106 may supply a network connection status, any error condition(s), and/or a current status (e.g., charging, idle). The mobile application may present information regarding the current availability and condition of the various platforms, accessory units, and/or data integrators in the facility. For example, the mobile application may highlight to a user those devices in need of charging, servicing, or other attention to ensure availability of functioning units in the event of a medical emergency.

Example Methods for Secure Data Sharing

FIGS. 2A-2D, 3A, and 3B illustrate various methods for secure data sharing in a medical resuscitation system and a resuscitation platform environment. The methods of FIGS. 2A-2D, 3A, and 3B can be performed by the various devices and engines described in relation to FIG. 1A. The communication paths, for example, can include communication paths described in relation to the example network communication stack of FIG. 1B.

Medical Device Platform Data Sharing Method

Figure 2A:
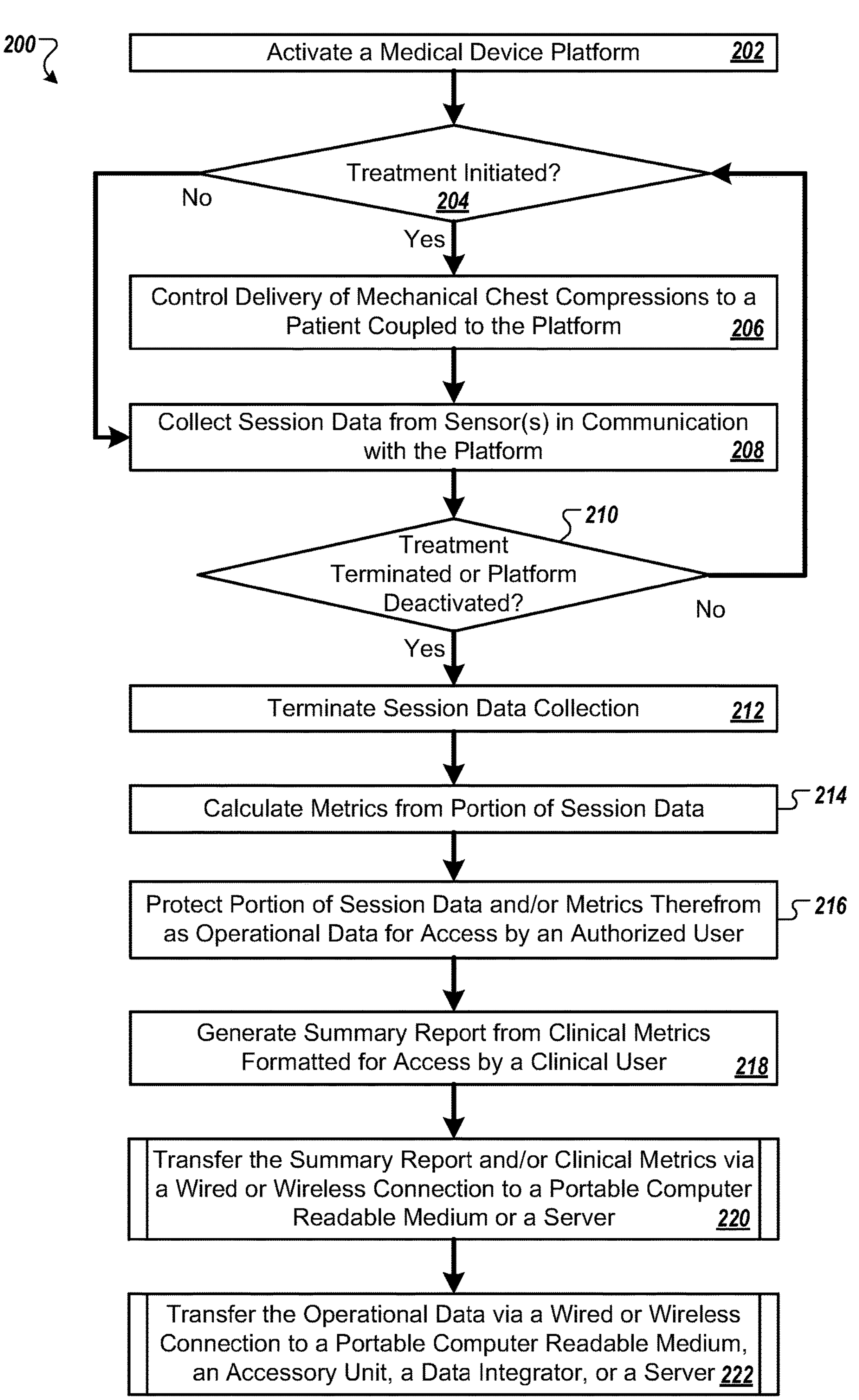
FIG. 2A is a flow chart of an example method for gathering data by an automated chest compression platform and sharing the data with an accessory unit designed for interoperability with the automated chest compression platform.
Figure 4A:
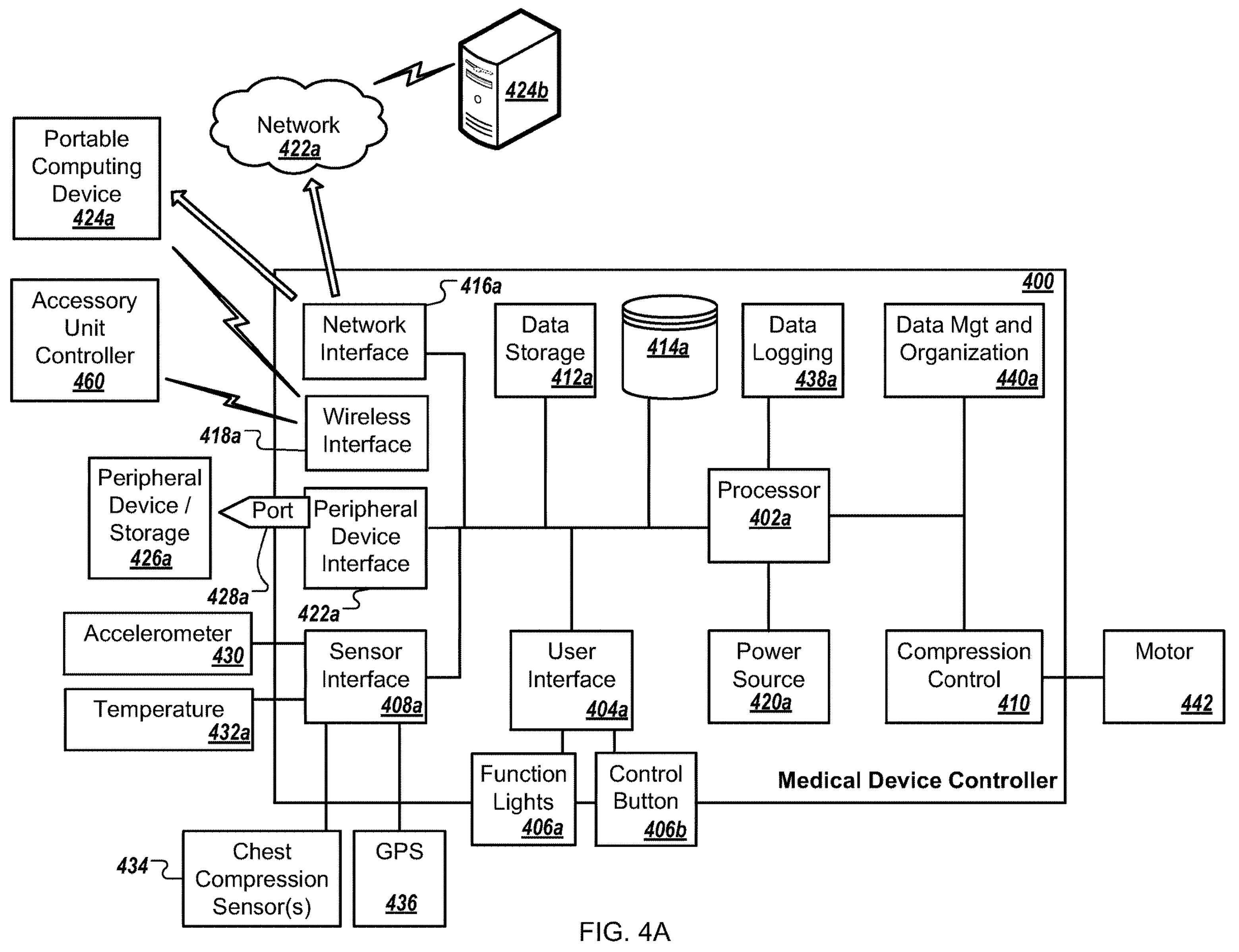
FIG. 4A is a block diagram of an example medical device controller for an automated chest compression platform.

Turning to FIG. 2A, in some implementations, an example method 200 for gathering data by an automated chest compression platform and sharing the data with an accessory unit designed for interoperability with the automated chest compression platform begins with activating a medical device platform (202). The medical device platform, for example, may be the medical device platform 102 of FIG. 1A. In some embodiments, activation begins with powering on the device platform. For example, the medical device platform may be controlled in part by a medical device controller such as a medical device controller 400 of FIG. 4A. As illustrated in FIG. 4A, a user interface 404 of the medical device controller 400 includes at least one control button 406*b* for activating control of the medical device controller 400. In other embodiments, activation begins with activating treatment by the device platform. Treatment, for example, may be activated by another control button 406*b* of the medical device controller 400.

In some implementations, if treatment has been initiated (204), delivery of mechanical chest compressions to a patient coupled to the platform is controlled (206). A controller of the medical device platform, for example, may automate the delivery of chest compressions to the patient. The delivery may be controlled in part based upon a compression mode selected by a user through the user interface. The controller, for example, may be the medical device controller 400 described in relation to FIG. 4A, and one of the control buttons 406*b* may be used to control a compression mode.

In some implementations, session data is collected from one or more sensors in communication with the platform (208). The sensors, for example, may include one or more sensors connected to a sensor interface 408 of the medical device controller 400 of FIG. 4A such as an accelerometer 430, a temperature sensor 432*a*, one or more chest compression sensors 434 and/or a GPS receiver 436. The session data may be collected by the data logging engine 126*a* of the medical device platform 102 of FIG. 1A. The session data, for example, may include the sensor data 522 and/or metrics 524 described in relation to the chest compression platform 500 of FIG. 5A.

If, instead, the medical device platform is activated (202), but treatment has not yet been initiated (204), session data is collected from one or more sensors in communication with the platform (208). For example, upon activation such as powering on the device platform, data may be collected from a positioning sensor such as a GPS receiver to identify a present location of the device platform. In another example, operational data may be collected from the platform, such as a battery charge level, any error conditions or alerts, or an orientation of the platform (e.g., from an accelerometer sensor or tilt sensor).

In some implementations, after initiation of the treatment (204), the method 200 continues to control delivery of mechanical chest compressions (206) and to collect session data from the sensor(s) (208) until the treatment is terminated or the platform is otherwise deactivated (210). For example, the method 200 may repeat the controlling (206) and collecting (208) until a treatment deactivation control or power control is actuated by a user. In other implementations, treatment may terminate upon disconnection of power to the medical device platform or a battery source of the medical device platform running too low on charge to support controlling delivery of the mechanical chest compressions.

In some implementations, after treatment has been terminated (210), session data collection is terminated (212). For example, the data logging engine 126*a* may terminate collection of the session data 166*a*, as discussed in relation to FIG. 1A.

In some implementations, metrics are calculated from a portion of the session data (214). For example, the metrics engine 140 of the medical device platform 102 may calculate metrics from raw data captured by the data logging engine 126*a* and stored by the data archival engine 134*a* to the non-volatile memory 114*a*. The metrics may vary based upon the type of medical device platform. Examples of metrics are provided in relation to FIGS. 5A and 5B as the metrics 524 and the metrics 558. The metrics, for example, may include clinical metrics regarding patient treatment during therapy delivery as well as device performance metrics regarding medical device platform performance during therapy delivery. Certain metrics may qualify as both clinical metrics and device performance metrics, in some embodiments.

The clinical metrics, in some examples, may include a number of pauses during treatment, a depth of chest compression, a number of samples of compression depth, a duty cycle of chest compressions, a percentage of pauses relative to compression time during treatment delivery, a compression rate, an amount of time spent in compression relative to the entire therapy delivery session, and/or a compression fraction.

The device performance metrics may include, in some examples, error codes, selection of functional modes, selection of control settings, and/or alert conditions of the medical device platform. Chest compression specific device performance metrics may include, in some examples, chest displacement, current requirements over the compression cycle, tilt of the medical device platform, a temperature of the housing of the platform, a temperature of a motor controlling delivery of the compressions, and/or a fan speed of a cooling fan disposed in the housing. The chest compression specific device performance metrics may be used to derive or estimate patient information such as, in some examples, size of a patient and/or chest stiffness of a patient. In a particular example regarding a belt-style chest compression platform such as the compression platform 500 of FIG. 5A, the device performance metrics may include a position of motor shaft over time and/or a position of each spool and/or drive shaft over time. Regarding the compression platform 530, the operational data may include a piston orientation and/or piston depth of delivery. The operational data, additionally, may be device-specific, such as device design information (e.g., device serial number, model, etc.), output of the source code executing on the controller of the medical device platform, firmware version identifier(s), and/or software version identifier(s).

In some implementations, a portion of the session data and/or metrics therefrom is protected as operational data for access by an authorized user (216). In some examples, an authorized user may include quality assurance personnel, technical support personnel, and engineering development personnel associated with a manufacturer of the medical device platform. In some embodiments, the operational data is encrypted. For example, the data encryption engine 136 of FIG. 1A may encrypt the portion of the session data as operational data for access by a user credentialed to review information regarding the functioning of the medical device platform. In other embodiments, the operational data is formatted in a proprietary format that is not directly readable.

In some implementations, a summary report is generated from the clinical metrics in a format accessible to a clinical user of the medical device platform (218). In some examples, the clinical user may include a medical professional, treatment supervisor, medical facility administrator, student or staff instructor, or emergency medical responder. The contents of the summary report may include, in some examples, an identifier of the particular device (e.g., model, version, serial number, etc.), a session start time, a session end time, a session duration, a compression rate, a compression count, a compression fraction, a number of pauses, a total length of pause time, and/or a device status. The summary report may include one or more function mode changes or other modifications of control options selected by a user of the medical device platform, and/or one or more locations of the medical device platform during the treatment session. Further, in some embodiments, the summary report may include a listing of one or more events during therapy delivery such as, in some examples, a time of session pause, a time of session resumption, a stop or start in compressions event, power on or off, battery removal/replacement, actuation of a latching or locking mechanism holding the battery in position, belt end or belt tab insertion/removal (e.g., left or right), replacement, or misalignment (e.g., in relation to the medical device platform 102), and/or a belt guard attachment/detachment, replacement, or misalignment (e.g., in relation to the medical device platform 102). In the circumstance of a defibrillator-type data integrator 106, the events may include delivery of shock therapy, start of a defibrillation cycle, a length of time of charging prior to delivery of shock therapy, a length of time of EKG assessment, and/or an EKG change event or heart rate change event captured by sensors of the defibrillator-type data integrator 106. In further examples, the events may include errors and/or alerts such as over-temperature, overcurrent, or low battery in the platform 102, accessory unit 104, or data integrator 106 and/or, more generally, any error or alert leading to a stop or pause in treatment. The events may include a ventilation delivery event by a ventilator type accessory unit 104. Further, regarding the medical device platform 102 or defibrillator type data integrator 106, events may include a patient not found event. Event markers may be used to partition the information in the summary report. The summary report, in some embodiments, contains no patient-confidential information or other information that could link the summary report data to a particular patient.

In some embodiments, the summary report includes clinical metrics obtained from an accessory unit or data integrator, such as a defibrillator, supplying coordinated treatment with the medical device platform. For example, the accessory unit 104 and/or data integrator 106 of FIG. 1A may share clinical data and/or metrics with the platform 102 for incorporation into the session summary report.

In some implementations, the summary report and/or clinical metrics are transferred via a wired or wireless connection to a portable computer readable medium or a server for review by a clinical user (220). The summary report, for example, may be downloaded from the medical device platform to a device or storage medium (e.g., tablet computer, USB Flash drive, etc.) via a wired or wireless connection. In another example, the clinical metrics may be transferred to a server for remote generation of the summary report or a summary user interface. The summary report, in some embodiments, is formatted for review by a user in a standard (e.g., ISO 32000) printer-ready format, such as a PDF file. In some embodiments, the summary report is formatted for review by a user in a browser-friendly format, such as an HTML document. In further embodiments, the summary report is formatted for inclusion in the American Health Association (AHA) national reporting database. In some implementations, the summary report is transmitted via a short-range wireless communication transmitter, e.g. a Bluetooth beacon, to a receiver.

Figure 3A:
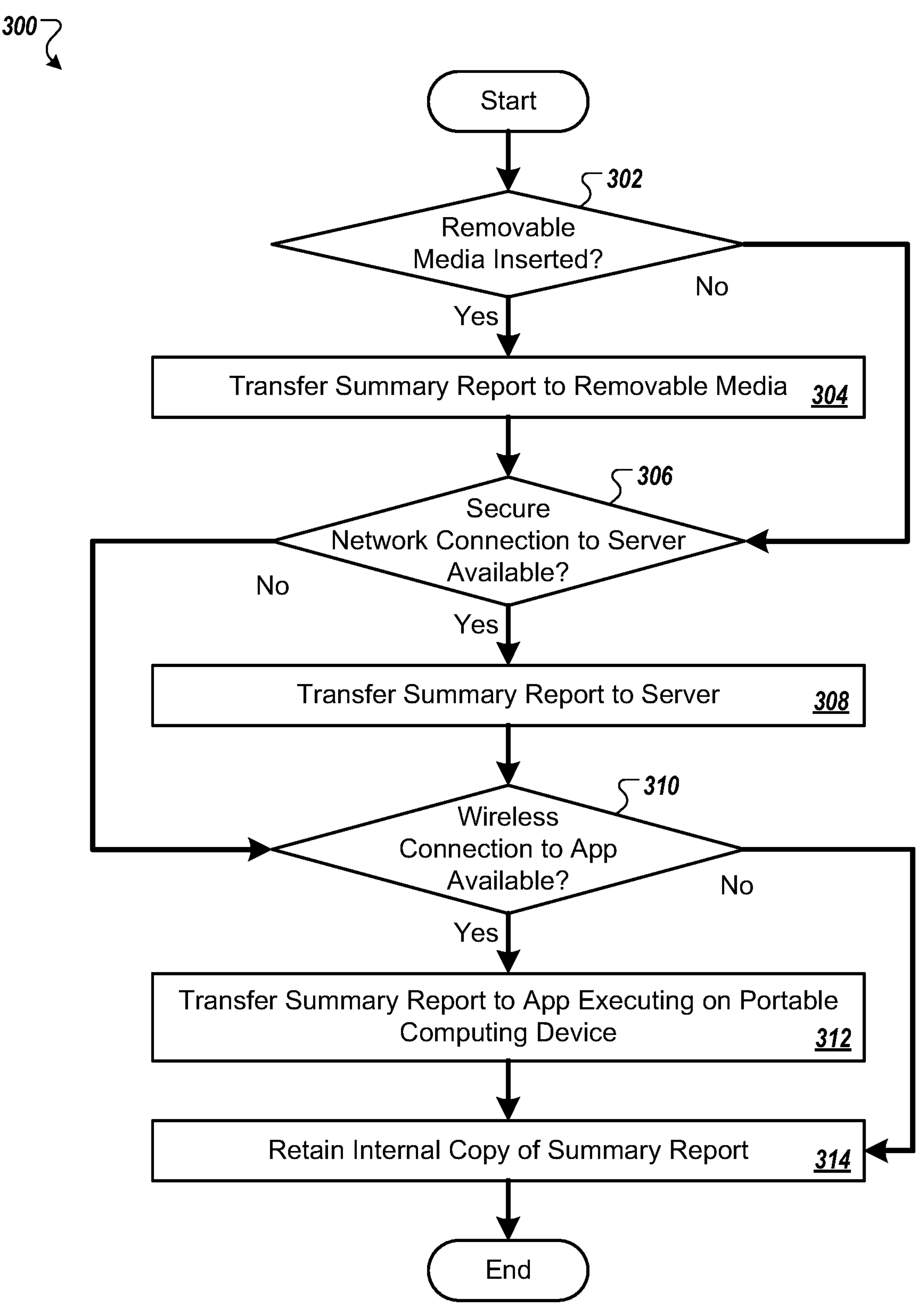
FIG. 3A is a flow chart of an example method for transferring a summary report from an automated chest compression platform to a networked device.

Turning to FIG. 3A, in some implementations, an example method 300 for transferring a summary report from a medical device platform for review by a clinical user begins with determining whether a removable media has been inserted into a port of the medical device platform (302). The port, for example, may be the port 428*a* in communication with the peripheral device interface 422*a* of the medical device controller 400 of FIG. 4A. The removable media may be the peripheral device and/or storage 426*a* of FIG. 4A. In an illustrative example, the port may be a USB port and the removable media may be a USB Flash drive. In some implementations, the summary report is transferred (304) immediately upon insertion of the removable media (302). In other implementations, user identification or authentication is required to initiate transfer (304) of the summary report to the removable media. For example, the user may be requested to scan an identification badge, provide biometric information such as a fingerprint scan or voice scan, or enter a passcode or password prior to transfer of the summary report.

In some implementations, if a secure network connection to a server is available (306), the summary report is transferred to the server (308). The server, in some examples, may be a hospital server, fire station server, or medical facility server configured to communicate with the medical device platform. The secure network connection, for example, may be an encrypted network connection. The network connection, in some embodiments, conforms with medical facility data confidentiality requirements, such as HIPAA (Health Insurance Portability and Accountability Act) requirements. The secure connection may be established over a wired connection to a local network, such as a campus network. The wired connection may be an Ethernet connection. In other embodiments, the secure connection may be established via a wireless connection.

In some implementations, the summary report is transferred to the server (308). The summary report, for example, may be stored to a facility records database and/or patient treatment records database. In some implementations, the summary report is provided with additional information, such as a device identifier, location (e.g., hospital room) and/or timestamp to support matching the summary report with a patient and/or treatment program. The summary report, in some embodiments, is presented to a user at a display of a computing device connected to the server, such as a laptop computer, tablet computer, or smart device.

In some implementations, if a wireless connection to an application configured for interoperation with report data provided by the medical device platform is available (310), the summary report is transferred to the application executing on a portable computing device (312). For example, the clinical or mobile application 112 of FIG. 1A may be configured to accept the summary report (or clinical metrics for generating the same) and to present the summary report via the GUI engine 150*b* of the clinical or mobile application 112. The application may be configured to accept authenticated login information from authorized clinical users prior to presenting the summary report.

In some implementations, a copy of the summary report is retained internally by the medical device platform (314). For example, the medical device platform 102 may retain a copy of the summary report in the non-volatile memory 114*a*. The data archival engine 134*a*, for example, may be configured to maintain a collection of summary reports from a set of therapy sessions.

Although described as a particular series of steps, in other embodiments, more or fewer steps may be included. For example, rather than retaining an internal copy of the summary report (314), the summary report may be removed from internal memory after transferring. Conversely, in another example, one or more older summary reports may be removed upon retention of a most recent summary report. In another example, prior to determining if a wireless connection is available (310), the method 300 may first receive a user input requesting transfer of the summary report via a wireless connection. For example, the medical device platform may avoid wireless communication unless a command is issued to avoid interference with other medical devices during patient treatment. In further embodiments, certain steps may be performed in a different order, or two or more steps may be performed in parallel. For example, the check for a secure network connection (306) may be performed after or at the same time as determining whether a wireless connection is available (310). Other modifications of the method 300 are possible while remaining in the scope and purpose of the method 300.

Returning to FIG. 2A, in some implementations, the operational data is transferred via a wired or wireless connection to a portable computer readable medium, an accessory unit, a data integrator, or a server for application or review by an authorized user (222). The operational data, in some embodiments, is transferred with the summary report or clinical metrics (e.g., in different formats for review by the different classes of users). In other embodiments, the operational data is transferred to a separate storage medium, device, or network connection than the summary report. In some implementations, the operational data is transmitted via a short-range wireless communication transmitter, e.g. a Bluetooth beacon, to a receiver.

Figure 3B:
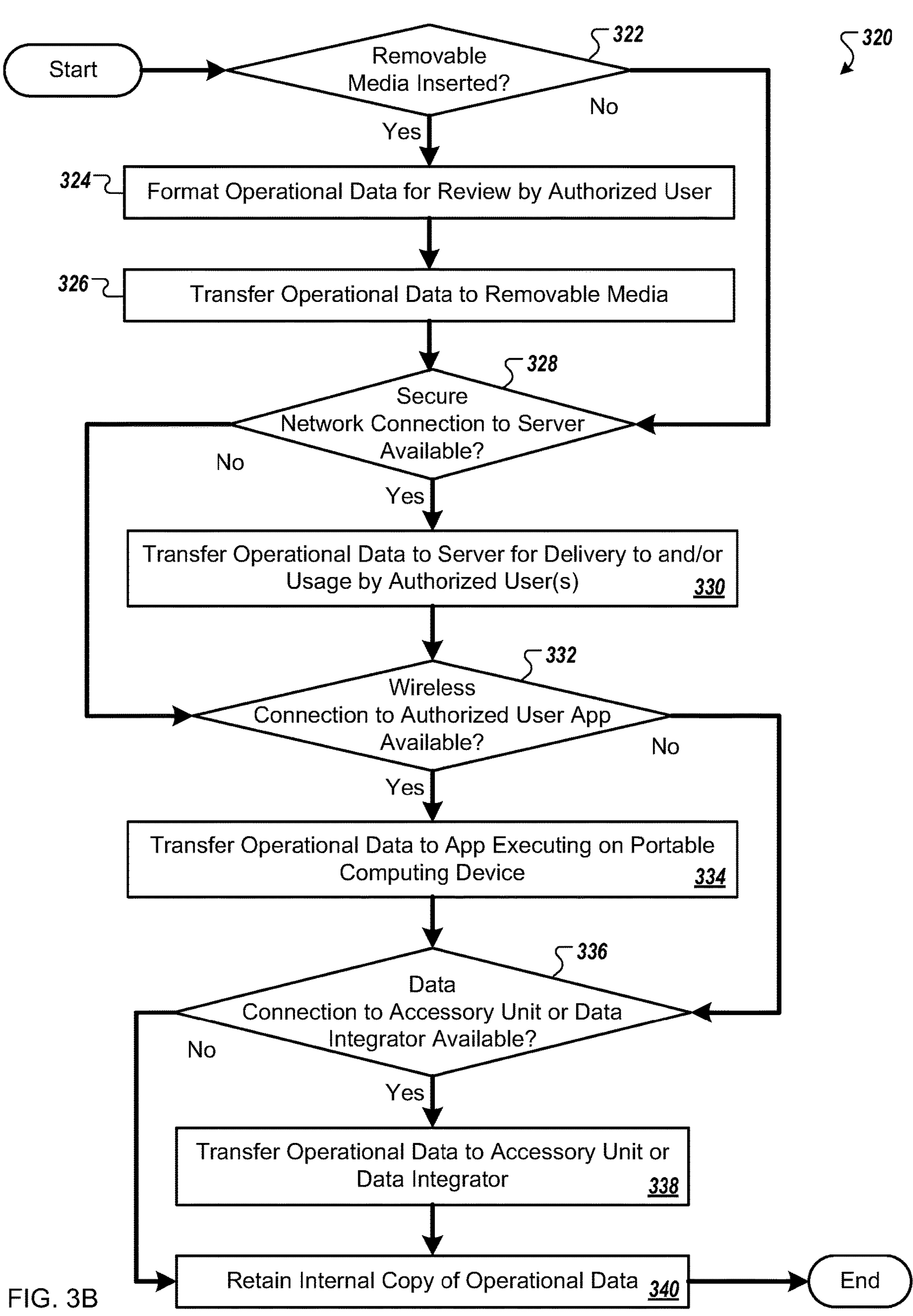
FIG. 3B is a flow chart of an example method for transferring operational data from an automated chest compression platform to a separate device.

Turning to FIG. 3B, in some implementations, an example method 320 for transferring operational data for eventual usage or review by an authorized user begins with determining whether a removable media has been inserted (322). The port, for example, may be the port 428*a* in communication with the peripheral device interface 422*a* of the medical device controller 400 of FIG. 4A. The removable media may be the peripheral device and/or storage 426*a* of FIG. 4A. In an illustrative example, the port may be a USB port and the removable media may be a USB Flash drive.

In some implementations, if a removable media has been inserted (322), the operational data is formatted for review by an authorized user (324). In some examples, an authorized user may include quality assurance personnel, technical support personnel, and engineering development personnel associated with a manufacturer of the medical device platform. In some embodiments, the operational data is encrypted. For example, the data encryption engine 136 of FIG. 1A may encrypt the portion of the session data as operational data for access by a user credentialed to review information regarding the functioning of the medical device platform. In other embodiments, the operational data is formatted in a proprietary format that is not directly readable.

In some implementations, the operational data is transferred to the removeable media (326). In some implementations, the operational data is transferred immediately upon insertion of the removable media (if pre-formatted) or after formatting. In other implementations, user identification or authentication is required to initiate transfer of the operational data to the removable media. For example, the user may be requested to scan an identification badge, provide biometric information such as a fingerprint scan or voice scan, or enter a passcode or password prior to transfer of the operational data.

In some implementations, if a secure network connection to a server is available (328), the operational data is transferred to the server for delivery to and/or usage by one or more authorized users (330). The server, in some examples, may be a quality assurance, technical support, or development server for reviewing operational data and device performance metrics related to a medical device platform. The server may be configured to communicate with the medical device platform. In an example, the server may be part of the cloud analytics platform 110, as described in relation to FIG. 1A. The secure network connection, for example, may be an encrypted network connection. The secure connection may be established over a wired connection to a local network, such as a campus network. The wired connection may be an Ethernet connection. The operational data, for example, may be stored to the data store 116 of the cloud analytics platform 110 by the data archival engine 146*a*. The record linking engine 154 may link the operational data with other operational data from a same device, same location, and/or same timeframe. The GUI engine 150*a* may provide a user interface for authorized user review of the operational data.

In some implementations, if a wireless connection to an authorized user application is available (332), the operational data is transferred to the application executing on a portable computing device (334). For example, the clinical or mobile application 112 of FIG. 1A may be configured to accept the operational data and to present a portion of the operational data via the GUI engine 150*b* of the clinical or mobile application 112. The application may be configured to accept authenticated login information from authorized users prior to presenting the operational data. The operational data may be presented, for example, to an authorized repair or service technician via the alert/help engine 162. In an illustrative embodiment, the operational data may be passed through a customer support application to a remote server for help in troubleshooting a problem that a clinical user is having with the medical device platform.

In some implementations, if a data connection to an accessory unit or data integrator is available (336), the operational data is transferred to the accessory unit or data integrator (338). The operational data, for example, may be transferred from the medical device platform 102 to the accessory unit 104 via the data communication connection 128*a* between the medical device platform 102 and the accessory unit 104. For example, the peripheral communication engine 130*a* may establish a direct (e.g., wired) communication link 128*a* with the accessory unit 104 and/or the wireless communication engine 132*a* may establish a wireless communication link 128*a* with the accessory unit 104 to transfer the operational data and/or clinical metrics, e.g., a summary report, to the accessory unit 104 and/or data integrator 106. The wireless communication link 128*a*, in some embodiments, is a short-range wireless data broadcast that may be intercepted by a wireless receiver of the accessory unit 104 and/or a wireless receiver of the data integrator 106 or other device, rather than being a bi-directional wireless communication link with a particular device. Conversely, the accessory unit 104 may establish the communication link 128*a* with the medical device platform 102 (e.g., via a wireless communication engine 132*b* or peripheral communication engine 130*b*) to request the operational data from the medical device platform. Example communication paths involving a medical device platform, an accessory unit, and a data integrator are described in greater detail below in relation to FIGS. 6A through 6C.

In some implementations, a copy of the operational data is retained internally by the medical device platform (340). For example, the medical device platform 102 may retain a copy of the operational data in the non-volatile memory 114*a*. The data archival engine 134*a*, for example, may be configured to maintain sets of operational data from a set of therapy sessions.

Although described as a particular series of steps, in other embodiments, more or fewer steps may be included. For example, prior to transmitting via a wireless connection, in some implementations, a user may activate a control to enable wireless communication. The control, for example, may be used to protect against the medical device platform issuing wireless signals during treatment of a patient such that the signals may interfere with other medical equipment in the area. In further embodiments, certain steps may be performed in a different order, or two or more steps may be performed in parallel. For example, the operational data may be transferred to a removable media (326) at the same time as being transmitted via a network (330) or wireless (334) connection. Other modifications of the method 320 are possible while remaining in the scope and purpose of the method 320. For example, while the summary report is described as being generated (218) by the medical device platform, in other embodiments, the platform may share clinical data and/or metrics with the accessory unit or data integrator for incorporation into the session summary report. In illustration, a defibrillator type data integrator may integrate clinical data and/or metrics from the chest compression platform with integrator metrics generated by the data integrator to generate an integrated session summary report. The integrated session summary report may be accessible from the data integrator in similar means as described in relation to the medical device platform.

Returning to FIG. 2A, although described in a particular series of steps, in some implementations, more or fewer steps may be performed. For example, rather than generating the summary report (218), clinical metrics may be provided to an external computing device or server (220) for generation of a summary report or summary GUI presentation. In further embodiments, certain steps may be performed in a different order or in parallel. For example, clinical metrics and/or operational data, in other embodiments, may be transferred (220, 222) periodically during the therapy session. Other modifications of the method 200 are possible without exceeding the scope and purpose of the method 200.

Accessory Unit Data Sharing Method

Figure 2B:
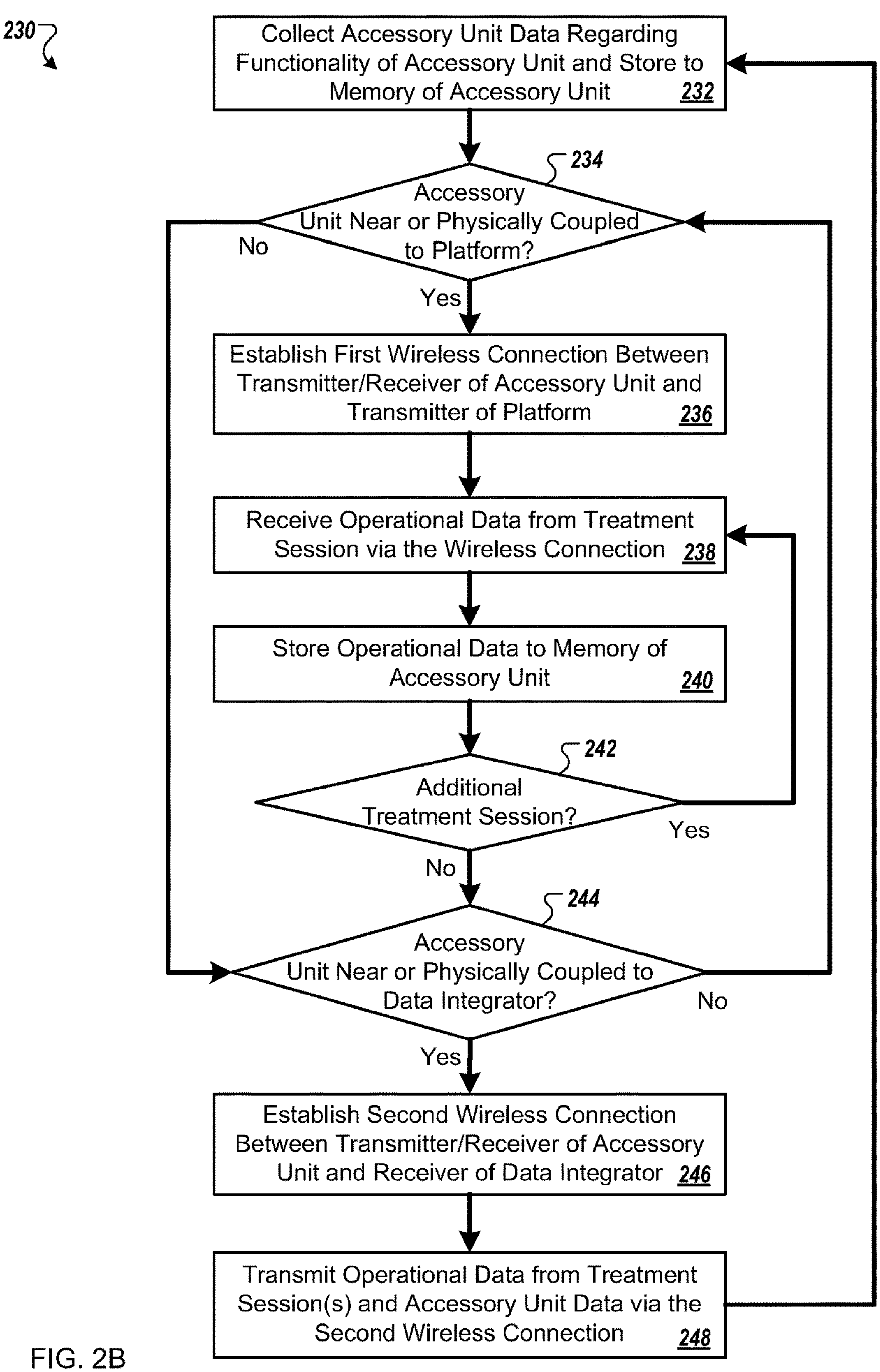
FIG. 2B is a flow chart of an example method for gathering data from a medical device platform by an accessory unit and sharing the data with a data integrator designed for interoperability with the accessory unit.

FIG. 2B is a flow chart of an example method 230 for gathering data from a medical device platform by an accessory unit and sharing the data with a data integrator designed for interoperability with the accessory unit. The accessory unit, in some examples, may be a rechargeable battery unit, a portable (e.g., tablet, etc.) computer, a ventilator, or a defibrillator. The accessory unit, in some embodiments, is designed to cooperate with the medical device platform, such as an automated chest compression platform, to delivery resuscitative therapy to a patient. The method 230, for example, may be performed by the accessory unit 104 of FIG. 1A and/or by the processor 402*c* of the accessory unit controller 460 of FIG. 4C.

Figure 4B:
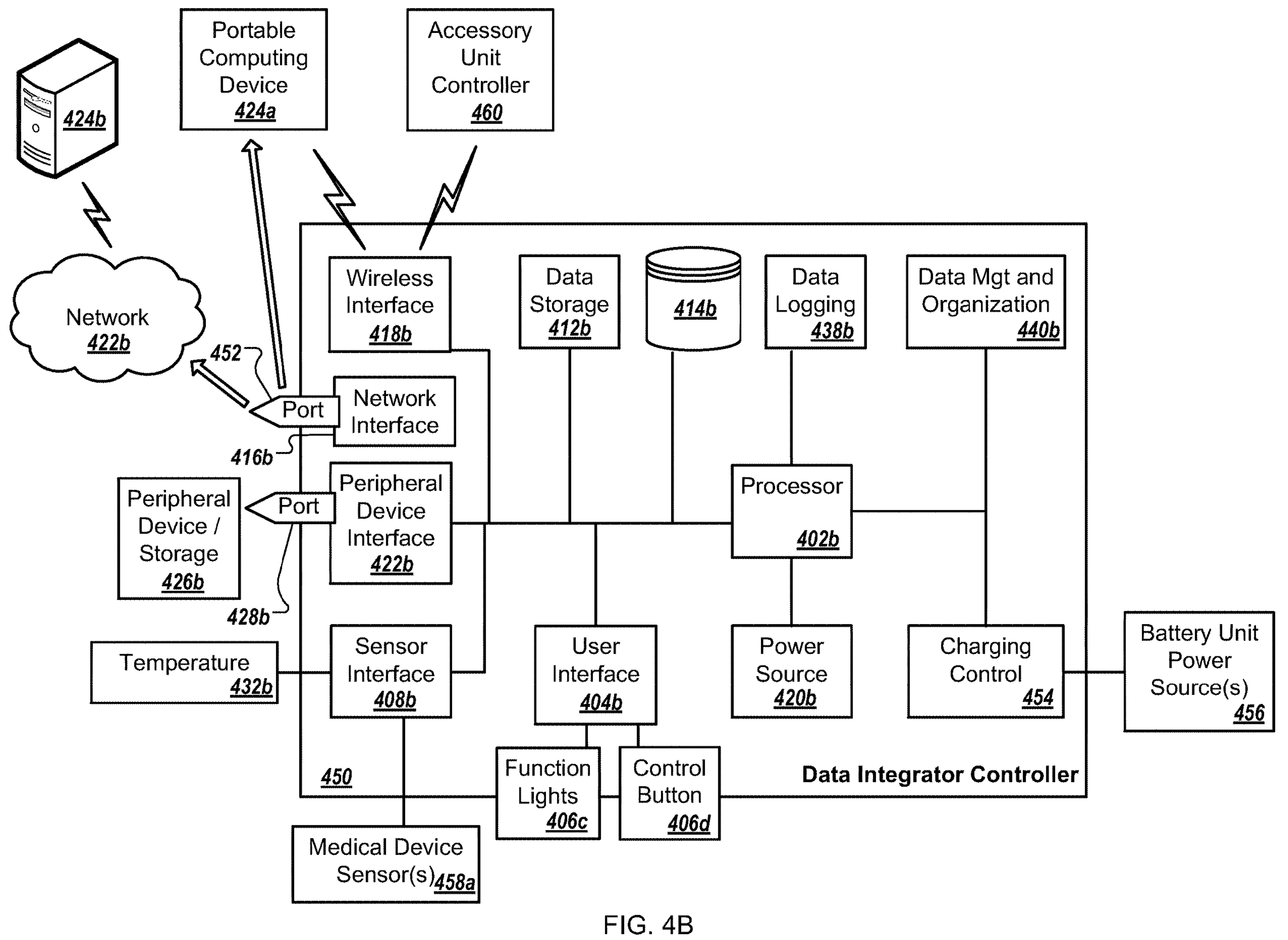
FIG. 4B is a block diagram of an example data integrator controller for a data integrator configured for use with an automated chest compression platform.
Figure 4C:
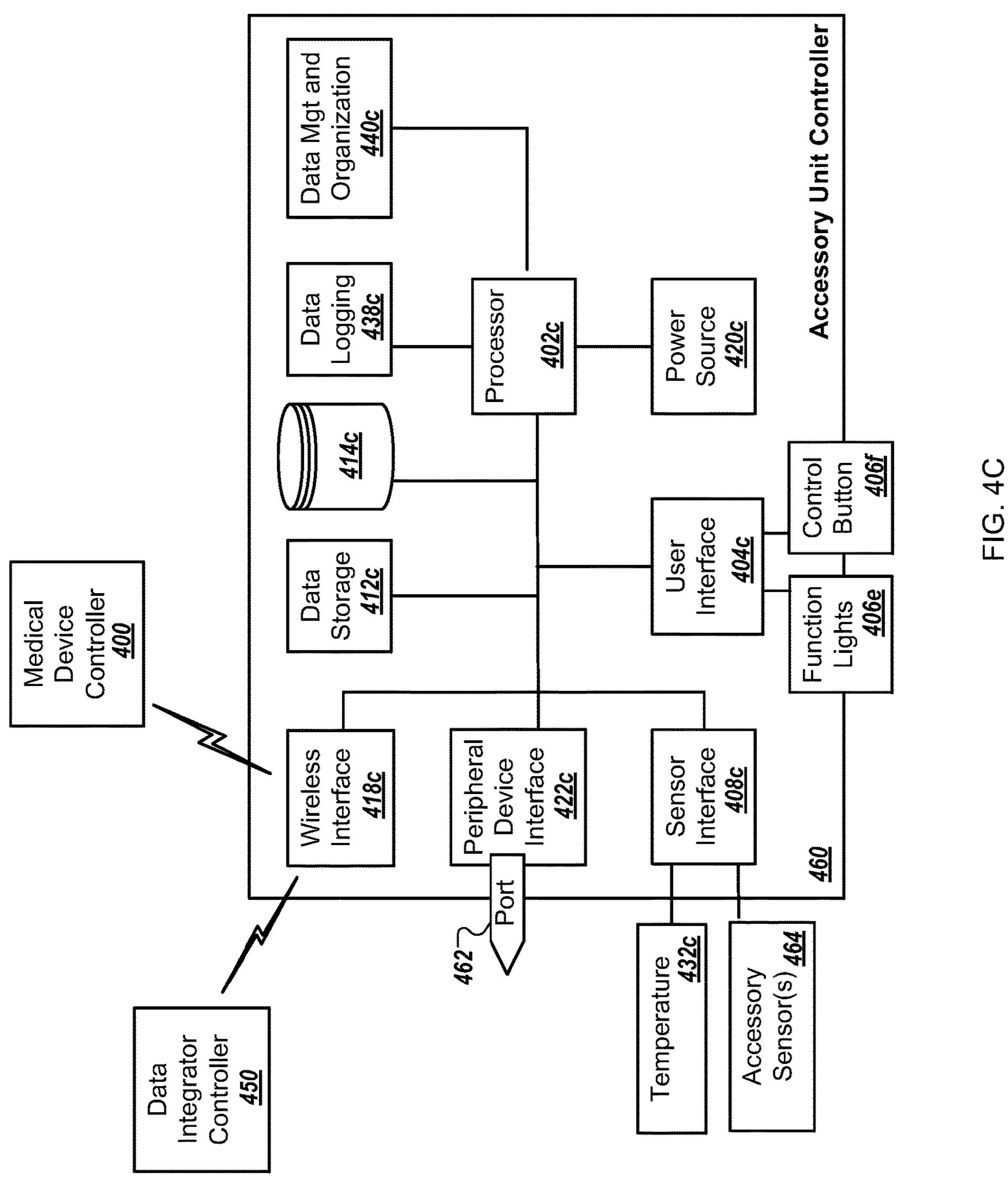
FIG. 4C is a block diagram of an example accessory unit controller for an accessory unit configured for use with an automated chest compression platform.

In some implementations, the method 230 begins with collecting accessory unit data regarding functionality of an accessory unit and storing the accessory unit data to a memory of the accessory unit (232). The accessory unit data, for example, may be collected from one or more sensors integrated into and/or in communication with the accessory unit. For example, the accessory unit controller 460 of FIG. 4C collects data from a temperature sensor 432*c* and accessory sensor(s) 464. As illustrated in FIG. 5C, in another example, a rechargeable battery unit type accessory unit 560 may collect temperature sensor readings 566*a*, current sensor readings 566*b*, and/or voltage sensor readings 566*c*. The accessory unit data, in another example, may include metrics derived from sensor data collected by the accessory unit. Further data collected by the accessory unit can include, in some examples, an accessory unit identifier, one or more timestamps, an accessory unit location, software versions executing on the accessory unit, control settings, alert or error conditions of the accessory unit, and/or modes of operation of the accessory unit. For example, as illustrated in FIG. 5C, a rechargeable battery unit type accessory unit 560 may generate metrics including an energy level 568*a*, a time attached to the medical device platform 568*b*, a session begin time 568*c*, and/or an alert type 568*d*. FIG. 5D includes another example device, a defibrillator, that may be used in some embodiments as an accessory unit and that collects various sensor data 586*a* and generates metrics 588, as described in further detail below.

In some implementations, if the accessory unit is near or physically coupled to a medical device platform (234), a wireless connection is established between a transmitter/receiver of the accessory unit and a transmitter of the platform (236). As illustrated in FIG. 1B, for example, a wireless connection may be established between the platform 102 and the accessory unit 104 via the wireless communication link 180. Turning to FIG. 4C, the wireless interface 418*c* of the accessory unit controller 460 may establish a connection with or, alternatively, capture a wireless broadcast from, the medical device controller 400, e.g., a broadcast that includes clinical data. The wireless connection, in some embodiments, is a short-range wireless connection, such as a Bluetooth connection, configured to avoid interference with other medical equipment during therapy. In other embodiments, the wireless connection is a Wi-Fi connection, configured to transmit information between equipment within an operating room or other region of a location such as a medical facility.

In some implementations, operational data from the treatment session is received via the wireless connection (238). The operational data, as described above in relation to steps 216 and 222 of the method 200 of FIG. 2A, may be sensor data and/or calculated metrics collected on behalf of a manufacturer of the medical device platform for troubleshooting problems or error conditions in the medical device platform and/or for monitoring usage of medical device platforms and various deployments. The operational data may include data not useful to clinical users of the medical platform and/or proprietary manufacturer data. The operational data, further, may include information regarding the source of the operational data (e.g., the medical device platform) and/or the treatment session (e.g., timestamp, modes of operation, etc.). The wireless interface 418*c* of the accessory unit controller 460 of FIG. 4C may receive the operational data and pass the operational data to the processor 402*c*.

In some implementations, the operational data is stored to a non-volatile memory of the accessory unit (240). The operational data, for example, may be stored to the non-volatile memory 114*b* of the accessory unit 104, as illustrated in FIG. 1A. As described in relation to FIG. 4C, the operational data may be stored to a non-volatile memory region 414*c* by the data storage engine 412*c* of the accessory unit controller 460.

In some implementations, if an additional treatment session is started while the accessory unit is near or coupled to the medical device platform (242), the accessory unit receives addition operational data (238) and stores the additional operational data (240) related to the next treatment session. For example, a rechargeable battery unit may be coupled to an automated compression device platform for multiple treatment sessions. In some embodiments, the data management and organization engine 440*c* may manage storage of multiple sessions of operational data in the non-volatile memory region 414*c*, for example through timestamps and/or organization by device identifier.

In some implementations, if the accessory unit is near or physically coupled to a data integrator (244), the accessory unit establishes a second wireless connection between the transmitter/receiver of the accessory unit and a receiver of the data integrator (246). The data integrator, in some examples, may be a defibrillator unit, a portable (e.g., tablet, etc.) computing device, a battery recharging unit, or an accessory docking unit. The accessory unit, in some embodiments, is decoupled from the medical device platform and coupled to the data integrator. In other embodiments, the accessory unit is coupled to or near the medical device platform while also being coupled to or near the data integrator. For example, the accessory unit may be a rechargeable battery unit coupled to the medical device platform while near a tablet computing device type data integrator. In another example, the accessory unit may be a tablet computing device near the medical device platform while being docked in a docking station type data integrator. Other configurations are possible.

As illustrated in FIG. 1B, for example, a wireless connection may be established between the accessory unit 104 and the data integrator 106 via the wireless communication link 180. Turning to FIG. 4C, the wireless interface 418*c* of the accessory unit controller 460 may establish a connection with or, alternatively, capture a wireless broadcast from, the data integrator controller 450, e.g., a broadcast of clinical data. The wireless connection, in some embodiments, is a short-range wireless connection, such as a Bluetooth connection, configured to avoid interference with other medical equipment during therapy. In other embodiments, the wireless connection is a Wi-Fi connection, configured to transmit information between equipment within an operating room or other region of a location such as a medical facility.

In some implementations, operational data from the treatment session and accessory unit data is transmitted to the data integrator via the second wireless connection (248). The operational data and accessory unit data, for example, may be transferred from the accessory unit 104 to the data integrator 106 via the data communication connection 128*b* between the accessory unit 104 and the data integrator. For example, the wireless communication engine 132*b* may establish a wireless communication link 128*b* with the data integrator 106 to transfer the operational data to the data integrator 106. The wireless communication link 128*b*, in some embodiments, is a short-range wireless data broadcast that may be intercepted by a wireless receiver of the data integrator 106, rather than being a bi-directional wireless communication link with a particular device. Conversely, the data integrator 106 may establish the communication link 128*b* with the accessory unit 104 (e.g., via the wireless communication engine 132*c* or peripheral communication engine 130*c*) to request the operational data from the accessory unit 104. Rather than a wireless connection, in other embodiments, the peripheral communication engine 130*b* may establish a direct (e.g., wired) communication link 128*b* with the data integrator 106. For example, the accessory unit may be physically coupled to the data integrator to establish a direct data communication path. Example communication paths involving a medical device platform, an accessory unit, and a data integrator are described in greater detail below in relation to FIGS. 6A through 6C.

Although described in a particular series of steps, in some implementations of the method 230, more or fewer steps may be performed. For example, rather than storing the accessory unit data to the memory of the accessory unit (232), the accessory unit may behave as a pass-through device, providing data for storage to the medical device platform and/or to the data integrator. Similarly, rather than storing the operational data to the memory of the accessory unit (240), in some embodiments, the method 230 may act as a pass-through device, immediately transmitting the operational data (248) to an already established second wireless connection (246) or, alternatively, a physical connection. In another example, rather than establishing a wireless connection (236), in some embodiments, upon physical coupling of the accessory unit with the medical device platform, a wired communication link may be established to transfer operational data from the medical device platform to the accessory unit. In further embodiments, certain steps may be performed in a different order or in parallel. For example, operational data and/or accessory unit data may be periodically transferred to the data integrator via the second wireless connection during the treatment session (e.g., in a pass-through manner) rather than storing the operational data and/or accessory data to the non-volatile memory of the accessory unit. Other modifications of the method 230 are possible without exceeding the scope and purpose of the method 230.

Data Integrator Data Sharing Method

Figure 2C:
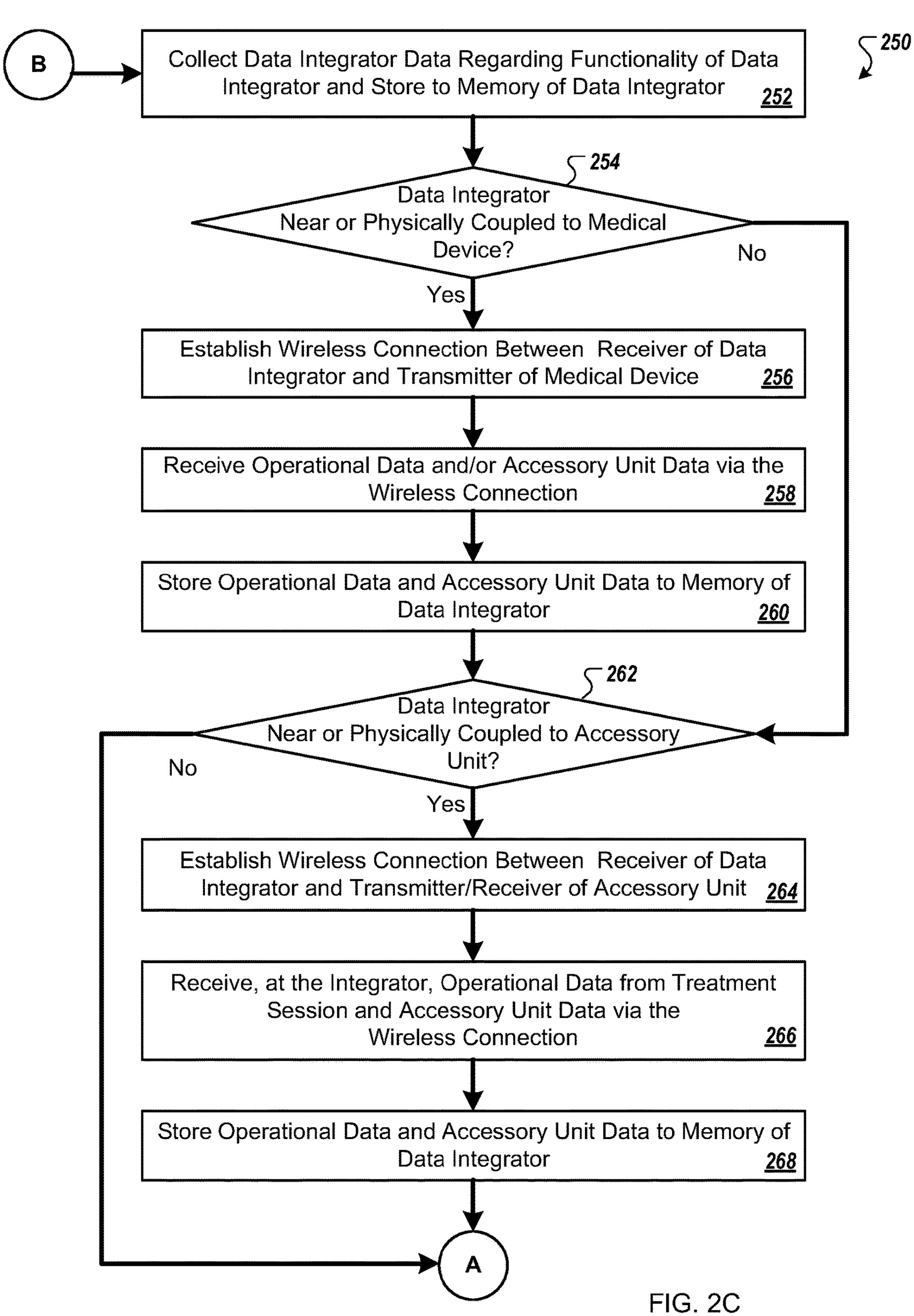
FIGS. 2C and 2D illustrate a flow chart of an example method for gathering data by a data integrator from an accessory unit and sharing the data via a communications network.
Figure 2D:
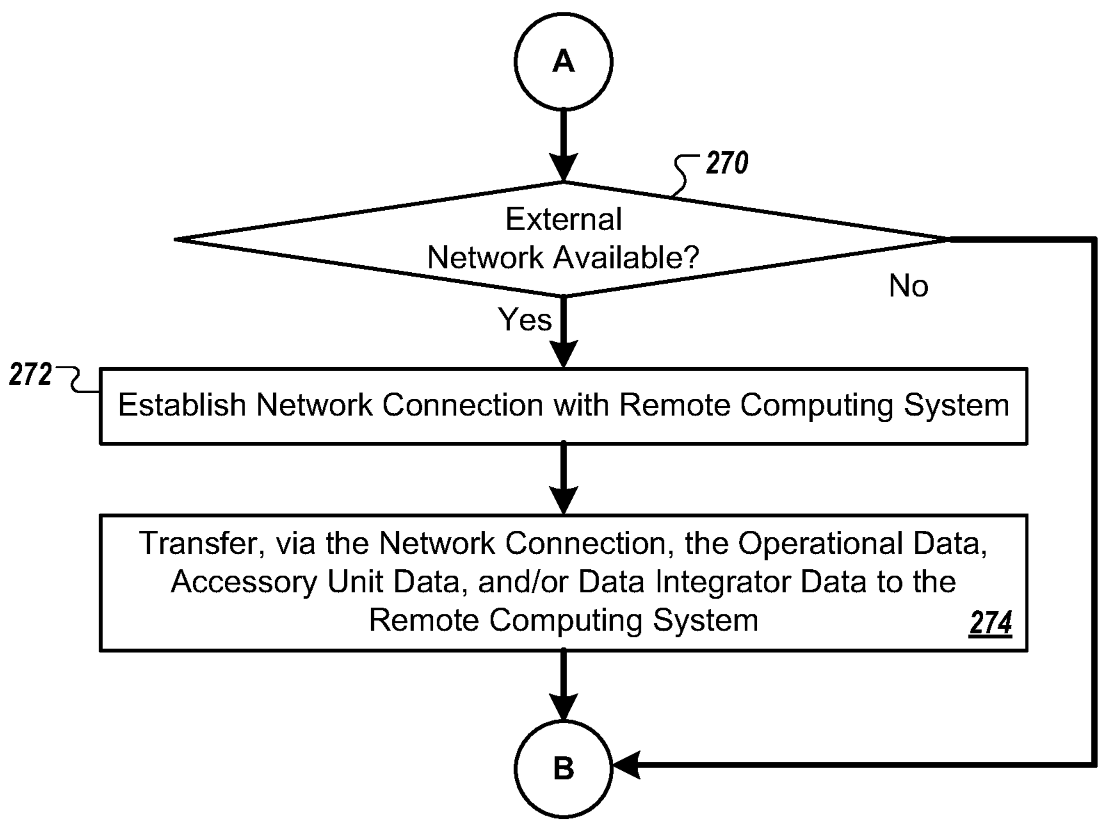

FIGS. 2C and 2D illustrate a flow chart of an example method 250 for gathering data from an accessory unit by a data integrator designed for interoperability with the accessory unit and sharing the data with a networked computing system. The data integrator, in some examples, may be a portable (e.g., tablet, etc.) computer, a defibrillator, a battery charging unit, or a docking station. The data integrator, in some embodiments, is designed to cooperate with the medical device platform, such as an automated chest compression platform, to delivery resuscitative therapy to a patient. For example, a defibrillator type accessory unit may coordinate therapy with an automated chest compression platform. The method 250, for example, may be performed by the data integrator 106 of FIG. 1A and/or by the processor 402*b* of the data integrator controller 450 of FIG. 4B.

In some implementations, the method 250 begins with collecting data integrator data regarding functionality of a data integrator and storing the data integrator data to a memory of the data integrator (252). The data integrator data, for example, may be collected from one or more sensors integrated into and/or in communication with the data integrator. For example, the data integrator controller 450 of FIG. 4B collects data from a temperature sensor 432*b* and medical device sensor(s) 458*a*. As illustrated in FIG. 5D, in another example, a defibrillator unit type data integrator 570 may collect temperature sensor readings 586*a*, current sensor readings 586*b*, voltage sensor readings 586*c*, and/or pulse readings 586*d*. In another illustrative example, shown in FIG. 5E, a charging unit type data integrator 590 may collect temperature sensor readings 597*a*, current sensor readings 597*b*, and/or voltage sensor readings 597*c*. The data integrator data, in another example, may include metrics derived from sensor data collected by the data integrator. Further data collected by the data integrator can include, in some examples, a data integrator identifier, one or more timestamps, a data integrator location, software versions executing on the data integrator, control settings, alert or error conditions of the data integrator, and/or modes of operation of the data integrator. For example, as illustrated in FIG. 5D, the defibrillator unit type data integrator 570 may generate metrics including current delivery metrics 588*b*, physiologic waveforms 588*c* such as an ECG waveform, and/or blood pressure metrics 588*d*. FIG. 5E includes another example device, a battery charging unit, that may generate metrics 598, as described in further detail below.

In some implementations, if the data integrator is near or physically coupled to a medical device platform (254), a wireless connection is established between a transmitter/receiver of the data integrator and a transmitter of the platform (256). As illustrated in FIG. 1B, for example, a wireless connection may be established between the platform 102 and the data integrator 106 via the wireless communication link 180. Turning to FIG. 4B, the wireless interface 418*b* of the data integrator controller 450 may establish a connection with or, alternatively, capture a wireless broadcast, e.g., a broadcast of clinical data, from, the medical device controller 400. The wireless connection, in some embodiments, is a short-range wireless connection, such as a Bluetooth connection, configured to avoid interference with other medical equipment during therapy. In other embodiments, the wireless connection is a Wi-Fi connection, configured to transmit information between equipment within an operating room or other region of a location such as a medical facility.

In some implementations, operational data from the treatment session is received via the wireless connection (258). The operational data, as described above in relation to steps 216 and 222 of the method 200 of FIG. 2A, may be sensor data and/or calculated metrics collected on behalf of a manufacturer of the medical device platform for troubleshooting problems or error conditions in the medical device platform and/or for monitoring usage of medical device platforms and various deployments. The operational data may include data not useful to clinical users of the medical platform and/or proprietary manufacturer data. In some examples, the operational data may include data regarding device performance problems, error conditions (e.g., as displayed to a user of the device via a user interface), fault warnings, operating temperatures, power usage, compression belt or piston positioning, and/or raw sensor readings (e.g., rotary encoder, accelerometer, pressure sensor, load sensor, etc.). The operational data, further, may include information regarding the source of the operational data (e.g., the medical device platform) and/or the treatment session (e.g., timestamp, modes of operation, etc.). The wireless interface 418*b* of the data integrator controller 450 of FIG. 4B may receive the operational data and pass the operational data to the processor 402*b*.

In some implementations, the operational data is stored to a non-volatile memory of the data integrator (260). The operational data, for example, may be stored to the non-volatile memory 114*c* of the data integrator 106, as illustrated in FIG. 1A. As described in relation to FIG. 4B, the operational data may be stored to a non-volatile memory region 414*b* by the data storage engine 412*b* of the data integrator controller 450. If a same set of operational data has already been received at step 258, in some implementations, the data integrator removes duplicate copies of the data rather than storing two separate sets of the same data.

In some implementations, if the data integrator is near or physically coupled to an accessory unit (262), the data integrator establishes a wireless connection between the receiver of the data integrator and a transmitter/receiver of the accessory unit (264). The accessory unit, in some embodiments, is coupled to the data integrator. In other embodiments, the accessory unit is coupled to or near the medical device platform while also being coupled to or near the data integrator. As illustrated in FIG. 1B, for example, a wireless connection may be established between the data integrator 106 and the accessory unit 104 via the wireless communication link 180. Conversely, a wired connection may be established between the data integrator 106 and the accessory unit 104 via the peripheral bus 178 (e.g., connecting to the accessory unit 104 as the peripheral memory 184). Turning to FIG. 4B, the wireless interface 418*b* of the data integrator controller 450 may establish a connection with or, alternatively, capture a wireless broadcast, e.g., a broadcast of clinical data, from, the accessory unit controller 460. The wireless connection, in some embodiments, is a short-range wireless connection, such as a Bluetooth connection, configured to avoid interference with other medical equipment during therapy. In other embodiments, the wireless connection is a Wi-Fi connection, configured to transmit information between equipment within an operating room or other region of a location such as a medical facility.

In some implementations, operational data from the treatment session and accessory unit data is received by the data integrator via the wireless connection (266). The operational data and accessory unit data, for example, may be transferred from the accessory unit 104 to the data integrator 106 via the data communication connection 128*b* between the accessory unit 104 and the data integrator 106. For example, the wireless communication engine 132*c* may establish the wireless communication link 128*b* with the accessory unit 104 (or vice versa) to transfer the operational data to the data integrator 106. The wireless communication link 128*b*, in some embodiments, is a short-range wireless data broadcast that may be intercepted by a wireless receiver of the data integrator 106, rather than being a bi-directional wireless communication link with a particular device. Rather than a wireless connection, in other embodiments, the peripheral communication engine 130*c* of the data integrator 106 may establish a direct (e.g., wired) communication link 128*b* with the accessory unit 104. For example, the accessory unit may be physically coupled to the data integrator to establish a direct data communication path. Example communication paths involving a medical device platform, an accessory unit, and a data integrator are described in greater detail below in relation to FIGS. 6A through 6C.

In some implementations, the operational data and the accessory unit data is stored to a non-volatile memory of the data integrator (268). The operational data and the accessory unit data may be stored to the non-volatile memory 114*c* of FIG. 1A, for example. In another example, the data storage engine 412*b* of the data integrator controller 450 of FIG. 4B may store the operational data and the accessory unit data in the non-volatile memory region 414*b*.

Turning to FIG. 2D, in some implementations, if an external network connection is available (270), a network connection is established with a remote computing system (272). The remote computing system, for example, may be the cloud analytics platform 110 of FIG. 1A. The network interface 416*b* of the data integrator controller 450 of FIG. 4B may determine that a network connection is available to the network 422*b* in part through identifying a network connector inserted into the port 452. Alternatively, the data integrator controller 450 may establish a wireless network connection (e.g., Wi-Fi connection) via the wireless interface 418*b*. In other embodiments, the network connection may be enabled via a local device, such as the clinical or mobile application 112 of FIG. 1A executing on a handheld computing device within a local Wi-Fi network of the data integrator. For example, the clinical or mobile application 112, executing on the portable computing device 424*a*, may act as a conduit for delivering the operational data, accessory unit data, and/or data integrator data to the remote server 424*b*, as illustrated in FIG. 4B.

In some implementations, the operational data, accessory unit data, and/or data integrator data are transferred to the remote computing system (274). The data, for example, may be transferred to the cloud analytics platform 110 for storage in the non-volatile memory 116. For example, the communication engine 148 of the cloud analytics platform 110 may enable data transfer with the data integrator 106 for receiving the session data 120, accessory data 122, and/or integrator data 124.

Although described in a particular series of steps, in some implementations of the method 250, more or fewer steps may be performed. For example, in some implementations, rather than storing the operational data and the accessory unit data (268), the data integrator acts as a pass-through device to forward the operational data and the accessory unit data to the remote computing system (274). In another example, rather than forwarding the operational data, accessory unit data, and/or data integrator data (274) as separate data sets, the data integrator, after receiving one or both of the operational data and the accessory unit data, merges the received data (e.g., by timestamps and/or event identifiers) into an integrated data set for forwarding to the remote computing system. In further embodiments, certain steps may be performed in a different order or in parallel. For example, in some implementations, the data integrator establishes the wireless connection with the accessory unit (264) before or at the same time as establishing the wireless connection with the medical device platform (256). Other modifications of the method 250 are possible without exceeding the scope and purpose of the method 250.

Example Medical Device Platform

FIG. 4A illustrates a sample component-level view of an example medical device controller 400, such as the control unit of the medical device platform 102 of FIG. 1A. As shown in FIG. 4A, the medical device controller 400 can include, in some examples, a compression control unit 410, a data storage engine 412*a* and corresponding data store 414*a*, a network interface 416*a*, a short-range wireless interface 418*a*, a user interface 404*a*, at least one power source 420*a*, a sensor interface 408*a*, a peripheral device interface 422*a*, and at least one processor 402*a*. Most or all of the components of the medical device controller 400 may be confined in a same housing of a control unit for a medical device, such as the medical device platform 102 of FIG. 1A.

The data store 414*a* and corresponding data storage circuitry 412*a* can include one or more of non-transitory or non-volatile computer readable media, such as flash memory, solid state memory, magnetic memory, optical memory, cache memory, combinations thereof, and others. The data store 414*a* can be configured to store executable instructions and data used for operation of the medical device controller 400. In certain implementations, the data storage processing circuitry 412*a*, in combination with the data store 414*a*, can include executable instructions that, when executed on the processor 402*a*, are configured to cause the at least one processor 402*a* to perform one or more functions, such as portions of the methods described in relation to FIGS. 2*a*-2D, 3A, and 3B.

In some examples, the network interface 416*a* can facilitate the communication of information between the medical device controller 400 and one or more other devices or entities 424 over a communications network 422*a* (e.g., such as the network 108 of FIGS. 1A and 1B). For example, the network interface 416*a* can be configured to communicate with a portable computing device 424*a* such as a device executing the clinical or mobile application 112 of FIG. 1A. In another example, the network interface 416*a* can be configured to communicate with a remote server 424*b* such as the cloud analytics platform 110 of FIG. 1A.

In some implementations, the medical device controller 400 further includes a wireless interface 418*a* to facilitate communication between the medical device controller 400 and a wireless communication device, such as the portable computing device 424*a* or an accessory unit controller 460, described in greater detail in relation to FIG. 4C or a data integrator controller 450 described in greater detail in relation to FIG. 4B. In some embodiments, the wireless interface 418*a* establishes a short-range communication link such as a Bluetooth, Zigbee, optical connection, or RF communication interface to the accessory unit controller 460 or the portable computing device 424*a*. The wireless interface 418*a*, for example, may perform a portion of the operations described in relation to the wireless communication engine 132*a* of the medical device platform 102 of FIG. 1A.

In some implementations, the medical device controller 400 further includes a peripheral device interface 422*a* for communicating with a peripheral device and/or peripheral data storage 426*a*. The peripheral device and/or peripheral data storage 426*a*, for example, may connect to the medical device controller 400 via a peripheral port 428*a* or coupling. The peripheral device 426*a*, in some embodiments, includes a flash drive or portable computing device for transferring data from the data store 414*a*. In some embodiments, the peripheral device 426*a* may include additional monitoring equipment, such as, in some examples, a pulse monitoring device, respiratory monitoring device, or other biometric collection device. The peripheral device interface 422*a*, for example, may perform a portion of the operations described in relation to the peripheral communication engine 130*a* of the medical device platform 102 of FIG. 1A. In certain embodiments, the port or coupling 428*a* may enable coupling between the medical device controller 400 and the accessory unit controller 460.

In some implementations, the user interface 404*a* includes one or more physical interface devices such as input devices, output devices, and combination input/output devices and a software stack configured to drive operation of the devices. These user interface elements may render visual, audio, and/or tactile content. Thus, the user interface 404*a* may receive input or provide output, thereby enabling a user to interact with the medical device controller 400. In some embodiments, the user interface 404*a* includes visual elements (e.g., function lights 406*a*) such as light emitting diodes (LEDs). Further, in some implementations, the user interface 404*a* includes one or more control buttons 406*b* for providing settings options, activation control, and/or for supplying a response upon the processor triggering an alert regarding an error condition or other alarm. The control buttons 406*b*, in one illustration, may provide mode options for setting the operation of the compression control unit 410. The user interface 404*a*, for example, may perform a portion of the operations described in relation to the I/O engine 138*a* of the medical device platform 102 of FIG. 1A.

The medical device controller 400, in some embodiments, includes the compression control unit 410 for delivering chest compression therapy to a patient via an automated chest compression platform. The compression control unit 410, for example, may control a motor 442 to perform repeated compression cycles when the medical device platform is coupled to a patient's chest. The motor may, for example, be a brushed DC motor.

The medical device controller 400 can also include the power source 420*a* such as at least one battery configured to provide power to one or more components integrated in the medical device controller 400. The power source 420*a* can include a rechargeable multi-cell battery pack, for example. The power source 420*a* may be connected to a rechargeable battery unit for delivering power to the medical device platform 102. In another example, the power source 420*a* may include a separate power source such as an internal lithium battery for powering the medical device controller 400.

The sensor interface 408*a*, in some implementations, is coupled to one or more sensors configured to monitor one or more functional parameters of the medical device platform. For example, the sensors may include an accelerometer 430, a temperature sensor 432*a*, one or more chest compression sensors 434 and/or a global positioning system (GPS) receiver 436. Further, the one or more sensors may include at least one sensor to monitor physiological parameters of the patient. The sensors may be coupled to the medical device controller 400 via a wired or wireless connection.

Once data from the sensors 430, 432*a*, 434, and/or 436 has been received by the sensor interface 408*a*, the data can be directed by the at least one processor 402*a* to a data logging unit 438*a*. The data logging unit 438*a* may archive the data to the data store 414*a*. The data logging unit 438*a*, for example, may perform at least a portion of the operations described in relation to the data logging engine 126*a* of the medical device platform 102 of FIG. 1A. Further, the data from the sensors 430, 432*a*, 434, and/or 436 may be directed by the at least one processor 402*a* to a data management and organization unit 440*b*. The data management and organization unit 440*b*, for example, may calculate metrics from the sensor data and/or combine the sensor data with other data to generate data analytics. The data management and organization unit 440*b*, for example, may perform at least a portion of the operations described in relation to the data archival engine 134*a*, data encryption engine 136, metrics engine 140, and/or session summary engine 142 of the medical device platform 102 of FIG. 1A. The data store 414*a*, for example, may maintain a portion of the data described in relation to the non-volatile memory 114*a* of the medical device platform 102 of FIG. 1A.

In some implementations, the at least one processor 402*a* includes one or more processors (or one or more processor cores) that each are configured to perform a series of instructions that result in manipulated data and/or control the operation of the other components of the medical device controller 400. In some implementations, when executing a specific process (e.g., monitoring of chest compressions), the at least one processor 402*a* can be configured to make specific logic-based determinations based on input data received, and be further configured to provide one or more outputs that can be used to control or otherwise inform subsequent processing to be carried out by the at least one processor 402*a* and/or other processors or circuitry with which processor 402*a* is communicatively coupled. Thus, the at least one processor 402*a* reacts to specific input stimulus in a specific way and generates a corresponding output based on that input stimulus. In some example cases, the at least one processor 402*a* can proceed through a sequence of logical transitions in which various internal register states and/or other bit cell states internal or external to the at least one processor 402*a* may be set to logic high or logic low. As referred to herein, the at least one processor 402*a* can be configured to execute a function where software is stored in a data store coupled to the at least one processor 402*a* (e.g., the data store 414*a*), the software being configured to cause the at least one processor 402*a* to proceed through a sequence of various logic decisions that result in the function being executed. The various components that are described herein as being executable by the at least one processor 402*a* can be implemented in various forms of specialized hardware, software, or a combination thereof. For example, the at least one processor can be a digital signal processor (DSP) such as a 24-bit DSP processor. The at least one processor 402*a* can be a multi-core processor, e.g., having two or more processing cores. The at least one processor 402*a* can be an Advanced RISC Machine (ARM) processor such as a 32-bit ARM processor. The at least one processor 402*a* can execute an embedded operating system, and include services provided by the operating system that can be used for file system manipulation, display & audio generation, basic networking, firewalling, data encryption and communications.

Figure 5A:
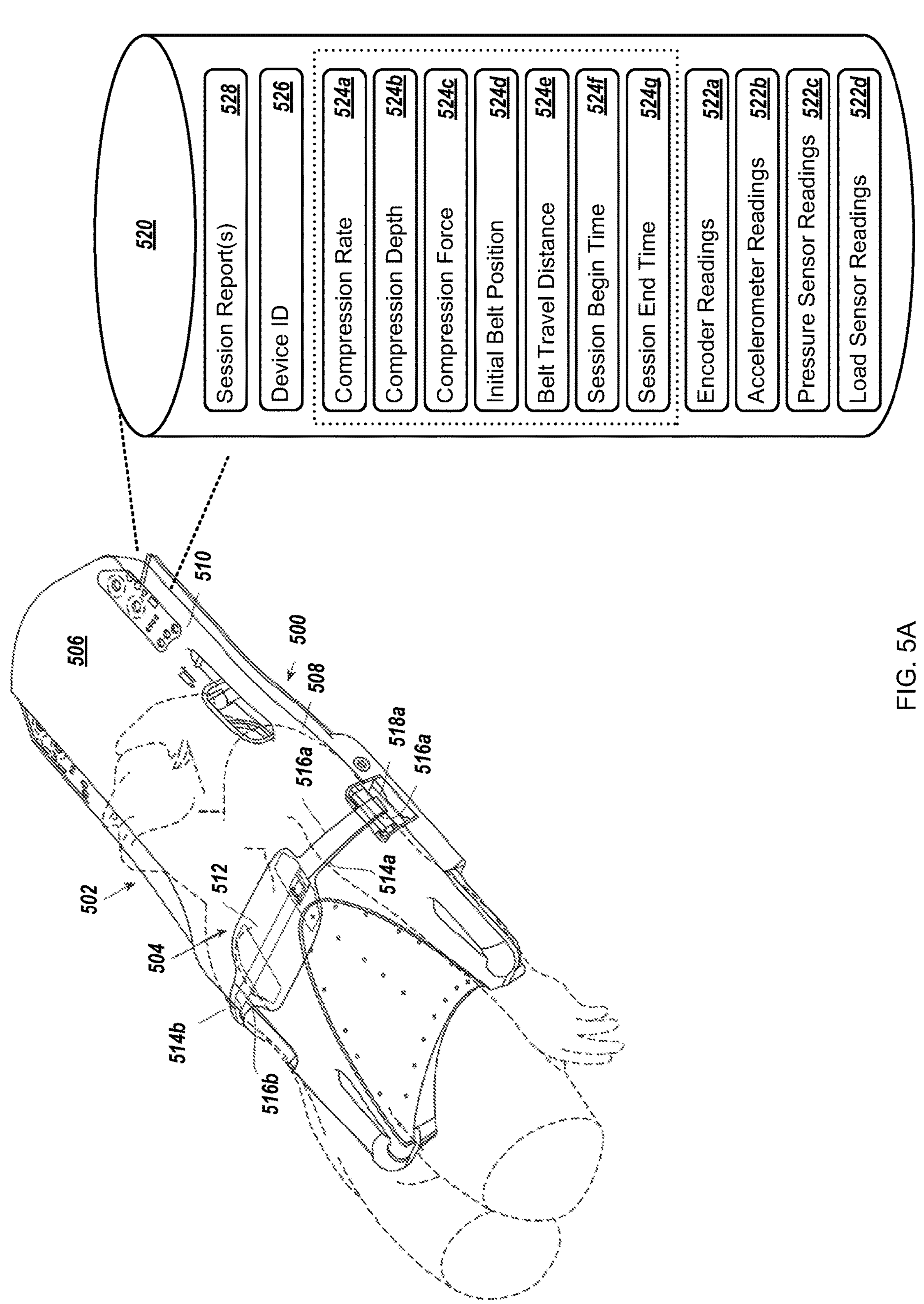
FIG. 5A is an example of a belt type automated chest compression platform and example data collected and calculated by a controller of the platform.

Turning to FIG. 5A an example belt-style chest compression medical device platform 500 is illustrated, releasably coupled to a patient 502. The chest compression device 500 is designed to apply therapeutic chest compressions to the patient 502 with a compression belt 504. The chest compression device 500 includes a belt drive platform 506 configured for placement under at least the thorax of the patient, upon which the patient lies during delivery of therapy by the chest compression device 500.

The belt drive platform 506, in some implementations, includes a housing 508 for a motor, drive train, and/or control system (e.g., the medical device controller 400 of FIG. 4A) for the device 500. The control system, in other embodiments, may be provided elsewhere in the device 500.

Operation of the device 500, in some implementations, can be initiated and adjusted by a user through a control panel 510 and/or a display operated by the control system to provide feedback regarding the status of the device 500 to the user. The control panel 510, for example, may present the function lights 406*a* and/or control button 406*b* of FIG. 4A for user I/O interfacing with the medical device controller 400. A compression cycle of the device 500 includes a downstroke, an upstroke (a release portion), and possibly some period of delay between a downstroke and a successive upstroke and/or between an upstroke and a successive downstroke.

During operation of the chest compression device 500, the control system (e.g., medical device controller 400 of FIG. 4A), in some implementations, operates to take up slack in the belt 504 upon initial start-up, equates a position within the drive train of the device or upon the belt 504 itself with a slack take-up position, and configures the compression cycle to begin each downstroke from this position.

The compression belt 504, in some implementations, includes a load-distribution section 512 at the mid-portion of the belt as well as left and right belt ends 514*a* and 514*b* (illustrated in part as narrow pull straps 516*a* and 516*b*), which serve as tensioning portions extending from the load distributing portion 512, posteriorly relative to the patient 502, to drive spools within or on the housing of the platform 506. When fitted on the patient 502, the load distribution section 512 is disposed over the anterior chest wall of the patient 502, and the left and right belt ends 514*a* and 514*b* extend posteriorly over the right and left axilla of the patient 502 to connect to their respective lateral drive spools (e.g., such as spool 518*a*, the right drive spool not being visible in the figure).

During operation of the compression device platform 500, in some implementations, the controller collects data (e.g., from a number of sensors upon or within the compression device platform 500) and derives metrics therefrom to store within a non-volatile storage region 520 (such as the non-volatile memory 114*a* of the medical device platform 102 of FIG. 1A). The data, for example, may be logged by the data logging engine 126*a* of FIG. 1A, archived to the non-volatile storage region 520 by the data archival engine 134*a*, and combined into metrics by the metrics engine 140.

As illustrated, in some implementations, the non-volatile storage medium 520 stores sensor data 522 such as, in some examples, a set of linear or rotary encoder readings 522*a*, a set of accelerometer readings 522*b*, a set of pressure sensor readings 522*c*, and a set of load sensor readings 522*d*. The sensor data, in some implementations, is combined to calculate metrics 524 such as, in some examples, a compression rate 524*a*, a compression depth 524*b*, a compression force 524*c*, an initial belt position 524*d*, and a belt travel distance 524*e*. The various data and metrics may each include a corresponding timestamp during the therapy session, having a session begin time 524*f* and a session end time 524*g* determined, for example, based upon one or more control signals (e.g., user interface selections, etc.) received by the automated chest compression platform 500. The non-volatile storage medium 520, in further examples, may maintain device specific data such as a device identifier 526 and/or one or more session reports 528 (e.g., including summaries of at least a portion of the metrics 524).

Figure 5B:
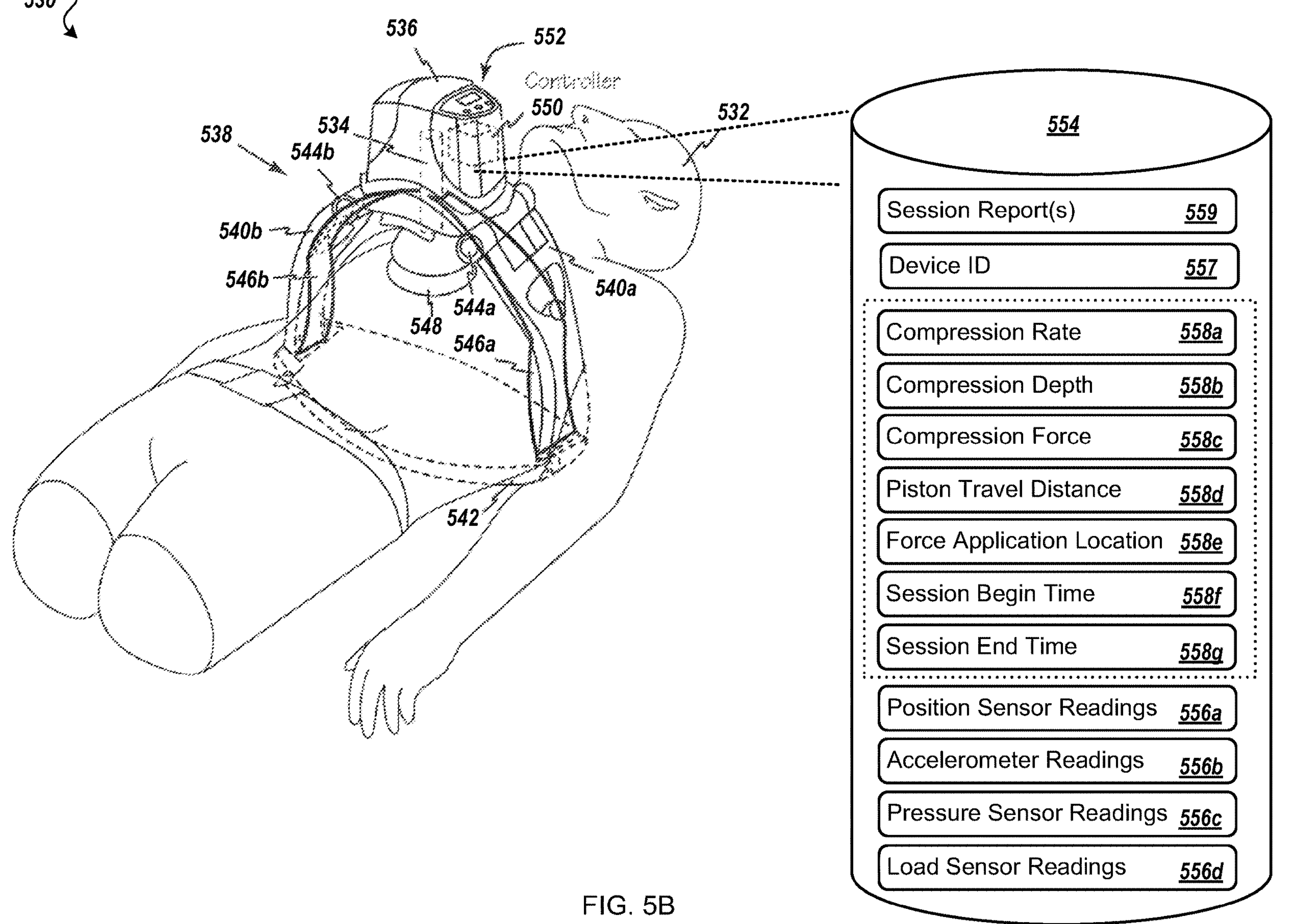
FIG. 5B is an example of a piston type automated chest compression platform and example data collected and calculated by a controller of the platform.
Figure 5C:
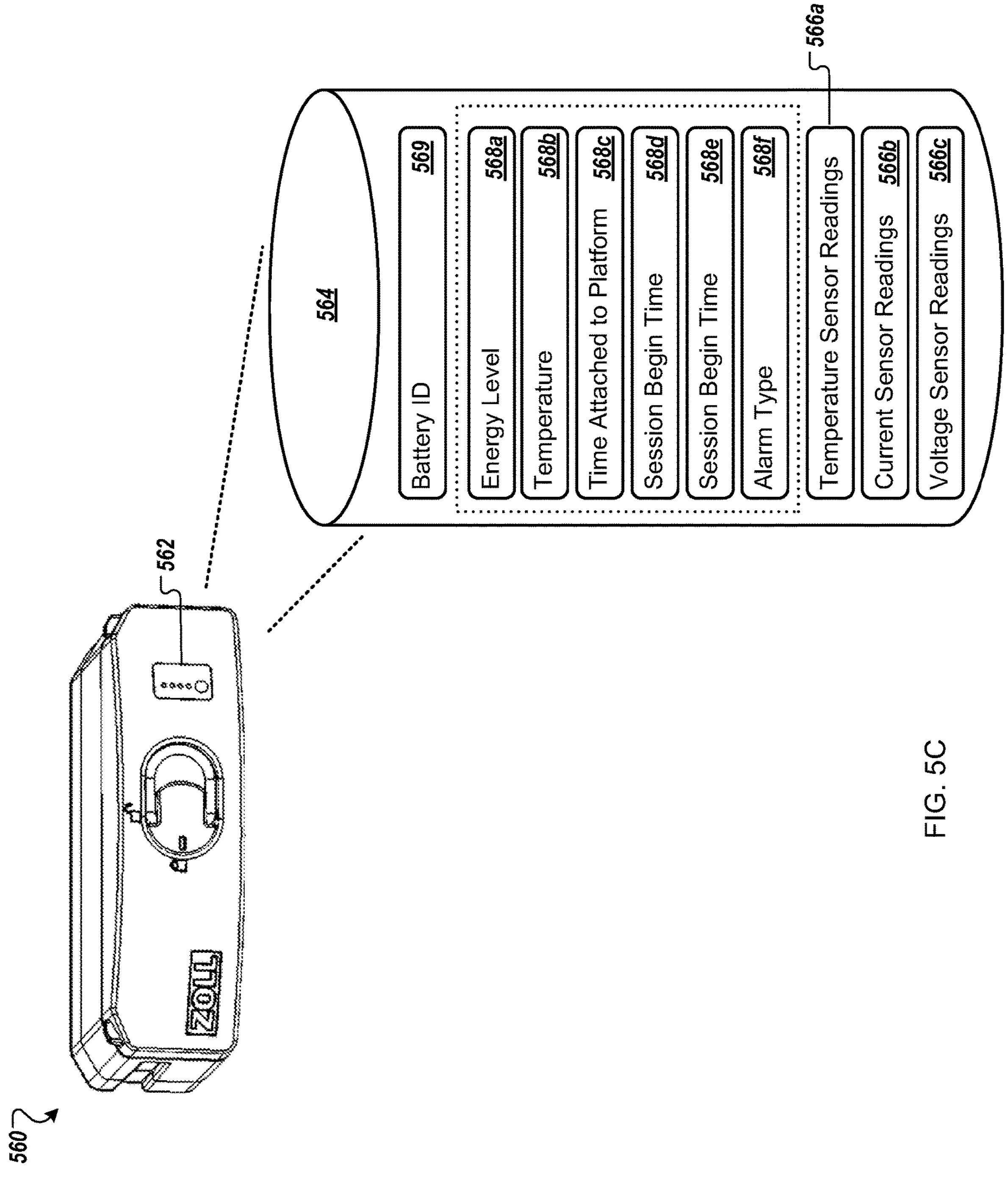
FIG. 5C is an example of a rechargeable power supply type accessory unit and example data collected and calculated by a controller of the accessory unit.
Figure 5D:
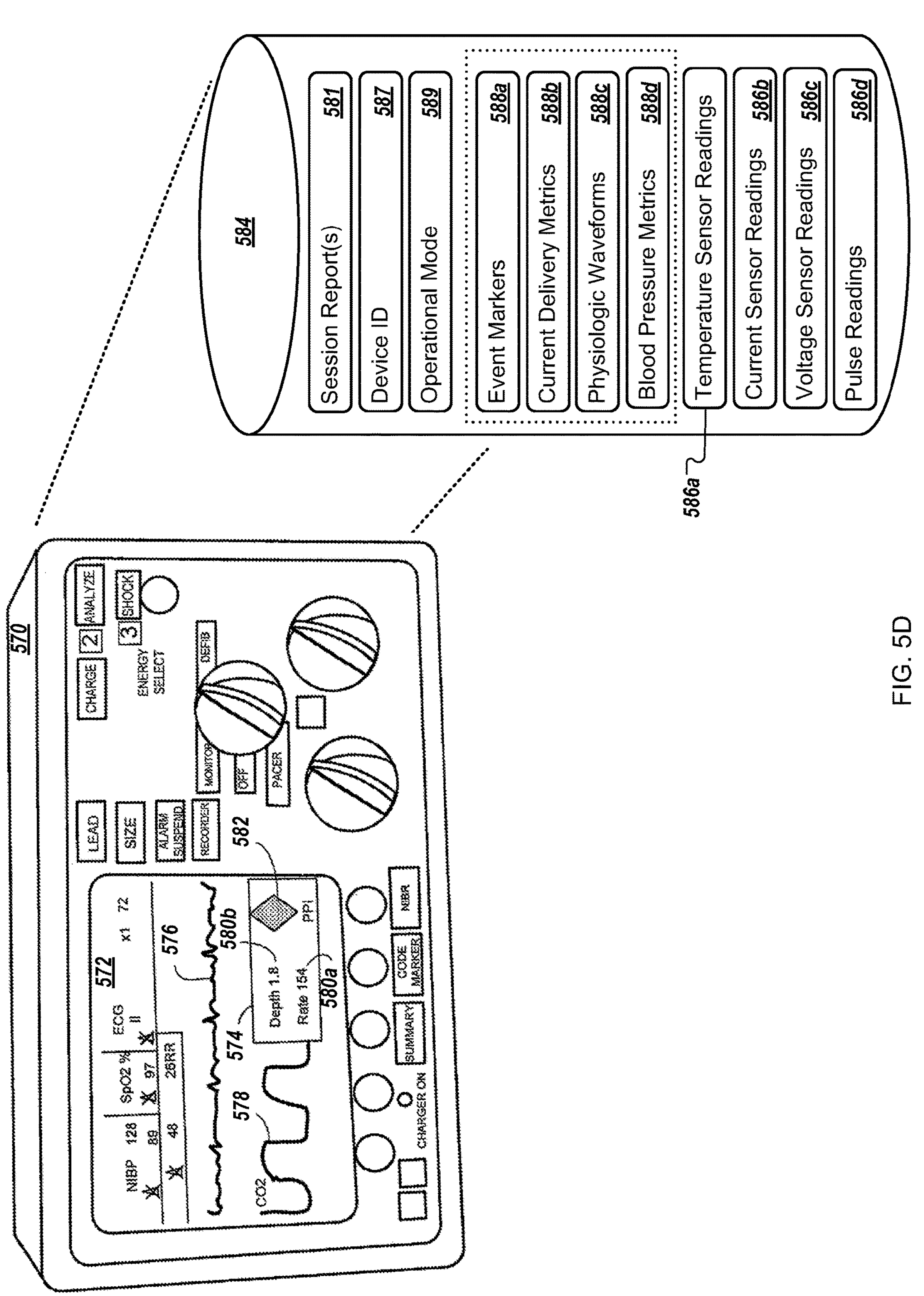
FIG. 5D is an example of a defibrillator type data integrator and example data collected and calculated by a controller of the data integrator.
Figure 5E:
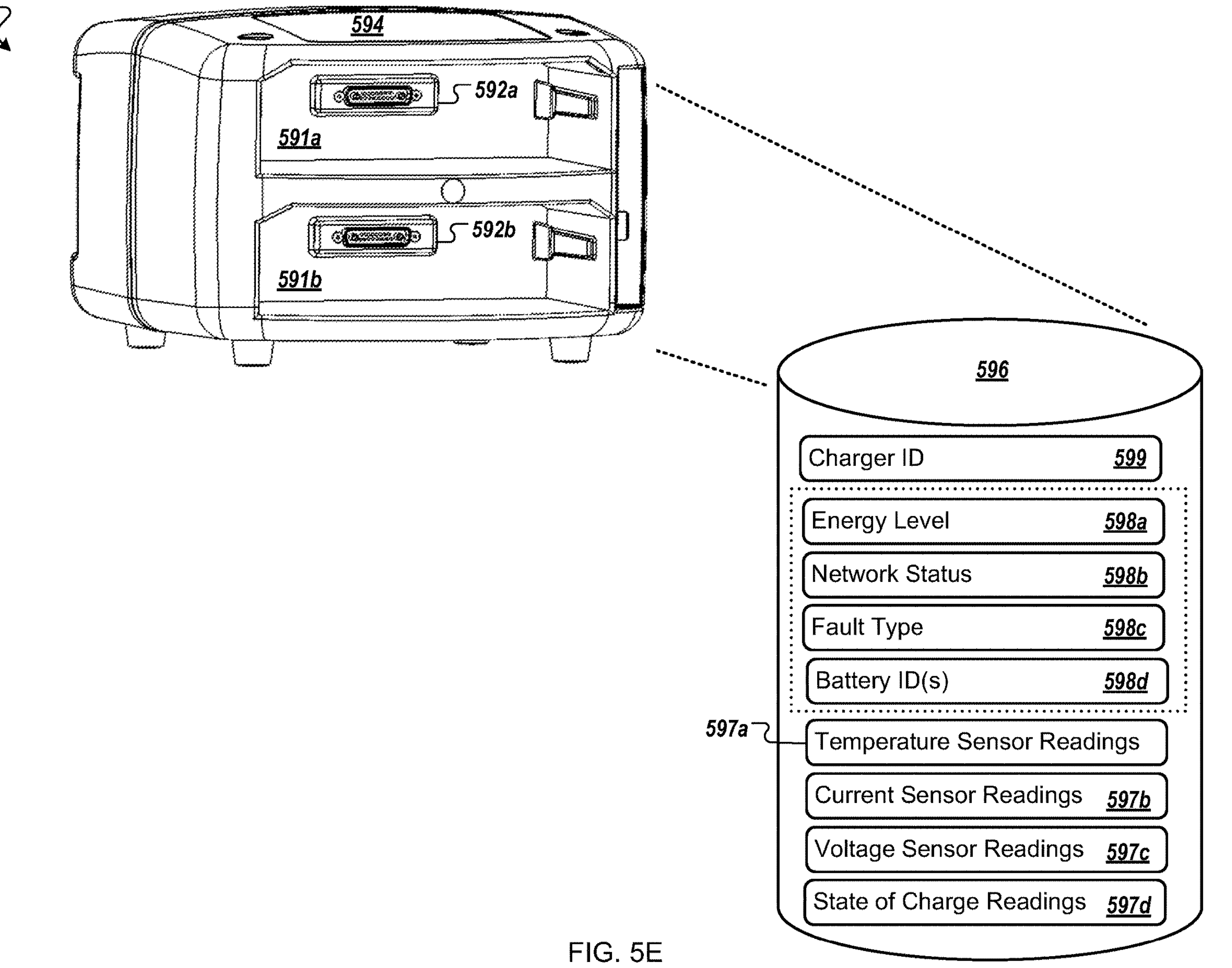
FIG. 5E is an example of a charging station type data integrator for charging rechargeable power supply units and example data collected and calculated by a controller of the data integrator.

In some embodiments, turning to FIG. 5B, the medical device platform is a piston style compression unit such as an example piston-style chest compression medical device platform 530 of FIG. 5B, releasably coupled to a patient 532. The chest compression device 530 may be configured to apply compressions with a piston 534. The piston 534, as illustrated, is disposed within a compression unit 536 which is supported over the patient with a frame or gantry 538 having two support legs 540*a* and 540*b*. The support legs 540*a*, 540*b* may be fixed to a backboard or support platform 542. In other embodiments (not illustrated), the support legs 540*a*, 540*b* may be fixed to a gurney or transport cot.

The compression unit 536, in some implementations, is connected to the support legs 540*a*, 540*b* at hinges 544*a* and 544*b*. Leaf springs 546*a* and 546*b*, in some embodiments, are operably connected between the piston 534 and either the backboard 542 or to the support legs 540*a*, 540*b* through the hinges 544*a* and 544*b*. The leaf springs 546*a* and 546*b* may be formed of a single layer of material or they may be formed of two or more layers or two or more parallel springs.

When disposed about the patient, the frame 538 extends over thorax of the patient 532 so that the piston 534 is disposed opposing a sternum of the patient 532 to contact the patient's chest directly over the sternum, to impart compressive force on the sternum of the patient 532. The piston 534 may include a removable compression pad 548 adapted to contact the patient's chest. The piston 534, for example, may be driven by the motor 442 of the medical device controller 400 of FIG. 4A.

The chest compression device 530, in some embodiments, is controlled using a controller 550, such as the medical device controller 400 of FIG. 4A. The controller 550 may be operated by a clinical user through an interface 552. The user interface 552, for example, may include a display to provide instructions and prompts to a rescuer as well as an input device to accept operating instructions from the rescuer. The user interface 552 may include the function lights 406*a* and/or the control button(s) 406*b* of the medical device controller 400 of FIG. 4A.

During operation of the compression device platform 530, in some implementations, the controller 550 collects data (e.g., from a number of sensors upon or within the compression device platform 530) and derives metrics therefrom to store within a non-volatile storage region 554 (such as the non-volatile memory 114*a* of the medical device platform 102 of FIG. 1A). The data, for example, may be logged by the data logging engine 126*a* of FIG. 1A, archived to the non-volatile storage region 520 by the data archival engine 134*a*, and combined into metrics by the metrics engine 140.

As illustrated, in some implementations, the non-volatile storage medium 554 stores sensor data 556 such as, in some examples, a set of linear or rotary encoder readings 556*a*, a set of accelerometer readings 556*b*, a set of pressure sensor readings 556*c*, and a set of load sensor readings 556*d*. The sensor data, in some implementations, is combined to calculate metrics 558 such as, in some examples, a compression rate 558*a*, a compression depth 558*b*, a compression force 558*c*, a piston travel distance 558*d*, and/or a force application location 558*e*. The various data and metrics may each include a corresponding timestamp during the therapy session, having a session begin time 558*f* and a session end time 558*g* determined, for example, based upon one or more control signals (e.g., user interface selections, etc.) received by the automated chest compression platform 530. The non-volatile storage medium 554, in further examples, may maintain device specific data such as a device identifier 557 and/or one or more session reports 559 (e.g., including summaries of at least a portion of the metrics 558).

Example Accessory Unit

FIG. 4C illustrates a sample component-level view of an example accessory unit controller 460, such as the control unit of the accessory unit 104 of FIG. 1A. As shown in FIG. 4C, the accessory unit controller 400 can include, in some examples, a data storage engine 412*c* and corresponding data store 414*c*, a wireless interface 418*c*, a user interface 404*c*, at least one power source 420*c*, a sensor interface 408*c*, a peripheral device interface 422*c*, and at least one processor 402*c*. Most or all of the components of the accessory unit controller 460 may be confined in a same housing of a control unit for an accessory unit, such as the accessory unit 104 of FIG. 1A.

The data store 414*c* and corresponding data storage circuitry 412*c* can include one or more of non-transitory or non-volatile computer readable media, such as flash memory, solid state memory, magnetic memory, optical memory, cache memory, combinations thereof, and others. The data store 414*c* can be configured to store executable instructions and data used for operation of the accessory unit controller 460. In certain implementations, the data storage processing circuitry 412*c*, in combination with the data store 414*c*, can include executable instructions that, when executed on the processor 402*c*, are configured to cause the at least one processor 402*c* to perform one or more functions, such as portions of the methods described in relation to FIGS. 2A-2D, 3A, and 3B.

In some implementations, the accessory unit controller 460 further includes the wireless interface 418*c* to facilitate communication between the accessory unit controller 460 and a wireless communication device, such as the data integrator controller 450 of FIG. 4B or the medical device controller 400 of FIG. 1A. In some embodiments, the wireless interface 418*c* establishes a short-range communication link such as a Bluetooth, Zigbee, optical connection, or RF communication interface to the data integrator controller 450 of FIG. 4B or the medical device controller 400 of FIG. 1A. The wireless interface 418*c*, for example, may perform a portion of the operations described in relation to the wireless communication engine 132*b* of the accessory unit 104 of FIG. 1A.

In some implementations, the accessory unit controller 460 includes a peripheral device interface 422*c* for communicating directly with a coupled device, such as the data integrator controller 450 of FIG. 4B or the medical device controller 400 of FIG. 1A. For example, the peripheral device interface 422*c* may couple to the data integrator controller 450 and/or the medical device controller 400 via a port or coupling 462. The peripheral device interface 422*c*, for example, may perform a portion of the operations described in relation to the peripheral communication engine 130*b* of the accessory unit 104 of FIG. 1A.

In some implementations, the user interface 404*c* includes one or more physical interface devices such as input devices, output devices, and combination input/output devices and a software stack configured to drive operation of the devices. These user interface elements may render visual, audio, and/or tactile content. Thus, the user interface 404*c* may receive input or provide output, thereby enabling a user to interact with the accessory unit controller 460. In some embodiments, the user interface 404*c* includes visual elements (e.g., function lights 406*e*) such as light emitting diodes (LEDs). Further, in some implementations, the user interface 404*a* includes one or more control buttons 406*f* for providing settings options, activation control, and/or for supplying a response upon the processor triggering an alert regarding an error condition or other alarm.

The accessory unit controller 460 can also include the power source 420*c* such as at least one battery configured to provide power to one or more components integrated in the accessory unit controller 460. The power source 420*c* can include a rechargeable multi-cell battery pack, for example. The accessory unit 104 may be a rechargeable battery unit, and the power source 420*c* may be connected to a rechargeable battery for delivering power to the accessory unit controller 460. In another example, the power source 420*c* may include a separate power source such as an internal lithium battery for powering the accessory unit controller 460.

The sensor interface 408*c*, in some implementations, is coupled to one or more sensors configured to monitor one or more functional parameters of the accessory unit 104. For example, the sensors may include a temperature sensor 432*c* and/or one or more accessory unit monitoring sensors 464. Further, in embodiments where the accessory unit is a therapy delivery device such as a defibrillator unit or a ventilator unit, the one or more sensors may include at least one sensor to monitor physiological parameters of the patient. The sensors 432*c*, 464 may be coupled to the accessory unit controller 460 via a wired or wireless connection.

Once data from the sensors 432*c*, 464 has been received by the sensor interface 408*c*, the data can be directed by the at least one processor 402*c* to a data logging unit 438*c*. The data logging unit 438*c* may archive the data to the data store 414*c*. The data logging unit 438*c*, for example, may perform at least a portion of the operations described in relation to the data logging engine 126*b* of the accessory unit 104 of FIG. 1A. Further, the data from the sensors 432*c*, 464 may be directed by the at least one processor 402*c* to a data management and organization unit 440*c*. The data management and organization unit 440*c*, for example, may calculate metrics from the sensor data and/or combine the sensor data with other data to generate data analytics. The data management and organization unit 440*c*, for example, may perform at least a portion of the operations described in relation to the data archival engine 134*b* of the accessory unit 104 of FIG. 1A. The data store 414*c*, for example, may maintain a portion of the data described in relation to the non-volatile memory 114*b* of the accessory unit 104 of FIG. 1A.

In some implementations, the at least one processor 402*c* includes one or more processors (or one or more processor cores) that each are configured to perform a series of instructions that result in manipulated data and/or control the operation of the other components of the accessory unit controller 460. In some implementations, when executing a specific process (e.g., monitoring defibrillation or ventilation of a medical device accessory unit), the at least one processor 402*c* can be configured to make specific logic-based determinations based on input data received, and be further configured to provide one or more outputs that can be used to control or otherwise inform subsequent processing to be carried out by the at least one processor 402*c* and/or other processors or circuitry with which processor 402*c* is communicatively coupled. Thus, the at least one processor 402*c* reacts to specific input stimulus in a specific way and generates a corresponding output based on that input stimulus. In some example cases, the at least one processor 402*c* can proceed through a sequence of logical transitions in which various internal register states and/or other bit cell states internal or external to the at least one processor 402*c* may be set to logic high or logic low. As referred to herein, the at least one processor 402*c* can be configured to execute a function where software is stored in a data store coupled to the at least one processor 402*c* (e.g., the data store 414*c*), the software being configured to cause the at least one processor 402*c* to proceed through a sequence of various logic decisions that result in the function being executed. The various components that are described herein as being executable by the at least one processor 402*c* can be implemented in various forms of specialized hardware, software, or a combination thereof. For example, the at least one processor can be a digital signal processor (DSP) such as a 24-bit DSP processor. The at least one processor 402*c* can be a multi-core processor, e.g., having two or more processing cores. The at least one processor 402*c* can be an Advanced RISC Machine (ARM) processor such as a 32-bit ARM processor. The at least one processor 402*c* can execute an embedded operating system, and include services provided by the operating system that can be used for file system manipulation, display & audio generation, basic networking, firewalling, data encryption and communications.

In some embodiments, the accessory unit 104 is a defibrillation unit, and the processor 402*c* is coupled to one or more electrodes configured to provide therapy to the patient. For example, the at least one processor 402*c* can include, or be operably connected to, circuitry components that are configured to generate and provide the therapeutic shock. The circuitry components can include, for example, resistors, capacitors, relays and/or switches, electrical bridges such as an h-bridge (e.g., including multiple insulated gate bipolar transistors or IGBTs), voltage and/or current measuring components, and other similar circuitry components arranged and connected such that the circuitry components work in concert with the therapy delivery circuit and under control of the at least one processor 402*c* to provide, for example, one or more pacing or defibrillation therapeutic pulses. As the energy is delivered to the patient, the amount of energy being delivered can be tracked via accessory sensors 464. For example, the amount of energy can be kept to a predetermined constant value even as the pulse waveform is dynamically controlled based on factors such as the patient's body impedance to which the pulse is being delivered.

Turning to FIG. 5C, in some embodiments, the accessory unit is a rechargeable battery accessory such as an example rechargeable battery unit 560. The rechargeable battery unit 560, for example, may be configured to be inserted into a battery compartment of a medical device platform, such as the belt-style compression platform 500 of FIG. 5A or the piston-style compression platform 530 of FIG. 5B. The rechargeable battery unit 560 may include a retention mechanism, such as a latch, to engage a receiver within a battery compartment of the medical device platform to releasable retain the rechargeable battery unit 560 within the medical device platform.

In some implementations, the rechargeable battery unit 560 includes a connection mechanism configured to connect with a connector within battery compartment 121 of the medical device platform for establishing electrical communication between the medical device controller (e.g., the medical device controller 400 of FIG. 4A) of the mechanical compression device platform and the rechargeable battery unit 560. The connector, in some embodiments, not only allows for the flow of current from the rechargeable battery unit 560 to power the mechanical compression device, but also provides for the sharing of data, programming commands and/or other information, such as battery charge status, discharge rate, time remaining until discharged, and the like between the rechargeable battery unit 560 and the medical device platform controller. Similarly, connector may be configured for releasable connection to a connector in a battery charging unit, such as a battery charger style data integrator 590 described in relation to FIG. 5E, to charge the cells of the rechargeable battery unit 560, as well as to provide for the sharing of data, software programs or commands and/or other information between the battery charging unit and the rechargeable battery unit 560.

In some implementations, the rechargeable battery unit 560 further includes a connection mechanism or data transfer mechanism (e.g., transmitter and/or receiver) for communicatively connecting the rechargeable battery unit 560 to a communication network that would allow for sharing of information between the rechargeable battery unit 560 and other devices such as computing devices, servers, processors and/or storage mediums. The rechargeable battery unit 560 may be configured to communicate with a portion of such devices via a network. The network may be a wired network, such as, for example, an Ethernet, or it may be a wireless network. The network may be a local network, or it may be a wide area network, such as a WLAN or the Internet. Further, the network may be a short-range wireless network, such as a Wi-Fi network or a radio frequency (RF) (e.g., Bluetooth, optical, or Zigbee) network.

In some implementations, the rechargeable battery unit 560 includes a user interface 562. The user interface 562 may include one or more status indicators, such as one or more light emitting diodes (LEDs) or function lights (e.g., such as function lights 406*e* of the accessory unit controller 460 of FIG. 4C). The status indicators may provide a visual indication of, for example, the charge/discharge status of the rechargeable battery unit 560, the presence of any faults that would affect the operation of the rechargeable battery unit 560, or other information that might be useful to the user of the rechargeable battery unit 560.

A control button, in some implementations, is also included in the user interface 562. The control button, such as the control button(s) 406*f* of the accessory unit controller 460 of FIG. 4C, may be used, for example, to initiate a reset of the rechargeable battery unit 560. In another example, the control button may be used to initiate a diagnostic test, the results of which may be indicated by at least one of the status indicators. In further examples, the control button may be used to initiate other functions of the controller (e.g., controller 460 of FIG. 4C) in the rechargeable battery unit 560, such as determining a remaining capacity of the battery and/or displaying fault codes.

In some implementations, the controller of the rechargeable battery unit 560 (e.g., the controller 460 of FIG. 4C) collects data (e.g., from a number of sensors upon or within the rechargeable battery unit 560) and derives metrics therefrom to store within a non-volatile storage region 564 (such as the non-volatile memory 114*b* of the accessory unit 104 of FIG. 1A). The data, for example, may be logged by the data logging engine 126*b* of FIG. 1A and archived to the non-volatile storage region 564 by the data archival engine 134*b*. The data may further be combined into metrics, in some embodiments, by the controller of the rechargeable battery unit 560.

As illustrated, in some implementations, the non-volatile storage medium 564 stores sensor data 566 such as, in some examples, a set of temperature sensor readings 566*a*, a set of current sensor readings 566*b*, and/or a set of voltage sensor readings 566*c*. The sensor data, in some implementations, is combined to calculate metrics 568 such as, in some examples, an energy level 568*a* and a temperature 568*b*. The various data and metrics may each include a corresponding timestamp during the therapy session, having a session begin time 568*d* and a session end time 568*e* determined, for example, based upon one or more control signals (e.g., user interface selections, etc.) received by the rechargeable battery unit 560 (e.g., from the automated chest compression platform 500) or, alternatively, representing a begin time of attachment to the platform and an end time of attachment to the platform. The non-volatile storage medium 564, in further examples, may maintain device specific data such as a battery identifier 569.

Example Data Integrator

FIG. 4B illustrates a sample component-level view of an example data integrator controller 450, such as the control unit of the data integrator 106 of FIG. 1A. As shown in FIG. 4B, the data integrator controller 450 can include, in some examples, a data storage engine 412*b* and corresponding data store 414*b*, a network interface 416*b*, a short-range wireless interface 418*b*, a user interface 404*b*, at least one power source 420*b*, a sensor interface 408*b*, a peripheral device interface 422*b*, and at least one processor 402*b*. Further, in some embodiments, the data integrator controller 450 includes a charging control unit 454 for controlling a recharging operation for one or more battery unit power sources 456. Most or all of the components of the data integrator controller 450 may be confined in a same housing of a control unit for the data integrator, such as the data integrator 106 of FIG. 1A.

The data store 414*b* and corresponding data storage circuitry 412*b* can include one or more of non-transitory or non-volatile computer readable media, such as flash memory, solid state memory, magnetic memory, optical memory, cache memory, combinations thereof, and others. The data store 414*b* can be configured to store executable instructions and data used for operation of the data integrator controller 450. In certain implementations, the data storage processing circuitry 412*b*, in combination with the data store 414*b*, can include executable instructions that, when executed on the processor 402*b*, are configured to cause the at least one processor 402*b* to perform one or more functions, such as portions of the methods described in relation to FIGS. 2A-2D, 3A, and 3B.

In some examples, the network interface 416*b* can facilitate the communication of information between the data integrator controller 450 and one or more other devices or entities 424 over a communications network 422*b* (e.g., such as the network 108 of FIGS. 1A and 1B). For example, the network interface 416*b* can be configured to communicate with the portable computing device 424*a* such as a device executing the clinical or mobile application 112 of FIG. 1A. In another example, the network interface 416*b* can be configured to communicate with the remote server 424*b* such as the cloud analytics platform 110 of FIG. 1A. The network interface 416*b*, for example, can connect to the network 422*b* via a network port 452

In some implementations, the data integrator controller 450 further includes a wireless interface 418*b* to facilitate communication between the data integrator controller 450 and a wireless communication device, such as the portable computing device 424*a* or an accessory unit controller 460, described in greater detail in relation to FIG. 4C or the medical device platform controller 400 described in greater detail in relation to FIG. 4A. In some embodiments, the wireless interface 418*b* establishes a short-range RF communication link such as a Bluetooth, Zigbee or optical communication interface to the accessory unit controller 460 or the portable computing device 424*a*. The wireless interface 418*b*, for example, may perform a portion of the operations described in relation to the wireless communication engine 132*c* of the data integrator 106 of FIG. 1A.

In some implementations, the data integrator controller 450 further includes a peripheral device interface 422*b* for communicating with a peripheral device and/or peripheral data storage 426*b*. The peripheral device and/or peripheral data storage 426*b*, for example, may connect to the data integrator controller 450 via a peripheral port 428*b*. The peripheral device 426*b*, in some embodiments, includes a flash drive or portable computing device for transferring data from the data store 414*b*. In some embodiments, the peripheral device 426*b* may include additional monitoring equipment, such as, in some examples, a pulse monitoring device, respiratory monitoring device, or other biometric collection device. The additional monitoring equipment, in some examples, may be an accessory unit coupled to the data integrator controller 450 via the accessory unit controller 460. In certain embodiments, the port or coupling 428*b* may enable coupling between the data integrator controller 450 and the accessory unit controller 460. The peripheral device interface 422*b*, for example, may perform a portion of the operations described in relation to the peripheral communication engine 130*c* of the data integrator 106 of FIG. 1A.

In some implementations, the user interface 404*b* includes one or more physical interface devices such as input devices, output devices, and combination input/output devices and a software stack configured to drive operation of the devices. These user interface elements may render visual, audio, and/or tactile content. Thus, the user interface 404*b* may receive input or provide output, thereby enabling a user to interact with the data integrator controller 450. In some embodiments, the user interface 404*b* includes visual elements (e.g., function lights 406*c*) such as light emitting diodes (LEDs). Further, in some implementations, the user interface 404*b* includes one or more control buttons 406*d* for providing settings options, activation control, and/or for supplying a response upon the processor triggering an alert regarding an error condition or other alarm. The user interface 404*b*, for example, may perform a portion of the operations described in relation to the I/O engine 138*b* of the data integrator 106 of FIG. 1A.

The data integrator controller 450, in some embodiments, includes the charging control unit 454 for controlling charging of one or more rechargeable battery unit power sources 456. For example, the data integrator 106 may be a charging unit for rechargeable batteries used by the medical device platform 102. In another example, the data integrator 106 may be a docking station for the accessory unit 104, such as a portable computing device.

The data integrator controller 450 can also include the power source 420*b* such as at least one battery configured to provide power to one or more components integrated in the data integrator controller 450. The power source 420*b* can include a rechargeable multi-cell battery pack, for example. The power source 420*b* may be connected to a rechargeable battery unit for delivering power to the data integrator 450. In another example, the power source 420*b* may include a separate power source such as an internal lithium battery for powering the data integrator controller 450.

The sensor interface 408*b*, in some implementations, is coupled to one or more sensors configured to monitor one or more functional parameters of the data integrator (e.g., the data integrator 106 of FIG. 1A). For example, the sensors may include, a temperature sensor 432*b* and/or one or more medical device sensors 458*a*. The sensors may be coupled to the data integrator 450 via a wired or wireless connection.

Once data from the sensors (e.g., sensors 432*b*, 458*a*) has been received by the sensor interface 408*b*, the data can be directed by the at least one processor 402*b* to a data logging unit 438*b*. The data logging unit 438*b* may archive the data to the data store 414*b*. The data logging unit 438*b*, for example, may perform at least a portion of the operations described in relation to the data logging engine 126*c* of the data integrator 106 of FIG. 1A. Further, the data from the sensors (e.g., sensor 432*b*, 458*a*) may be directed by the at least one processor 402*b* to a data management and organization unit 440*b*. The data management and organization unit 440*b*, for example, may calculate metrics from the sensor data and/or combine the sensor data with other data to generate data analytics. The data management and organization unit 440*b*, for example, may perform at least a portion of the operations described in relation to the data archival engine 134*c*, data logging engine 126*c* and/or data merging engine 144 of the data integrator 106 of FIG. 1A. The data store 414*b*, for example, may maintain a portion of the data described in relation to the non-volatile memory 114*c* of the data integrator 106 of FIG. 1A.

In some implementations, the at least one processor 402*b* includes one or more processors (or one or more processor cores) that each are configured to perform a series of instructions that result in manipulated data and/or control the operation of the other components of the data integrator controller 450. In some implementations, when executing a specific process (e.g., monitoring of chest compressions), the at least one processor **402*b* can be configured to make specific logic-based determinations based on input data received, and be further configured to provide one or more outputs that can be used to control or otherwise inform subsequent processing to be carried out by the at least one processor 402*b* and/or other processors or circuitry with which processor 402*b* is communicatively coupled. Thus, the at least one processor 402*b* reacts to specific input stimulus in a specific way and generates a corresponding output based on that input stimulus. In some example cases, the at least one processor 402*b* can proceed through a sequence of logical transitions in which various internal register states and/or other bit cell states internal or external to the at least one processor 402*b* may be set to logic high or logic low. As referred to herein, the at least one processor 402*b* can be configured to execute a function where software is stored in a data store coupled to the at least one processor 402*b* (e.g., the data store 414*b*), the software being configured to cause the at least one processor 402*b* to proceed through a sequence of various logic decisions that result in the function being executed. The various components that are described herein as being executable by the at least one processor 402*b* can be implemented in various forms of specialized hardware, software, or a combination thereof. For example, the at least one processor can be a digital signal processor (DSP) such as a 24-bit DSP processor. The at least one processor 402*b* can be a multi-core processor, e.g., having two or more processing cores. The at least one processor 402*b* can be an Advanced RISC Machine (ARM) processor such as a 32-bit ARM processor. The at least one processor 402*b*** can execute an embedded operating system, and include services provided by the operating system that can be used for file system manipulation, display & audio generation, basic networking, firewalling, data encryption and communications.

Data Integrator as a Defibrillator

The data integrator, in some embodiments, is a defibrillation unit. Turning to FIG. 5D, an example portable defibrillation unit 570 is illustrated. The defibrillation unit 570 includes a display portion 572 that provides information about patient status and CPR administration quality during the use of the defibrillation unit 570. The defibrillation unit 570 may collect various data and display the data in an efficient and effective manner to a clinical user via the display 572. As shown on display 572, during the administration of chest compressions, the defibrillation unit 570 displays information about the chest compressions in box 574 on the same display 572 as a filtered ECG waveform 576 and a CO2 waveform 578 (alternatively a SpO2 waveform can be displayed).

During chest compressions, the ECG waveform 576, in some embodiments, generated by gathering ECG data point and accelerometer readings from ECG electrodes and an accelerometer sensor (e.g., by the sensor interface **408*b* as data from medical device sensors 458*a*, as described in relation to FIG. 4B) and filtering the motion induced (e.g., CPR induced) noise from the ECG waveform (e.g., by the data management and organization engine 440*b* of the data integrator controller 450 of FIG. 4B). Measurement of velocity or acceleration of chest compression during chest compressions, in one example, can be performed according to the techniques taught by U.S. Pat. No. 7,220,235, Method and Apparatus for Enhancement of Chest Compressions During Chest Compressions, the contents of which are hereby incorporated by reference in their entirety. In another example, the defibrillation unit 570 may receive chest compression measurements from a compression device platform, such as the platform 102 described in relation to FIG. 1A, the belt style compression device platform 500 of FIG. 5A, or the piston style compression device platform 530 of FIG. 5**B.

In some implementations, the CPR information in box 574 is automatically displayed when compressions are detected by the controller of the defibrillation unit 570. The information about the chest compressions displayed in box 574, in some embodiments, includes a compression rate **580*a* (e.g., number of compressions per minute) and depth 580*b*** (e.g., depth of compressions in inches or millimeters).

The information about the chest compressions displayed in box 574, in some implementations, also includes a perfusion performance indicator (PPI) 582. The PPI 582 is a shape (e.g., a diamond) with the amount of fill in the shape differing to provide feedback about both the rate and depth of the compressions. When CPR is being performed adequately, for example, at a rate of about 100 compressions/minute (CPM) with the depth of each compression greater than 1.5 inches, the entire indicator will be filled. As the rate and/or depth decreases below acceptable limits, the amount of fill lessens. The PPI 582 provides a visual indication of the quality of the CPR such that the rescuer can aim to keep the PPI 582 completely filled.

Although described in relation to the portable defibrillation unit 570, in other embodiments, a wearable cardiodefibrillator (WCD) such as the LifeVest® Wearable Cardioverter Defibrillator from ZOLL Medical Corporation (Chelmsford, Mass.) can perform similar operations to those described in relation to the portable defibrillation unit 570.

The defibrillation unit 570 may be configured to operate with various resuscitation accessory units. For example, the defibrillator 570 can include an electrical connector that is configured to operably couple to one or more accessories such as integrated therapy pad including electrodes and/or a chest compression sensor. The defibrillator can also be configured to couple to ventilator unit such as a bag valve-mask (BVM) including, for example, a ventilation bag, which is connected to a ventilation valve and a mask, as well as an integrated flow sensor. The defibrillator 570, in some embodiments, is configured to releasably couple to a removable rechargeable battery (not illustrated) accessory unit, such as the rechargeable battery unit 560 of FIG. 5C, that is configured to provide power to the defibrillation unit 570 as well as to share information with the defibrillation unit 570 as an accessory unit to the defibrillation unit 570. In some implementations, the defibrillator 570 can be further configured to couple to a medical device platform such as chest compression platform (e.g., the chest compression platform 500 of FIG. 5A or the chest compression platform 530 of FIG. 5B). The defibrillator 570 may be configured to couple to the resuscitation accessory units and/or the chest compression platform via a wired or wireless connection, as described in relation to the data integrator controller 450 of FIG. 4B.

Depending upon which patient-coupled medical device platform or accessory unit is coupled to the defibrillator 570, the defibrillator 570 can be configured to perform one or more operations and to record specific information related to the one or more operations to a non-volatile memory of the controller of the defibrillator 570 and/or to the accessory unit memory such as the non-volatile memory region **414*c* included in the accessory unit controller 460. For example, if the integrated therapy pad is coupled to the defibrillator 570, the defibrillator can receive electrical signals measured by, for example, one or more sensing electrodes integrated into the therapy pad. The defibrillator 570** can analyze the electrical signals to determine one or more physiological signals for the patient. For example, the one or more physiological signals can include heart rate metrics, RR interval metrics, heart rate variability metrics, premature ventricular complex burden or counts, atrial fibrillation burden metrics, pauses, heart rate turbulence metrics, QRS height, QRS width, changes in a size or shape of morphology of the received ECG information, cosine R-T, artificial pacing, QT interval, QT variability, T wave width, T wave *alternans*, T-wave variability, and/or ST segment changes. The defibrillator 570 can further analyze the one or more physiological signals to determine if the patient is experiencing a cardiac event such as an arrhythmia and determine whether to provide treatment such as one or more defibrillation shocks to the patient based upon the analysis.

Similarly, the defibrillator 570 can collect information from other accessories that are operably coupled to the defibrillator 570 and store the information in the memory of the defibrillator 570 and/or a memory of one or more accessories. For example, when a BVM accessory unit is coupled to the defibrillator 570, the defibrillator 570 can determine and record various information from the flow rate sensor such as respiratory rate metrics, inhaled oxygen level information, end-tidal CO2 information, and other similar metrics. In another example, when the chest compression platform is coupled to the defibrillator 570, the defibrillator can receive (or, alternatively, determine and record from raw sensor signals) various information such as chest compression rate information, chest compression depth information, and other similar metrics.

The defibrillator 570, in some implementations, records various data and metrics, as described above, to a non-volatile memory region 584. The data, for example, may be logged by the data logging engine 126*c* of FIG. 1A and archived to the non-volatile storage region 584 by the data archival engine 134*c*. The data may further be combined into metrics, in some embodiments, by the controller of the defibrillator 570.

As illustrated, in some implementations, the non-volatile storage medium 584 stores sensor data 586 such as, in some examples, a set of temperature sensor readings 586*a*, a set of current sensor readings 586*b*, a set of voltage sensor readings 586*c* and/or a set of pulse readings 586*d*. The sensor data, in some implementations, is combined to calculate metrics 588 such as, in some examples, current delivery metrics 588*b*, physiologic waveforms 588*c*, and/or blood pressure metrics 588*d*. The various data and metrics may each include a corresponding timestamp during the therapy session. At least a portion of the metrics 588 may further be associated with one or more event markers 588*a* identifying particular events during a therapy session, such as delivery of a therapeutic pulse of energy. The non-volatile storage medium 564, in further examples, may maintain device specific data and/or operational data such as a device identifier 587 and/or one or more device operational modes 589. Further operational data may include a length of activity, a battery status, and/or one or more self-test results. In additional examples, the data may include patient record code markers used in linking to patient files.

In some implementations, a chest compression medical device platform shares clinical data and/or metrics with the defibrillator 570 for incorporation into a defibrillator session summary report 581. The medical device platform and defibrillator 570 may synchronize clocks so that timestamps of the metrics 588 may be aligned with clinical data and/or metrics timestamps to merge clinical data gathered by the medical device platform with the integrator metrics 588 gathered by the defibrillator 570. The event markers 588*a*, in another example, may be aligned with event markers obtained from the medical device platform, such as compression start/stop/pause events which synchronize with delivery of shocks (e.g., current delivery metrics 588*b*) by the defibrillator 570. Further, the event markers 588*a* may be aligned with event markers obtained from an accessory unit, such as a ventilator (e.g., delivery of ventilation events).

Data Integrator as a Charging Unit

The data integrator, in some embodiments, is a rechargeable battery device charging unit designed to releasably accept one or more rechargeable battery devices, such as a rechargeable multi-cell battery pack for recharging. Turning to FIG. 5E, an example charging unit 590 is illustrated. The charging unit 590 includes two battery compartments 591*a*, 591*b*. Each compartment 591 may include a retention mechanism, such as a latch, to releasably retain a rechargeable battery unit such as the rechargeable battery unit 560 of FIG. 5C within the charging unit 590.

In some implementations, each compartment 591*a*, 591*b* of the charging unit 590 includes a connection mechanism 592*a*, 592*b* configured to connect with a connector of a rechargeable battery unit such as the rechargeable battery unit 560 of FIG. 5C. The connection mechanism 592*a*, 592*b*, for example, may be used for establishing electrical communication between the charging unit 590 and a rechargeable battery unit 560 such as the rechargeable battery unit 560 of FIG. 5C. The connection mechanism 592*a*, 592*b*, in some embodiments, not only allows for the flow of current from the charging unit 590 to recharge a power level of the rechargeable battery unit, but also provides for the sharing of data, programming commands and/or other information, such as battery charge status, discharge rate, time remaining until discharged, and the like between the rechargeable battery unit and the charging unit 590.

In some implementations, the charging unit 590 further includes a connection mechanism or data transfer mechanism (e.g., transmitter and/or receiver) for communicatively connecting the charging unit 590 to a communication network that would allow for sharing of information between the charging unit 590 and other devices such as computing devices, servers, processors and/or storage mediums. The charging unit 590 may be configured to communicate with a portion of such devices via a network. The network may be a wired network, such as, for example, an Ethernet network, or it may be a wireless network. The network may be a local network, or it may be a wide area network, such as a WLAN or the Internet. Further, the network may be a short-range RF wireless network, such as a Bluetooth, optical, or Zigbee network.

In some implementations, the charging unit 590 includes a user interface 594. The user interface 594 may include a display region, one or more status indicators (e.g., one or more light emitting diodes (LEDs) or function lights such as function lights 406*c* of the data integrator controller 450 of FIG. 4B). The status indicators may provide a visual indication of, for example, the charge/discharge status of the charging unit 590, the presence of any faults that would affect the operation of the charging unit 590, or other information that might be useful to the user of the charging unit 590.

A control button, in some implementations, is also included in the user interface 594. The control button, such as the control button(s) 406*d* of the data integrator controller 450 of FIG. 4B, may be used, for example, to initiate a diagnostic test, the results of which may be indicated by at least one of the status indicators. In further examples, the control button may be used to initiate other functions of the controller (e.g., controller 450 of FIG. 4B) in the charging unit 590, such as displaying fault codes.

In some implementations, the controller of the charging unit 590 (e.g., the controller 450 of FIG. 4B) collects data (e.g., from a number of sensors upon or within the charging unit 590) and derives metrics therefrom to store within a non-volatile storage region 596 (such as the non-volatile memory 114C of the data integrator 106 of FIG. 1A). The data, for example, may be logged by the data logging engine 126*c* of FIG. 1A and archived to the non-volatile storage region 596 by the data archival engine 134*c*. The data may further be combined into metrics, in some embodiments, by the controller of the charging unit 590.

Further, in some implementations, the controller of the charging unit 590 merges data records obtained from each of the rechargeable battery units retained in the compartments 591*a*, 591*b* of the charging unit 590. For example, the controller of the charging unit 590 may merge records using the data merging engine 144 of the data integrator 106 of FIG. 1A.

As illustrated, in some implementations, the non-volatile storage medium 596 stores sensor data 597 regarding one or more sensors of the charging unit 590 such as, in some examples, a set of temperature sensor readings 597*a*, a set of current sensor readings 597*b*, a set of voltage sensor readings 597*c* and/or a set of state-of-charge readings 597*d*. The sensor data, in some implementations, is combined to calculate metrics 598 such as, in some examples, an energy level 598*a* and a fault type 598*c*. The various data and metrics may each include a corresponding timestamp during the charging session. The non-volatile storage medium 596, in further examples, may maintain device specific data such as one or more battery identifiers 598*d* of rechargeable battery units inserted into the charging unit 590 and/or a charger identifier 599 of the charging unit 590.

Example Data Paths for Secure Data Sharing

Figure 6A:
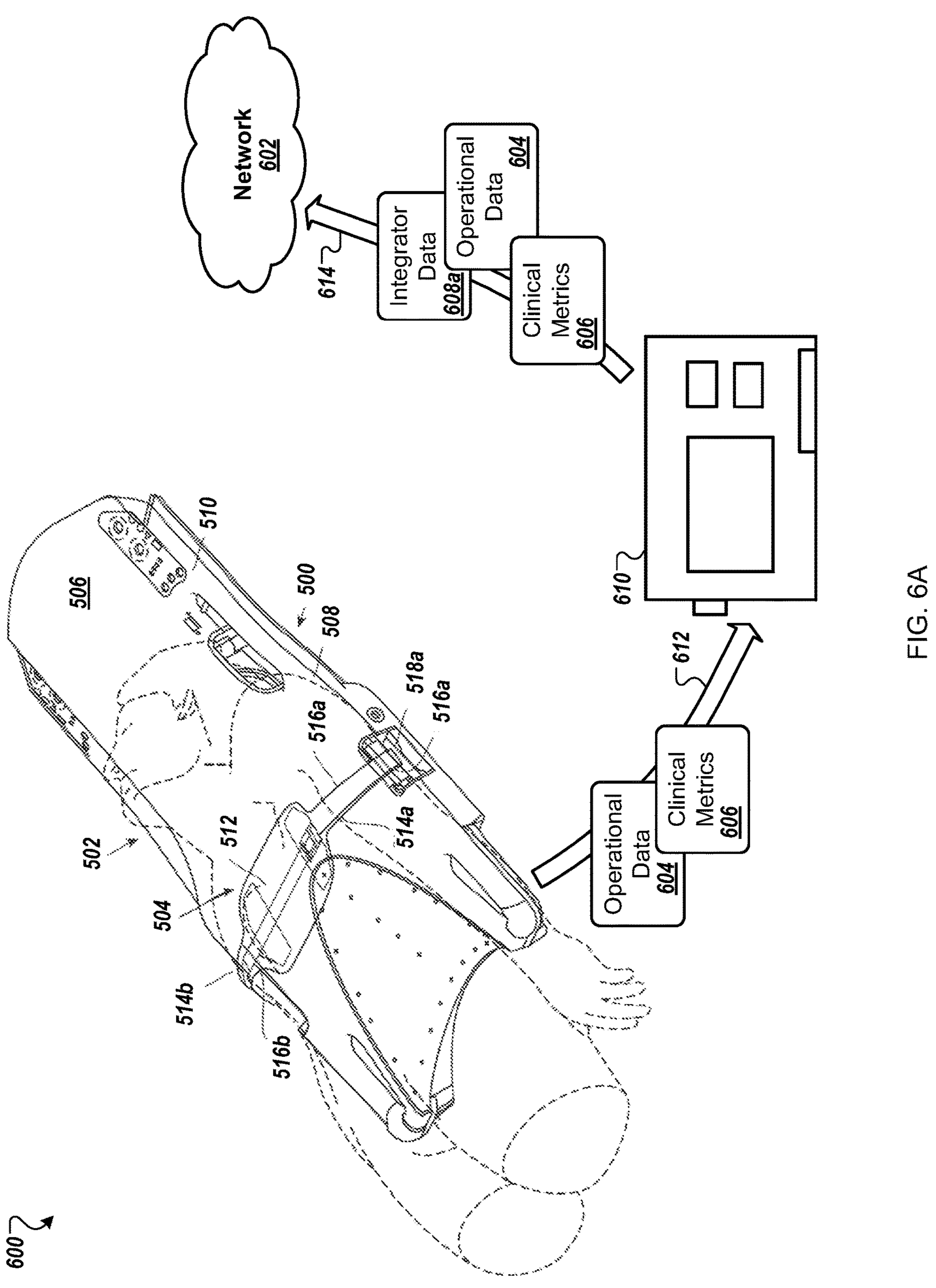
FIG. 6A is a block diagram of an example data transfer path from an automated chest compression platform to a network via a defibrillator type data integrator.
Figure 6B:
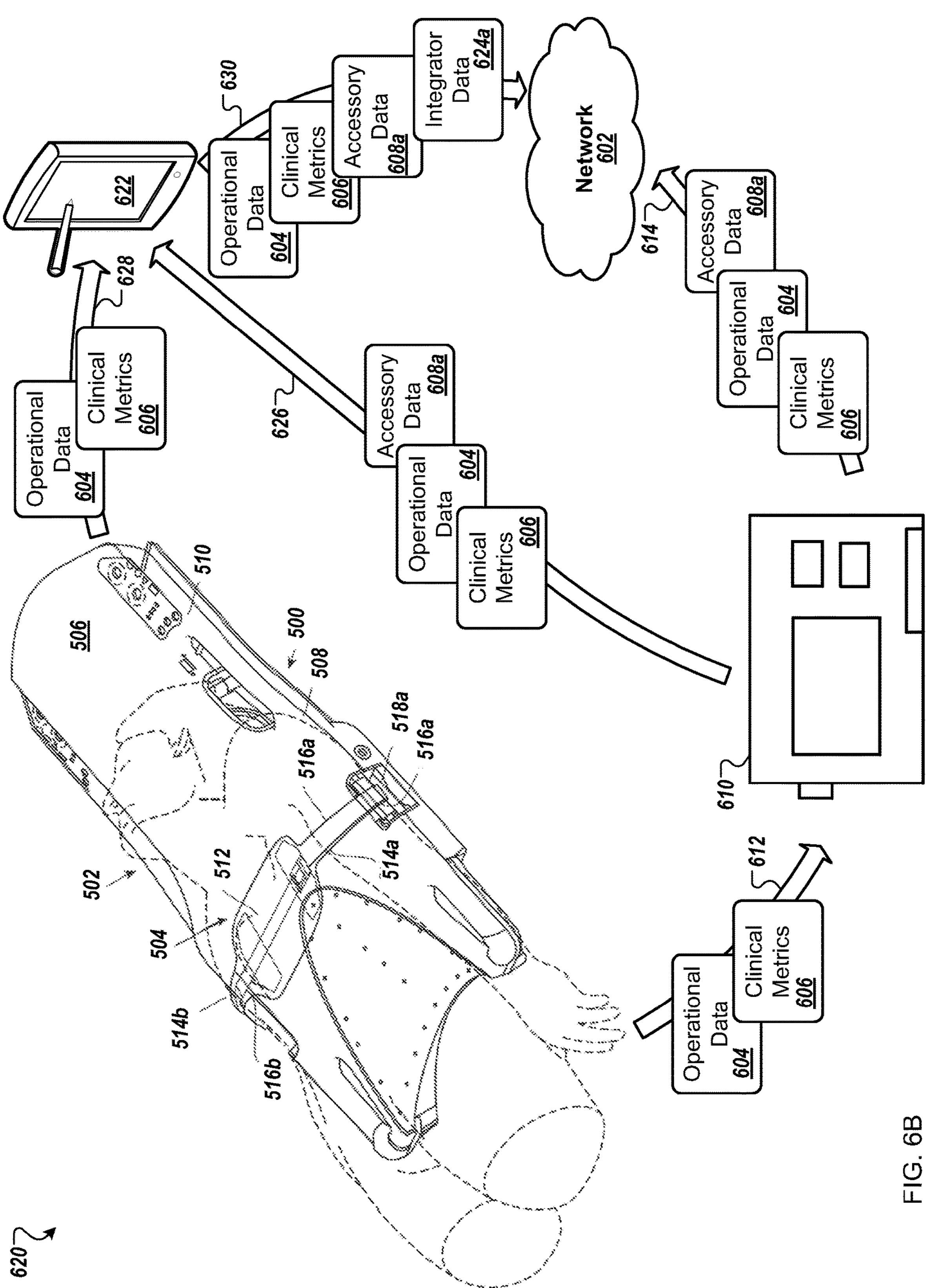
FIG. 6B is a block diagram of an example data transfer path from an automated chest compression platform to a network via a defibrillator type data accessory unit and/or a tablet computing device type data integrator.
Figure 6C:
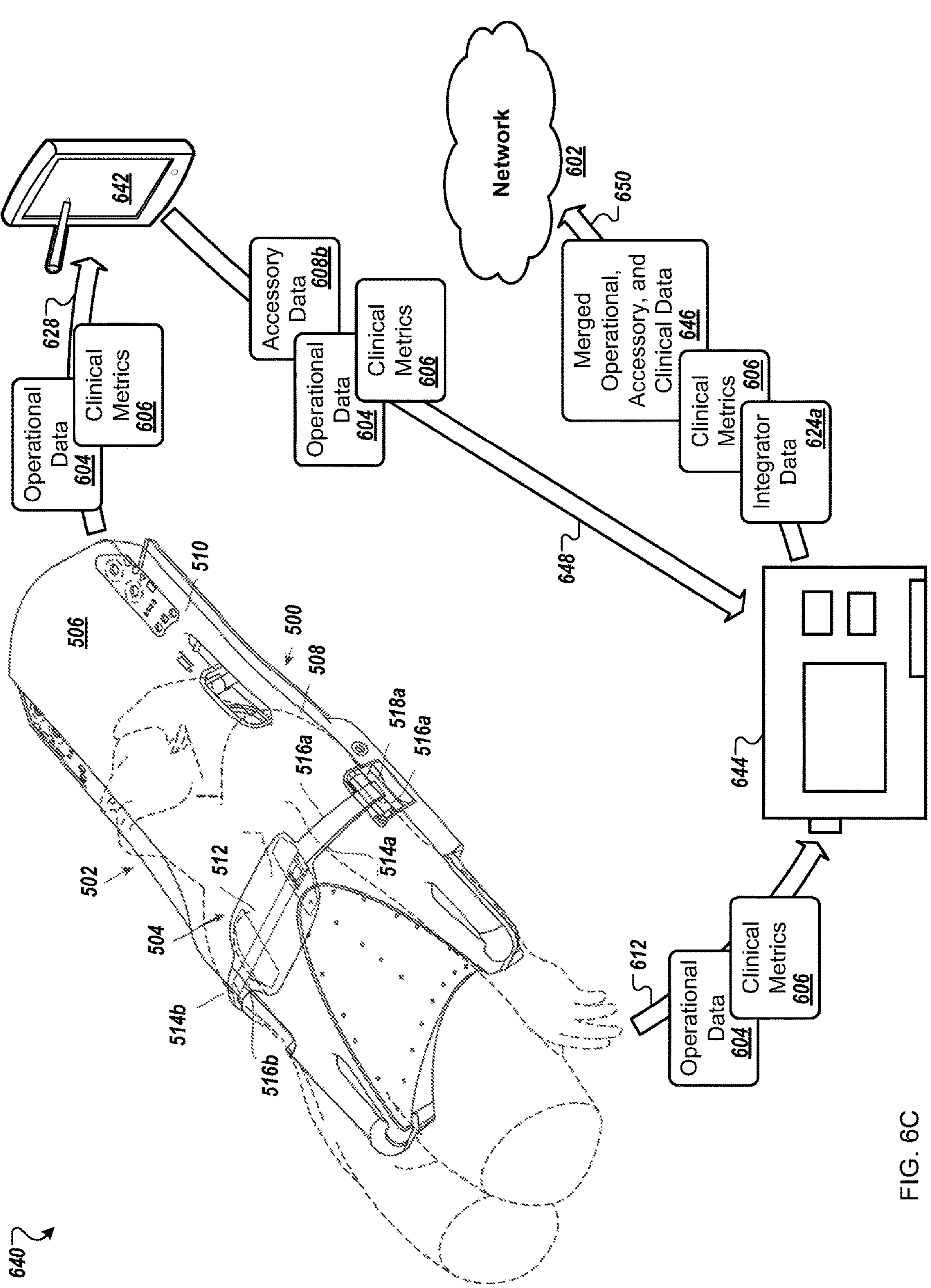
FIG. 6C is a block diagram of an example data transfer path from an automated chest compression platform to a network via a tablet computing device type accessory unit and a defibrillator type data integrator.

FIGS. 6A through 6C illustrate example data transfer paths between an automated chest compression platform, an accessory unit, and, in relation to FIGS. 6B and 6C, a data integrator. The data transfer paths may represent wired and/or wireless paths between the various environments.

FIG. 6A is a block diagram of an example data transfer path 600 from the automated chest compression platform 500 to a network 602 via a defibrillator type data integrator 610. The network 602, in some examples, may be a Wi-Fi network, short-range wireless communication network, local area network (LAN), wide area network (WAN), or the Internet. The automated chest compression platform 500, as illustrated, transfers both operational data 604 and clinical metrics 606 via the network. In other embodiments, only the operational data 604 is transferred to the network 602. In some embodiments, the operational data 604 may be transferred to a different networked device than the clinical metrics 606. For example, the operational data 604 may be provided, via the data transfer path 600, to the cloud analytics platform 110, while the clinical metrics 606 are transferred to the clinical or mobile application 112. The data transfer path 600, for example, may incorporate one or more of the local data links 128*a*, 128*b* as well as the network communication links 166*a*-166*c* as described in relation to FIG. 1A.

In some implementations, the data path 600 begins with creating a data link or data signal 612 for providing data from the automated chest compression platform 500 to the defibrillator type data integrator 610. The data may include both operational data 604 and clinical metrics 606 generated by the automated chest compression platform 500 during a therapy session.

The defibrillator type data integrator 610, in some embodiments, is configured for direct (wired) data transfer with the automated chest compression platform 500. For example, the defibrillator type data integrator 610 may be physically coupled to the automated chest compression platform 500 via a direct connector or otherwise tethered to the automated chest compression platform 500 via a data transfer cable connected to a port of the automated chest compression platform 500, such as a USB port. The data link or data signal 612, in this example, may be a serial data link or signal 612 for transferring data serially from the automated chest compression platform 500 to the defibrillator type data integrator 610. Turning to FIG. 4A, for example, the peripheral device interface 422*a* of the medical device controller 400 (e.g., disposed in the housing of the automated chest compression platform 500) may transfer the information via the port 428*a* to the defibrillator type data integrator 610.

The defibrillator type data integrator 610, in some embodiments, is configured for wireless data transfer with the automated chest compression platform 500. The connection may be a Bluetooth connection, Zigbee connection, optical connection, or other radio frequency (RF) connection for wirelessly transferring the operational data 604 and clinical metrics 606 to the defibrillator type data integrator 610. For example, as described in relation to FIG. 4A, the medical device controller 400 of the automated chest compression platform 500 may wirelessly transfer the operational data 604 and clinical metrics 606 to the defibrillator type data integrator 610 (e.g., to the accessory unit controller 460) via the wireless interface 418*a*.

In some implementations, the data path 600 continues with creating a data link or data signal 614 for providing data from the defibrillator type data integrator 610 to the network 602. The data may include both operational data 604 and clinical metrics 606 generated by the automated chest compression platform 500 during a therapy session as well as accessory data 608*a* generated by the defibrillator type data integrator 610.

The defibrillator type data integrator 610, in some embodiments, is configured for direct (wired) data transfer to the network 602. For example, the defibrillator type data integrator 610 may be physically coupled to a network port (e.g., a wall socket port, router port, network switch port, server port, etc.) via a data transfer cable, such as an Ethernet port or Fiber Distributed Data Interface (FDDI) port. The data link or data signal 614, in this example, may be a parallel data link or signal 614 for transferring data from the defibrillator type data integrator 610 to the network 602.

The defibrillator type data integrator 610, in some embodiments, is configured for wireless data transfer to the network 602. The connection may be a Wi-Fi connection or cellular communication connection (e.g., general packet radio service (GPRS), long-term evolution (LTE), code-division multiple access (CDMA), global system for mobile communications (GSM), universal mobile telecommunications service (UMTS), etc.).

In other embodiments, the device performance metrics 604 may be transferred via the data path 600 to the network 602, while the clinical metrics 606 are transferred from the automated chest compression platform 500 to a different network destination. For example, the automated chest compression platform 500 may include a wired or wireless mechanism for network communication to transfer the clinical metrics 606 to the clinical or mobile application 112. The wired or wireless mechanism, in some examples, may include a network port, Wi-Fi connection, or cellular communication connection, as described above in relation to the defibrillator type data integrator 610.

FIG. 6B is a block diagram of an example data transfer path 620 from the automated chest compression platform 500 to the network 602 via at least one of the defibrillator type accessory unit 610 and a tablet computing device type data integrator 622. In addition to the link or signal 612 between the automated chest compression platform 500 and the defibrillator type accessory unit 610 and the link or signal 614 between the defibrillator type accessory unit 610 and the network 602, the data transfer path 620 includes a second outgoing link or signal 626 to the tablet computing device type data integrator 622. In some embodiments, the redundant paths for the operational data 604, the clinical metrics 606, and the accessory data 608*a* ensure that the data reaches the network 602 despite an equipment failure, network unavailability, or differing equipment usage during the treatment session. For example, different devices, such as the defibrillator type accessory unit 610 and the tablet computing device 622, may utilize different types of network connections. In the event of unavailability of one type of network (e.g., the Ethernet connection to the Internet), the data may be uploaded to a remote computing system via another network (e.g., a cellular network or Wi-Fi network).

In some implementations, a first branch of the data path 620 begins with creating the data link or data signal 612 as described in relation to FIG. 6A. Further, the first branch of the data path 620 may continue with creating the data link or data signal 614 as described in relation to FIG. 6A.

In some implementations, in addition to the data link or data signal 614 between the defibrillator type accessory unit 610 and the network 602, the defibrillator type accessory unit 610 is configured to establish a data link or data signal 626 to transfer the clinical metrics 606, operational data 604, and accessory data 608*a* to the tablet computing device type data integrator 622.

In some embodiments, the defibrillator type accessory unit 610 is configured for direct (wired) data transfer to the tablet computing device type data integrator 622. For example, the defibrillator type accessory unit 610 may be physically coupled to the tablet computing device type data integrator 622 via a direct connector (e.g., mounting surface for a tablet device as user interface to the defibrillator type accessory unit 610) or otherwise tethered to the tablet computing device type data integrator 622 via a data transfer cable connected to a port of the tablet computing device type data integrator 622, such as a USB port. The data link or data signal 626, in this example, may be a serial data link or data signal 626 for transferring data serially from the defibrillator type accessory unit 610 to the tablet computing device type data integrator 622. Turning to FIG. 4C, for example, the peripheral device interface 422*c* of the accessory unit controller 460 may transfer the information via the port 462 to the tablet computing device type data integrator 622.

The defibrillator type accessory unit, in some embodiments, is configured for wireless data transfer to the tablet computing device type data integrator 622. The data link or data signal 626 may be a Bluetooth connection, Zigbee connection, optical connection, or other radio frequency (RF) connection for wirelessly transferring the operational data 604, clinical metrics 606, and accessory unit data 608*a* to the tablet computing device type data integrator 622. For example, as described in relation to FIG. 4C, the accessory unit controller 460 may wirelessly transfer the operational data 604, clinical metrics 606, and accessory unit data 608*a* to the tablet computing device type data integrator 622 (e.g., to the data integrator controller 450) via the wireless interface 418*c*.

The data link or data signal 626, in some implementations, connects to an alternate path for the automated chest compression platform 500 to transfer the operational data 604 and the clinical metrics 606 to the network 602. The alternate path may begin with the automated chest compression platform 500 establishing a data link or data signal 628 to the tablet computing device type data integrator 622 to transfer the operational data 604 and the clinical metrics 606 to the tablet computing device type data integrator 622.

The tablet computing device type data integrator 622, in some embodiments, is configured for direct (wired) data transfer with the automated chest compression platform 500. For example, the tablet computing device type data integrator 622 may be physically coupled to the automated chest compression platform 500 via a direct connector (e.g., mounting the tablet computing device type data integrator 622 to the automated chest compression platform 500 as a user interface device) or otherwise tethered to the automated chest compression platform 500 via a data transfer cable connected to a port of the automated chest compression platform 500, such as a USB port. The data link or data signal 628, in this example, may be a serial data link or signal 628 for transferring data serially from the automated chest compression platform 500 to the tablet computing device type data integrator 622. Turning to FIG. 4A, for example, the peripheral device interface 422*a* of the medical device controller 400 (e.g., disposed in the housing of the automated chest compression platform 500) may transfer the information via the port 428*a* to the tablet computing device type data integrator 622.

The tablet computing device type data integrator 622, in some embodiments, is configured for wireless data transfer with the automated chest compression platform 500. The connection may be a Bluetooth connection, Zigbee connection, optical connection, or other radio frequency (RF) connection for wirelessly transferring the operational data 604 and clinical metrics 606 to the tablet computing device type data integrator 622. For example, as described in relation to FIG. 4A, the medical device controller 400 of the automated chest compression platform 500 may wirelessly transfer the operational data 604 and clinical metrics 606 to the tablet computing device type data integrator 622 (e.g., to the data integrator controller 450) via the wireless interface 418*a*.

In some implementations, the data path 600 continues with creating a data link or data signal 630 for providing data from the tablet computing device type data integrator 622 to the network 602. The data may include the operational data 604, the clinical metrics 606, the accessory data 608*a*, as well as integrator data 624*a* generated by the tablet computing device type data integrator 622.

The tablet computing device type data integrator 622, in some embodiments, is configured for direct (wired) data transfer to the network 602. For example, the tablet computing device type data integrator 622 may be physically coupled to a network port (e.g., a wall socket port, router port, network switch port, server port, etc.) via a data transfer cable, such as an Ethernet cable or Fiber Distributed Data Interface (FDDI) cable. The data link or data signal 630, in this example, may be a parallel data link or signal

630 for transferring data from the tablet computing device type data integrator 622 to the network 602.

The tablet computing device type data integrator 622, in some embodiments, is configured for wireless data transfer to the network 602. The data link or data signal 630 may be a Wi-Fi connection or cellular communication connection (e.g., general packet radio service (GPRS), long-term evolution (LTE), code-division multiple access (CDMA), global system for mobile communications (GSM), universal mobile telecommunications service (UMTS), etc.).

In some embodiments, prior to transferring the operational data 604, the clinical metrics 606, the accessory data 608*a*, and the integrator data 624*a* to the network 602 via the data link or data signal 630, the tablet computing device type data integrator 622 removes duplicate information (e.g., data files and/or data records) between operational data 604 and/or clinical metrics 606 provided by both the automated chest compression platform 500 (e.g., via the data link or data signal 628) and the defibrillator type accessory unit 610 (e.g., via the data link or data signal 626). For example, the data archival engine 134*c* of the data integrator 106 of FIG. 1A may archive multiple collections of operational data 604 and/or clinical metrics 606 to the non-volatile memory 114*c* while removing any duplicate information prior to transferring further. In other embodiments, the cloud analytics platform 110 of FIG. 1A may remove duplicate records (e.g., by the record inking engine 154). The duplicate information, for example, may involve a full set of session data (e.g., operational data 604 and clinical metrics 606). In another example, a full version of the operational data 604 may be provided via a first branch of the data path 620, while a portion of the operational data 604 may be provided via the other branch of the data path 620. In illustration, using a low power Bluetooth signal, the automated chest compression platform 500 may issue a portion of the operational data 604 to the defibrillator type accessory unit via the data link or data signal 612, while when using a more powerful and/or higher bandwidth tethered connection or Wi-Fi connection, the automated chest compression platform 500 may transmit a full set of the operational data 604 via the data link or data signal 628 to the tablet computing device type data integrator 622. The portion of the data, for example, may be higher priority data such as device performance metrics related to the patient's treatment session. The portion of the data, for example, may be issued on a periodic basis such as, in some examples, every second, every five seconds, or every ten seconds. The remainder of the operational data 604, for example, may include sensor data and/or device identifying data.

In other embodiments, rather than separately sharing the operational data 604, the accessory data 608*a*, and the integrator data 624*a* with the network 602, the tablet computing device type data integrator 622 is configured to merge records of the operational data 604, the accessory data 608*a*, and the integrator data 624*a*, for example based upon time stamps and/or event markers in the operational data 604, the accessory data 608*a*, and the integrator data 624*a*. In one example, the data merging engine 144 may be configured to merge the operational data 604, the accessory data 608*a*, and the integrator data 624*a* records prior to supplying merged records to the network 602.

In some implementations, a same device may behave as either an accessory unit or a data integrator. In one example, the behavior may depend in part upon availability of a high speed connection to the network 602. For example, if the tablet computing device is only configured for wireless data transfer to a network (e.g., Wi-Fi or cellular), and the wireless communication must be turned off during the treatment session due to the potential for interference with other equipment within the medical facility, and the defibrillator has a wired connection to an available network, then the defibrillator may behave as the data integrator to collect data from the various devices in the medical resuscitation system and to provide the data to the network 602 (e.g., possibly after merging records of the collected data). In another example, the behavior of a given device as a data integrator or an accessory unit may depend in part upon a connection relationship with other elements of the medical resuscitation system. For example, the automated chest compression platform 500 may wirelessly broadcast (e.g., via Bluetooth) the operational data 604 and clinical metrics 606 so that it may be received and stored by the defibrillator or an accessory unit such as a tablet computing device, but without any confirmation of receipt. Conversely, the automated chest compression platform 500 may establish a bi-directional communication like with the tablet computing device or defibrillator, thus receiving confirmation of the transfer of the operational data 604 and clinical metrics 606 by the tablet computing device 622 or defibrillator. In some embodiments, the device performing the operations of data integrator may be automatically selected at time of creating the data transfer path (e.g., through establishing a Zigbee network, token ring network, or other localized network of devices). Finally, the behavior of a particular device as an accessory unit or a data integrator may be established in part through user settings of the device.

Turning to FIG. 6C, a block diagram of an example data transfer path 640 from the automated chest compression platform 500 to the network 602 utilizes a tablet computing device as an accessory unit 642 and a defibrillator as a data integrator 644, differing from the data path architecture of FIG. 6B where the tablet computing device behaved as a data integrator and the defibrillator behaved as an accessory unit.

In some implementations, a first branch of the data path 640 begins with creating the data link or data signal 612 from the automated chest compression platform 500 to a defibrillator type data integrator 644, similar to the description provided in relation to FIG. 6A in reference to the defibrillator type accessory unit 610. Further, a second branch of the data path 640 begins with creating the data link or data signal 628 from the automated chest compression platform 500 to a tablet computing device type accessory unit 642, similar to the description provided in relation to FIG. 6B in reference to the tablet computing device type data integrator 622. The operational data 604 and clinical metrics 606, for example, may have similar contents as described above in relation to FIGS. 6A and 6B, in various embodiments.

The second branch, in some implementations, continues with the tablet computing device type accessory unit 642 forwarding the operational data 604 and the clinical metrics 606 along with its accessory data 608*b* to the defibrillator type data integrator 644 via a data link or data signal 648. The accessory data 608*b*, for example, may include a log of user inputs to the medical resuscitation system (e.g., to the automated chest compression platform 500 and/or the defibrillator type data integrator 644) submitted via a user interface provided by the tablet computing device type accessory unit 642. In other embodiments, since the tablet computing device type accessory unit 642 is not a medical device, the tablet computing device type accessory unit 642 only forwards the operational data 604 and the clinical metrics 606.

In some embodiments, tablet computing device type accessory unit 642 is configured for direct (wired) data transfer to the defibrillator type data integrator 644. For example, the computing device type accessory unit 642 may be physically coupled to the defibrillator type data integrator 644 via a direct connector (e.g., mounting surface for a tablet device as user interface to the defibrillator type data integrator 644) or otherwise tethered to the defibrillator type data integrator 644 via a data transfer cable connected to a port of tablet computing device type accessory unit 642, such as a USB port. The data link or data signal 648, in this example, may be a serial data link or data signal 648 for transferring data serially from the tablet computing device type accessory unit 642 to the defibrillator type data integrator 644. Turning to FIG. 4C, for example, the peripheral device interface 422*c* of the accessory unit controller 460 may transfer the information via the port 462 to the defibrillator type data integrator 644.

The tablet computing device type accessory unit 642, in some embodiments, is configured for wireless data transfer to the defibrillator type data integrator 644. The data link or data signal 648 may be a Bluetooth connection, Zigbee connection, optical connection, or other radio frequency (RF) connection for wirelessly transferring the operational data 604, clinical metrics 606, and accessory unit data 608*b* to the defibrillator type data integrator 644. In another example, the data link or data signal 648 may be a Wi-Fi connection for wirelessly transferring the operational data 604, clinical metrics 606, and accessory unit data 608*b* to the defibrillator type data integrator 644. For example, as described in relation to FIG. 4C, the accessory unit controller 460 may wirelessly transfer the operational data 604, clinical metrics 606, and accessory unit data 608*b* to the defibrillator type data integrator 644 (e.g., to the data integrator controller 450) via the wireless interface 418*c*.

In continuation with the first branch of the data path 640, in some implementations, the defibrillator type data integrator 644 establishes a data link or data signal 650 for providing data from the defibrillator type data integrator 644 to the network 602. The data, as illustrated includes merged operational, accessory, and clinical data 646 as well as the clinical metrics 606. The merged operational, accessory, and clinical data 646, for example, may be generated by the data merging engine 144 of the data integrator 106 of FIG. 1A. In other embodiments, the data may include the operational data 604, the clinical metrics 606, the accessory data 608*a*, as well as integrator data 624*a* generated by the defibrillator type data integrator 644.

The defibrillator type data integrator 644, in some embodiments, is configured for direct (wired) data transfer to the network 602. For example, the defibrillator type data integrator 644 may be physically coupled to a network port (e.g., a wall socket port, router port, network switch port, server port, etc.) via a data transfer cable, such as an Ethernet cable or Fiber Distributed Data Interface (FDDI) cable. The data link or data signal 650, in this example, may be a parallel data link or signal 650 for transferring data from the defibrillator type data integrator 644 to the network 602.

The defibrillator type data integrator 644, in some embodiments, is configured for wireless data transfer to the network 602. The data link or data signal 650 may be a Wi-Fi connection or cellular communication connection (e.g., general packet radio service (GPRS), long-term evolution (LTE), code-division multiple access (CDMA), global system for mobile communications (GSM), universal mobile telecommunications service (UMTS), etc.).

While certain embodiments have been described, these embodiments have been presented by way of example only, and are not intended to limit the scope of the present disclosures. Indeed, the novel methods, apparatuses and systems described herein can be embodied in a variety of other forms; furthermore, various omissions, substitutions and changes in the form of the methods, apparatuses and systems described herein can be made without departing from the spirit of the present disclosures. The accompanying claims and their equivalents are intended to cover such forms or modifications as would fall within the scope and spirit of the present disclosures.

What is claimed is:

1. A medical resuscitation system comprising:

a medical device platform configured for releasable coupling to a patient for delivery of mechanical chest compressions, the medical device platform comprising:

at least one sensor for monitoring at least one aspect of the delivery of the mechanical chest compressions; and a housing comprising:

at least one communications link;

a non-volatile memory; and processing circuitry configured to:

control the delivery of the mechanical chest compressions during a session of therapy delivery to the patient;

receive, during the session, a plurality of signals from each sensor of the at least one sensor;

store, to the non-volatile memory operational data comprising at least one of a) the plurality of signals or b) at least one device performance metric derived from the plurality of signals, and clinical data comprising a plurality of clinical metrics regarding the delivery of the mechanical chest compressions during the session, wherein the plurality of clinical metrics is derived from at least a portion of the plurality of signals;

format the operational data to be protected from access absent authorized user credentials;

encrypt at least a portion of the clinical data;

transfer, via the at least one communications link, the operational data to a server for use by one or more authorized users in troubleshooting a problem or error condition in the platform; and separately transfer, via the at least one communications link, the clinical data to a different storage medium, device, or network connection than the operational data for use by at least one of an analytics platform or a mobile application, wherein the analytics platform or the mobile application is configured to provide at least a portion of the clinical data for review by a clinical user authorized to view the clinical data.

2. The medical resuscitation system according to claim 1, wherein transferring the clinical data comprises transferring via a wired connection of the at least one communications link.

3. The medical resuscitation system according to claim 2, wherein the at least one communications link comprises an Ethernet port for providing the wired connection.

4. The medical resuscitation system according to claim 1, wherein the clinical data is automatically transferred periodically during the session.

5. The medical resuscitation system according to claim 1, wherein:

the platform comprises a data transmit control; and the processing circuitry is further configured to receive a control signal indicative of user activation of the data transmit control, and responsive to receiving the control signal, transfer the operational data to an accessory unit or a data integrator.

6. The medical resuscitation system according to claim 5, wherein the accessory unit or the data integrator is a portable computing device.

7. The medical resuscitation system according to claim 1, wherein the operational data is collected for use in gathering historic data regarding use of the platform.

8. The medical resuscitation system according to claim 1, wherein the plurality of clinical metrics includes force, depth, rate, duty cycle, or other clinical performance parameters of the mechanical chest compressions.

9. The medical resuscitation system according to claim 1, wherein the at least one sensor comprises at least one of a voltage sensor, a temperature sensor, a current sensor, a position encoder, or an airflow sensor.

10. The medical resuscitation system according to claim 9, wherein the operational data includes a motor temperature, operational voltages, currents, run time, failure modes, and/or service or system maintenance related warnings or alerts of the medical resuscitation system.

11. The medical resuscitation system according to claim 1, wherein the at least one device performance metric comprises at least one of a temperature, a voltage, an error code, or a platform tilt angle.

12. The medical resuscitation system according to claim 1, wherein the at least one sensor comprises a GPS receiver, wherein the session begin time is derived from a current time obtained via the GPS receiver.

13. The medical resuscitation system according to claim 1, wherein transferring the operational data comprises transferring the operational data after the session has ended.

14. The medical resuscitation system according to claim 1, wherein:

the at least one communications link comprises a wireless transmitter; and transferring the operational data comprises transferring the operational data via the wireless transmitter.

15. The medical resuscitation system according to claim 14, wherein the wireless transmitter is one of a cellular transmitter or a Wi-Fi transmitter.

16. The medical resuscitation system according to claim 1, wherein the clinical data is used by the at least one of the analytics platform or the mobile application in a summary report view of therapy delivered during a treatment session, wherein the summary report view is provided by the analytics platform or the mobile application for review by the clinical user.

17. The medical resuscitation system according to claim 16, wherein the summary report view comprises a location of treatment.

18. The medical resuscitation system according to claim 16, wherein the summary report view comprises one or more of a session begin time, a session end time, a device identifier, or a session length.

19. A medical resuscitation system comprising:

a medical device platform configured for releasable coupling to a patient for delivery of mechanical chest compressions, the medical device platform comprising:

at least one sensor for monitoring at least one aspect of the delivery of the mechanical chest compressions; and a housing comprising:

at least one communications link;

a non-volatile memory; and processing circuitry configured to:

control the delivery of the mechanical chest compressions during a session of therapy delivery to the patient;

receive, during the session, a plurality of signals from each sensor of the at least one sensor;

store, to the non-volatile memory operational data comprising at least one of a) the plurality of signals or b) at least one device performance metric derived from the plurality of signals, and clinical data comprising a plurality of clinical metrics regarding the delivery of the mechanical chest compressions during the session, wherein the plurality of clinical metrics is derived from at least a portion of the plurality of signals;

format the operational data to be protected from access absent authorized user credentials;

encrypt at least a portion of the clinical data, wherein the clinical data is formatted differently than the operational data;

transfer, via the at least one communications link, the operational data to a server for use by one or more authorized users in troubleshooting a problem or error condition in the platform; and transfer, via the at least one communications link, the clinical data to at least one of an analytics platform or a mobile application, wherein the analytics platform or the mobile application is configured to provide at least a portion of the clinical data for review by a clinical user authorized to view the clinical data, wherein the authorized user credentials lack privileges for viewing the clinical data, and the clinical user lacks privileges for viewing the operational data.

20. The medical resuscitation system of claim 19, wherein formatting the operational data to be protected from access absent the authorized user credentials comprises storing, to the non-volatile memory, the operational data in a protected format.

21. The medical resuscitation system of claim 19, wherein the transferred clinical data is received at a different storage medium, device, or network connection than the transferred operational data.

* * * * *